United States Patent
Miyoshi et al.

(10) Patent No.: US 6,172,099 B1
(45) Date of Patent: Jan. 9, 2001

(54) TRICYCLIC COMPOUNDS HAVING SATURATED RINGS AND MEDICINAL COMPOSITIONS CONTAINING THE SAME

(75) Inventors: Shiro Miyoshi, Fuji; Kohei Ogawa, Mishima, both of (JP)

(73) Assignee: Asahi Kasei Kogyo Kabushiki Kaisha (JP)

( * ) Notice: Under 35 U.S.C. 154(b), the term of this patent shall be extended for 0 days.

(21) Appl. No.: 09/446,515

(22) PCT Filed: Jun. 17, 1998

(86) PCT No.: PCT/JP98/02680

§ 371 Date: Mar. 27, 2000

§ 102(e) Date: Mar. 27, 2000

(87) PCT Pub. No.: WO99/01431

PCT Pub. Date: Jan. 14, 1999

(30) Foreign Application Priority Data

Jul. 3, 1997 (JP) .................................................. 9-178197

(51) Int. Cl.[7] ...................... A61K 31/343; A61K 31/403; C07D 307/91; C07D 209/82
(52) U.S. Cl. ............................ 514/411; 548/439; 549/48; 549/460
(58) Field of Search ............................... 548/439; 549/48, 549/460; 514/411

(56) References Cited

U.S. PATENT DOCUMENTS

| | | |
|---|---|---|
| 4,338,333 | 7/1982 | Ainsworth et al. . |
| 5,061,727 | 10/1991 | Bloom et al. . |
| 5,120,766 | 6/1992 | Holloway et al. . |
| 5,541,197 | 7/1996 | Fisher et al. . |
| 5,767,133 | 6/1998 | Dow et al. . |
| 5,776,983 | 7/1998 | Washburn et al. . |

FOREIGN PATENT DOCUMENTS

| | | |
|---|---|---|
| 0 171 702 A1 | 2/1986 | (EP) . |
| 0 882 707 A1 | 12/1998 | (EP) . |
| 1 565 080 | 4/1980 | (GB) . |
| 55-53262 | 4/1980 | (JP) . |
| 58-41860 | 3/1983 | (JP) . |
| 8-165276 | 6/1996 | (JP) . |

OTHER PUBLICATIONS

Miyoshi et al, Chemical Abstracts, vol. 133, No. 43540, 2000.*

Arch et al., Atypical β–adrenoceptor on brown adipocytes as target for anti–obesity drugs, Nature 309 10 (1984) p. 163–65.

Emorine et al., Molecular Characterization of the Human $\beta_3$–Adrenergic Receptor, Science 245 (1989) p. 1118–21.

Cawthrone et al., Effects of Novel β–Adrenoceptor Agonists on Carbohydrate Metabolism, International Journal of Obesity (1984) 8, Suppl. 1, p. 93–102.

McLaughlin et al., Characterization of catecholamine–mediated relaxations in rat isolated gastric fundus evidence for an atypical β–adrenoceptor, Br. J. Pharmacol. (1991), 103, p. 1351–1356.

Simiand et al., Antidepressant profile in rodents of SR 58611A, a new selective agonist for atypical β–adrenoceptors, European Journal of Pharmacology, 219 (1992) p. 193–201.

BRL 35135, Drugs of the Future 1991, 16(9): p. 797–800.

Bloom et al., J. Med., Chem., 1992, 35, p. 3081–84.

* cited by examiner

Primary Examiner—Robert W. Ramsuer
(74) Attorney, Agent, or Firm—Pennie & Edmonds LLP

(57) ABSTRACT

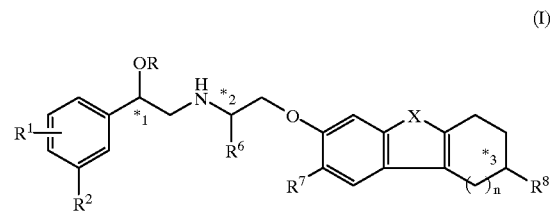

Compounds represented by general formula (I) or their salts, having $\beta_3$-adrenoceptor agonism and being efficacious when employed in drugs for treating and preventing diabetes, obesity, hyperlipemia, etc. wherein R represents hydrogen or methyl; $R^1$ represents hydrogen, halogeno, hydroxy, benzyloxy, amino or hydroxymethyl; $R^2$ represents hydrogen, hydroxymethyl, $NHR^3$, $SO_2NR^4R^{4'}$ or nitro (wherein $R^3$ represents hydrogen, methyl, $SO_2R^5$, formyl or $CONHR^{6'}$; $R^5$ represents lower alkyl, benzyl or $NR^4R^{4'}$; $R^4$ and $R^{4'}$ may be the same or different and each represents hydrogen, lower alkyl or benzyl; and $R^{6'}$ represents hydrogen or lower alkyl); $R^6$ represents hydrogen or lower alkyl; n is 1 or 2; X represents secondary nitrogen, oxygen or sulfur; and when n is 1, then one of $R^7$ and $R^8$ represents hydrogen while another represents hydrogen, amino, acetylamino or hydroxy, or when n is 2, then $R^8$ represents hydrogen while $R^7$ represents hydrogen, amino, acetylamino or hydroxy.

17 Claims, No Drawings

TRICYCLIC COMPOUNDS HAVING SATURATED RINGS AND MEDICINAL COMPOSITIONS CONTAINING THE SAME

FIELD OF THE INVENTION

The present invention relates to novel tricyclic compounds having saturated rings and to medicinal compositions containing such tricyclic compounds.

PRIOR ARTS

In the past, it was accepted that β-adrenaline receptors are classified into two groups β1 and β2, wherein the stimulation by β1 induces an increase in the cardiac rate and the stimulation by β2 brings about relaxation in the smooth muscle tissue and lowering of blood pressure. Arch et al. discovered a compound which exhibits scarce activities to β1 and β2 but emphasizes lipolysis of fatty cells, wherefrom they have made clear the existence of a third receptor [Nature, 309, 163–165 (1984)]. Later, the primary structure thereof was clarified [Emorine et al.: Science, Vol. 245, 1118–1121 (1989)]and the receptor was named as β3.

Recently, it has been shown that compounds exhibiting a β3-activity are useful as a drug for preventive treatment of diabetes, obesity, hyperlipemia, digestive diseases and depression [Int. J. Obesity 8 (suppl.1), 93–102 (1984); Nature, 309, 163–165 (1984); U.S. Pat. No. 5,120,766; Brit. J. Pharmacol., 103, 1351–1356 (1991); Eur. J. Pharmacol., 219, 193–201 (1992)].

Various compounds with correlation to β3 have been reported in the literatures, for example, a compound (BRL 37344) having the following molecular structure

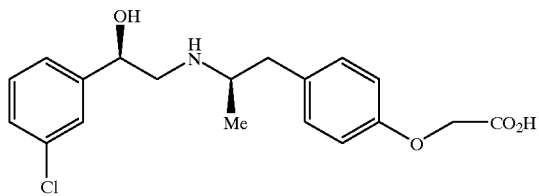

as disclosed in EP 023 385 and in Drugs of the Future, Vol. 16, 797–800 (1991); a compound (CL316,243) having the following molecular structure

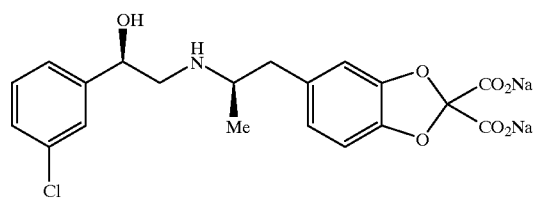

as disclosed in EP 0 455 006 and J. Med. Chem.,Vol. 35, 3081–3084 (1992); a compound having the following molecular structure

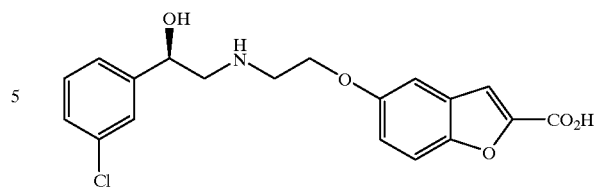

as disclosed in WO9429290; and a compound having the following molecular structure

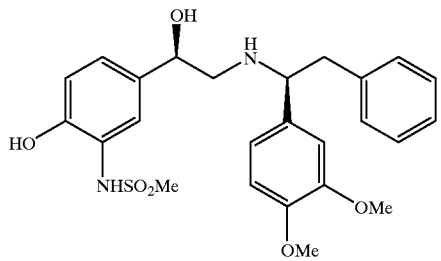

as disclosed in EP 0 659 737 in Example 1 thereof. All these compounds have molecular structures different clearly from that of the compound according to the present invention.

There was known a compound exhibiting a function for increasing the myocardial contraction strength and for antagonizing obesity represented by the following structural formula

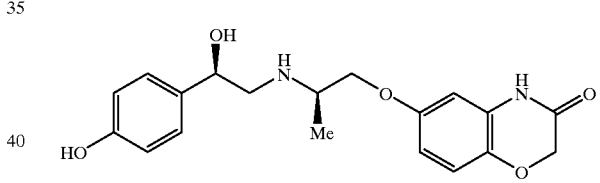

as disclosed in EP 171 702, which is distinguished from the compound according to the present invention in that it has a strong pharmacological activity onto heart and has a molecular structure quite different from that of the compound according to the present invention.

Further, a compound exhibiting an α, β-blocking activity, namely, a function of lowering the blood pressure, represented by the following structural formula

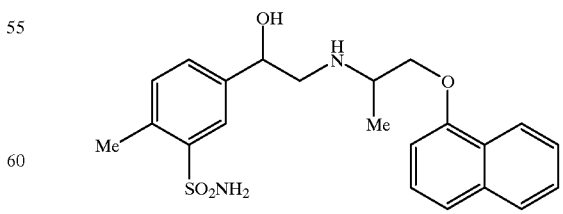

is disclosed in Japanese Patent Kokai is Sho 55-53262 and Sho 58-41860 and a compound exhibiting a vasodilating function having the following structural formula

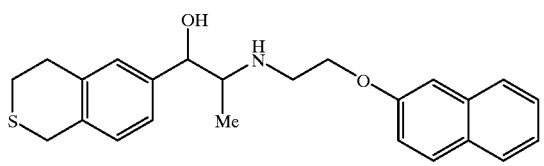

is disclosed in DE 2 651 572. They are different from the compound according to the present invention in the molecular structure and in the function.

Problems to be solved by the invention

There is a demand for novel and effective medicament which can be used for therapeutic treatment and preventive treatment of diseases correlating to β3, such as diabetes, obesity and hyperlipemia.

Means for solving the problems

The inventors of the present invention had been synthesized various compounds and studied on these activities and functions in order to solve the above problems and reached the discovery that novel tricyclic compounds having saturated rings represnted by the general formula (I) given below had β3-activities with functions for lowering blood glucose level and for lypolysis, thereby led to the completion of the present invention.

Thus, the present invention comprises in a compound represented by the general formula (I) or a salt thereof:

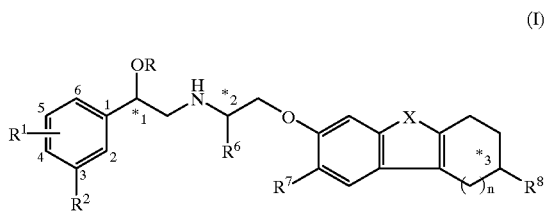

(I)

in which R represents hydrogen atom or methyl, R1 stands for hydrogen atom, halogen atom, hydroxy, benzyloxy, amino or hydroxymethyl, R2 stands for hydrogen atom, hydroxymethyl, NHR3, SO2NR4R4' or nitro, wherein R3 is hydrogen atom, methyl, SO2R5, formyl or CONHR6', with R5 being lower alkyl, benzyl or NR4R4' and R4 and R4' may be identical with or different from each other and stand each for hydrogen atom, lower alkyl or benzyl, and R6' being hydrogen atom or lower alkyl, R6 represents hydrogen atom or lower alkyl, n is 1 or 2, X stands for a secondary nitrogen atom, oxygen atom or sulfur atom and, in case that n is 1, either one of R7 and R8 is hydrogen atom and the other one is hydrogen atom, amino, acetylamino or hydroxy, or, in case that n is 2, R8 is hydrogen atom, and R7 is hydrogen atom, amino, acetylamino or hydroxy, *1 indicates an asymmetric carbon atom and *2 and *3 indicate asymmetric carbon atom in case that R6 and R8 are not hydrogen atom.

According to the present invention, there fluorine atom, chlorine atom, bromine atom or iodine atom may be exemplified for the halogen atom, and among them, fluorine atom and chlorine atom are preferred. In the context of the present invention, "lower alkyl" means a straight or branched chain saturated hydrocarbon having 1–4 carbon atoms, such as methyl, ethyl, n-propyl, i-propyl, i-butyl, s-butyl and t-butyl.

In the formula (I), R may preferably be hydrogen atom, while R may favorably be also methyl for reason of providing more higher selectivity. R1 stands for hydrogen atom, halogen atom, hydroxy, benzyloxy, amino or hydroxymethyl. A preferred example of the compound represented by the general formula (I) is one in which R1 denotes hydrogen atom. Also preferred example of the compound represented by the general formula (I) is one in which R1 denotes amino or hydroxymethyl group. A further preferred example of the compound represented by the general formula (I) is one in which R1 denotes halogen atom or hydroxy or benzyloxy group.

R2 stands for hydrogen atom, hydroxymethyl, NHR3, SO2NR4R4' or nitro. A preferred example of the compound represented by the general formula (I) is one in which R1 denotes hydrogen atom. Also preferred example of the compound represented by the general formula (I) is one in which R2 is hydroxymethyl or nitro group. A further preferred example of the compound represented by the general formula (I) is one in which R2 stands for NHR3 or SO2NR4R'. R3 in the group NHR3 may be hydrogen atom, methyl, SO2R5, formyl or CONHR6', wherein reference is given especially to NHR3 which is NH2, NHMe, NHSO2R5, NHCHO and NHCONHR6' among which NHSO2R5 is more preferable. In the group NHSO2R5, R5 stands for lower alkyl, benzyl or NR4R4'. R4 and R4' may be either be identical with or different from each other and may stand each for hydrogen atom, lower alkyl or benzyl, wherein either one of R4 and R4' is preferably hydrogen.

Concrete examples of NR4R4' include amino, methylamino, ethylamino, propylamino, benzylamino, dimethylamino, diethylamino, dipropylamino, methylethylamino, methylpropylamino and methylbenzylamino, among which preference is given to methylamino and dimethylamino. Therefore, preferred concrete examples of NHSO2R5 include NHSO2Me, NHSO2Et, NHSO2CH2Ph, NHSO2NH2, NHSO2NHMe, NHSO2NHEt, NHSO2NMe2, NHSO2NEt2, NHSO2NMeEt and NHSO2NMeCH2Ph. R6' in the group NHCONHR6' is hydrogen atom or lower alkyl, Concrete examples of NHCONHR6' include NHCONH2, NHCONHMe, NHCONHEt and NHCONHPr. Concerning the group SO2NR4R4' for the group R2,the groups R4 and R4' have the same meanings as given above and may either be identical with or different from each other and may stand for hydrogen atom, lower alkyl or benzyl, wherein it is preferable that either one of R4 and R4' is hydrogen atom. Therefore, concrete examples of the group SO2NR4R4' include SO2NH2, SO2NHMe, SO2NHEt, SO2NMe2, SO2NEt2, SO2NHCH2Ph or SO2NMeCH2Ph.

R6 represents hydrogen atom or lower alkyl. Preferred examples include hydrogen atom, methyl and ethyl. Here, preference is given to the case where it stands for hydrogen atom.

Example of n is 1 or 2, and preferred example is that n is 1.

X stands for secondary nitrogen atom, oxygen atom or sulfur atom. A preferred example of the compound is one in which X is secondary nitrogen atom, and n is 1, namely, the tricyclic skeleton is constituted of tetrahydrocarbazole group. Here, the groups R7 and R8 have the meanings as given previously.

The symbol *1 in the general formula (I) wherein R8 is hydrogen atom, indicates an asymmetric carbon atom and, in case that R6 is lower alkyl, the symbol *2 also indicates an asymmetric carbon atom. In this case, the compound of the general formula (I) may be present in four different isomers, namely, (R, R), (R, S), (S, S) and (S, R) represented by the sequence oder of (*1 and *2). In case that R6 is hydrogen atom, two isomers are possible. The present invention encompasses not only optically pure isomer, but also mixtures of two voluntarily selected isomer, of three voluntarily selected isomers and of all four isomers. From the point of view of development of the pharmacological activity, an asymmetric carbon atom (*1) in the ethanolamino chain may preferably have an absolute configuration (R). Concerning the asymmetric carbon atom (*1) for N-[5-[2-[2-(5,6,7,8-tetrahydro-9H-carbazol-2-yloxy)ethylamino]-1-hydroxyethyl]-2-hydroxyphenyl]methanesulfonamide, especially preferred examples are R-hydroxy compounds.

Further, in the formula (I), in case that R8 is not hydrogewn atom, *3 is an asymmetric carbon atom. In case that *1 is asymmetric carbon atom and R6 is lower alkyl, *2 is asymmetric carbon atom. In that case, asymmetric carbon atoms constitute at maximum 3 asymmetric carbon atoms. Consequently, in the compound (I), 8 different isomers are existed. In the present invention, not only the pure optical isomers but also mixtures of arbitrary isomers may be included. From the standpoint of exhibiting pharmacological activity, preferable configuration of asymmetric carbon in ethanolamine chain (*1) is absolute configuration R. Though *3 is asymmetric carbon atom, it may be optical isomer or racemic mixture.

For the compound according to the present invention, there are very favorable groups of combinations of the substituent groups. In the following, the symbols R6, n, X, R7, R8, *1, *2 and *3 for the general formula (I) have the meanings as defined above, so long as no special mention is made.

When R2 in the general formula (I) for the compound according to the present invention represents hydroxymethyl, NHR3, SO2NR4R4' or nitro, it is preferable that the group R1 is in the 4- or 5-position, wherein preference is given to the case where R1 is in 4-position. When R2 is hydrogen atom, it is more preferable that R1 is in the 2-position.

Preferred examples of the compound represented by the general formula (I) or the salt thereof according to the present invention are those in which the combination of the substituent groups in the general formula (I) is such that "R represents hydrogen atom, R1 stands for hydrogen atom, halogen atom, hydroxy, benzyloxy, amino or hydroxymethyl and R2 stands for hydrogen atom, hydroxymethyl, NHR3, SO2NR4R4' or nitro, wherein R3 is hydrogen atom, methyl, SO2R5, formyl or CONHR6', with R5 being lower alkyl, benzyl or NR4R4' and R4 and R4' may be identical with or different from each other and stand each for hydrogen atom, lower alkyl or benzyl and R6' has the meaning as given above".

Also preferred examples of the compound represented by the general formula (I) or the salt thereof according to the present invention are those in which the combination of the substituent groups in the general formula (I) is such that "R represents hydrogen atom, R1 stands for hydrogen atom, fluorine atom, chlorine atom, hydroxy or benzyloxy and R2 stands for hydroxymethyl, NHR3, SO2NR4R4' or nitro, wherein R3 is hydrogen atom, methyl, SO2R5, formyl or CONHR6' and either one of R4 and R4 is hydrogen atom and other one is hydrogen atom, lower alkyl or benzyl, with R5 being lower alkyl, benzyl or dimethylamino and R6' being the same as given above".

Also preferred examples of the compound represented by the general formula (I) or the salt thereof according to the present invention are those in which the combination of the substituent groups in the general formula (I) is such that "R represents hydrogen atom, R1 stands for hydrogen atom, halogen atom, hydroxy or benzyloxy and R2 stands for hydroxymethyl, NHR3, SO2NR4R4' or nitro, wherein R3 is hydrogen atom, methyl, SO2R5, formyl or CONHR6', with R5 being lower alkyl, benzyl or NR4R4' and R4 and R4' may be identical with or different from each other and stand each for hydrogen atom, lower alkyl or benzyl and R6' has the meaning as given above".

Also preferred examples of the compound represented by the general formula (I) or the salt thereof according to the present invention are those in which the combination of the substituent groups in the general formula (I) is such that "R represents hydrogen atom, R1 stands for hydrogen atom, fluorine atom, chlorine atom, hydroxy or benzyloxy and R2 stands for hydroxymethyl, NHR3, SO2NR4R4' or nitro, wherein R3 is hydrogen atom, methyl, SO2R5, formyl or CONHR6' and either one of R4 and R4' is hydrogen atom and the other one is hydrogen atom, lower alkyl or benzyl, with R5 being lower alkyl, benzyl or dimethylamino and R6' being the same as given above".

Also preferred examples of the compound represented by the general formula (I) or the salt thereof according to the present invention are those in which the combination of the substituent groups in the general formula (I) is such that "R and R1 represent each hydrogen atom and R2 stands for hydroxymethyl, NHR3 or SO2NR4R4', wherein R3 is hydrogen atom, methyl, SO2R5, formyl or CONHR6' with R5 being lower alkyl, benzyl or NR4R4' and R4 and R4' may be identical with or different from each other and stand each for hydrogen atom, lower alkyl or benzyl and R6' being the same as given above".

Also preferred examples of the compound represented by the general formula (I) or the salt thereof according to the present invention are those in which the combination of the substituent groups in the general formula (I) is such that "R and R1 represent each hydrogen atom and R2 stands for hydroxymethyl, NHR3 or SO2NR4R4, wherein R3 is hydrogen atom, methyl, SO2R5, formyl or CONHR6' and any one of R4 and R4' stands each for hydrogen atom, and the other represents hydrogen atom, lower alkyl or benzyl and R5 stands for hydrogen atom, benzyl or dimethylamino, and R6' being the same as given above".

Also preferred examples of the compound represented by the general formula (I) or the salt thereof according to the present invention are those in which the combination of the substituent groups in the general formula (I) is such that "R represents hydrogen atom, R1 stands for halogen atom or hydroxy and R2 stands for NHSO2R5 or SO2NR4R4', wherein R5 is lower alkyl, benzyl or NR4R4' and R4 and R4' may be identical with or different from each other and stand each for hydrogen atom, lower alkyl or benzyl".

Also preferred examples of the compound represented by the general formula (I) or the salt thereof according to the present invention are those in which the combination of the substituent groups in the general formula (I) is such that "R represents hydrogen atom, R1 stands for fluorine atom, chlorine atom or hydroxy and R2 stands for NHSO2R5 or SO2NR4R4' , wherein either one of R4 and R4' is hydrogen atom and the other one is hydrogen atom, lower alkyl or benzyl and R5 is lower alkyl, benzyl or dimethylamino".

Also preferred examples of the compound represented by the general formula (I) or the salt thereof according to the present invention are those in which the combination of the substituent groups in the general formula (I) is such that "R and R2 represent each hydrogen atom and R1 stands for hydrogen atom, halogen atom or hydroxy".

Also preferred examples of the compound represented by the general formula (I) or the salt thereof according to the present invention are those in which the combination of the substituent groups in the general formula (I) is such that "R and R2 represent each hydrogen atom and R1 stands for hydrogen atom, fluorine atom, chlorine atom or hydroxy".

Also preferred examples of the compound represented by the general formula (I) or the salt thereof according to the present invention are those in which the combination of the substituent groups in the general formula (I) is such that "R represents hydrogen atom, R1 stands for hydrogen atom, halogen atom, hydroxy, amino or hydroxymethyl and R2 stands for NHR3 or SO2NR4R4', wherein R3 is SO2R5, with R5 being lower alkyl, benzyl or NR4R4', and R4 and R4' may be identical with or different from each other and stand each for hydrogen atom, lower alkyl or benzyl".

Also preferred examples of the compound represented by the general formula (I) or the salt thereof according to the present invention are those in which the combination of the substituent groups in the general formula (I) is such that "R represents methyl, R1 stands for hydrogen atom, halogen atom, hydroxy, benzyloxy, amino or hydroxymethyl and R2 stands for hydrogen atom, hydroxymethyl, NHR3, SO2NR4R4' or nitro, wherein R3 is hydrogen atom, methyl, SO2R5, formyl or CONHR6', with R5 being lower alkyl, benzyl or NR4R4', and R4 and R4' may be identical with or different from each other and stand each for hydrogen atom, lower alkyl or benzyl and R6' has the meaning as given above".

Also preferred examples of the compound represented by the general formula (I) or the salt thereof according to the present invention are those in which the combination of the substituent groups in the general formula (I) is such that "R represents methyl, R1 stands for hydrogen atom, fluorine atom, chlorine atom, hydroxy or benzyloxy and R2 stands for hydrogen atom, hydroxymethyl, NHR3, SO2NR4R4 or nitro, wherein R3 is hydrogen atom, methyl, SO2R5, formyl or CONHR6', with R5 being lower alkyl, benzyl or NR4R4', and either one of R4 and R4 is hydrogen atom, lower alkyl or benzyl and R6 has the meaning as given above".

Also preferred examples of the compound represented by the general formula (I) or the salt thereof according to the present invention are those in which the combination of the substituent groups in the general formula (I) is such that "R represents methyl, R1 stands for hydrogen atom, halogen atom, hydroxy or benzyloxy and R2 stands for hydroxymethyl, NHR3, SO2NR4R4' or nitro, wherein R3 is hydrogen atom, methyl, SO2R5, formyl or CONHR6 , with R5 being lower alkyl, benzyl or NR4R4', and R4 and R4' may be identical with or different from each other and stand each for hydrogen atom, lower alkyl or benzyl and R6' has the meaning as given above".

Also preferred examples of the compound represented by the general formula (I) or the salt thereof according to the present invention are those in which the combination of the substituent groups in the general formula (I) is such that "R represents methyl, R1 stands for hydrogen atom, fluorine atom, choline atom, hydroxy or benzyloxy and R2 stands for hydroxymethyl, NHR3, SO2NR4R4' or nitro, wherein R3 is hydrogen atom, methyl, SO2R5, formyl or CONHR6', and either one of R4 and R4' is hydrogen atom, and the other is hydrogen atom, lower alkyl or benzyl and R5 being lower alkyl, benzyl or dimethylamino and R6' has the meaning as given above".

Also preferred examples of the compound represented by the general formula (I) or the salt thereof according to the present invention are those in which the combination of the substituent groups in the general formula (I) is such that "R represents methyl, R1 stands for hydrogen atom and R2 stands for hydroxymethyl, NHR3 or SO2NR4R4, wherein R3 is hydrogen atom, methyl, SO2R5, formyl or CONHR6, with R5 being lower alkyl, benzyl or NR4R4, and R4 and R4' may be identical with or different from each other and stand each for hydrogen atom, lower alkyl or benzyl and R6' has the meaning as given above".

Also preferred examples of the compound represented by the general formula (I) or the salt thereof according to the present invention are those in which the combination of the substituent groups in the general formula (I) is such that "R represents methyl, R1 stands for hydrogen atom and R2 stands for hydroxymethyl, NHR3 or SO2NR4R4', wherein R3 is hydrogen atom, methyl, SO2R5, formyl or CONHR6 , and either one of R4 and R4' is hydrogen atom and the other one is hydrogen atom, lower alkyl or benzyl and R5 is lower alkyl, benzyl or dimethylamino, and R6' has the meaning as given above".

Also preferred examples of the compound represented by the general formula (I) or the salt thereof according to the present invention are those in which the combination of the substituent groups in the general formula (I) is such that "R represents methyl, R1 stands for halogen atom or hydroxy and R2 stands for NHSO2R5 or SO2NR4R4', wherein R5 is lower alkyl, benzyl or NR4R4, and R4 and R4' may be identical with or different from each other and stand each for hydrogen atom, lower alkyl or benzyl".

Also preferred examples of the compound represented by the general formula (I) or the salt thereof according to the present invention are those in which the combination of the substituent groups in the general formula (I) is such that "R represents methyl, R1 stands for fluoine atom, choline atom or hydroxy and R2 stands for NHSO2R5 or SO2NR4R4' wherein either one of R4 and R4' is hydrogen atom and the other one is hydrogen atom, lower alkyl or benzyl and R5 is lower alkyl, benzyl or dimethylamino.

Also preferred examples of the compound represented by the general formula (I) or the salt thereof according to the present invention are those in which the combination of the substituent groups in the general formula (I) is such that "R represents methyl, R1 stands for hydrogen atom, halogen atom or hydroxy and R2 stands for hydrogen atom".

Also preferred examples of the compound represented by the general formula (I) or the salt thereof according to the present invention are those in which the combination of the substituent groups in the general formula (I) is such that "R represents methyl, R1 stands for hydrogen atom, fluorine atom, choline atom or hydroxy and R2 stands for hydrogen atom".

Also preferred examples of the compound represented by the general formula (I) or the salt thereof according to the present invention are those in which the combination of the substituent groups in the general formula (I) is such that "R represents methyl, R1 stands for hydrogen atom, halogen atom, hydroxy, amino or hydroxymethyl and R2 stands for NHR3 or SO2NR4R4', wherein R3 is SO2R5, with R5 being lower alkyl, benzyl or NR4R4', and R4 and R4' may be identical with or different from each other and stand each for hydrogen atom, lower alkyl or benzyl".

Concrete examples of the compound represented by the general formula (I) according to the present invention include (R)-N-[5-[2-[2-(5,6,7,8-tetrahydro-9H-carbazol-2-yloxy) ethylamino]-1-hydroxyethyl]-2-hydroxyphenyl] methanesulfonamide, (S)-N-[5-[2-[2-(5,6,7,8-tetrahydro-9H-carbazol-2-yloxy) ethylamino]-1-hydroxyethyl]-2-hydroxyphenyl] methanesulfonamide, N-[5-[2-[2-(5,6,7,8-tetrahydro-9H-carbazol-2-yloxy) ethylamino]-1-hydroxyethyl]-2-hydroxyphenyl] methanesulfonamide;

N-[5-[2-[2-(3-hydroxy-5,6,7,8-tetrahydro-9H-carbazol-2-yloxy)ethylamino]-1-hydroxyethyl]-2-hydroxyphenyl] methanesulfonamide;

N-[5-[2-[2-(3-amino-5,6,7,8-tetrahydro-9H-carbazol-2-yloxy)ethylamino]-1-hydroxyethyl]-2-hydroxyphenyl]methanesulfonamide;

N-[5-[2-[2-(6-amino-5,6,7,8-tetrahydro-9H-carbazol-2-yloxy)ethylamino]-1-hydroxyethyl]-2-hydroxyphenyl]methanesulfonamide;

N-[5-[2-[2-(6-hydroxy-5,6,7,8-tetrahydro-9H-carbazol-2-yloxy)ethylamino]-1-hydroxyethyl]-2-hydroxyphenyl]methanesulfonamide;

(R)-N-[3-[2-[2-(5,6,7,8-tetrahydro-9H-carbazol-2-yloxy)ethylamino]-1-hydroxyethyl]phenyl]methanesulfonamide;

(S)-N-[3-[2-[2-(5,6,7,8-tetrahydro-9H-carbazol-2-yloxy)ethylamino]-1-hydroxyethyl]phenyl]methanesulfonamide;

N-[3-[2-[2-(5,6,7,8-tetrahydro-9H-carbazol-2-yloxy)ethylamino]-1-hydroxyethyl]phenyl]methanesulfonamide;

N-methyl-3-[2-[2-(5,6,7,8-tetrahydro-9H-carbazol-2-yloxy)ethylamino]-1-hydroxyethyl]benzensulfonamide;

N-methyl-[5-[2-[2-(5,6,7,8-tetrahydro-9H-carbazol-2-yloxy)ethylamino]-1-hydroxyethyl]-2-hydroxy]benzensulfonamide;

N-methyl-[5-[2-[2-(5,6,7,8-tetrahydro-9H-carbazol-2-yloxy)ethylamino]-1-hydroxyethyl]-2-chloro]benzensulfonamide;

(R)-N-methyl-[5-[2-[2-(5,6,7,8-tetrahydro-9H-carbazol-2-yloxy)ethylamino]-1-hydroxyethyl]-2-chloro]benzensulfonamide;

(R)-N-[5-[2-[2-(6,7,8,9-tetrahydrodibenzofuran-3-yloxy)ethylamino]-1-hydroxyethyl]-2-hydroxyphenyl]methanesulfonamide;

(S)-N-[5-[2-[2-(6,7,8,9-tetrahydrodibenzofuran-3-yloxy)ethylamino]-1-hydroxyethyl]-2-hydroxyphenyl]methanesulfonamide;

N-[5-[2-[2-(6,7,8,9-tetrahydrodibenzofuran-3-yloxy)ethylamino]-1-hydroxyethyl]-2-hydroxyphenyl]methanesulfonamide;

N-[5-[2-[2-(5,6,7,8-tetrahydro-9H-carbazol-2-yloxy)ethylamino]-1-hydroxyethyl]-2-(benzyloxy)phenyl]methanesulfonamide;

N-[5-[2-[2-(5,6,7,8-tetrahydro-9H-carbazol-2-yloxy)ethylamino]-1-hydroxyethyl]-2-chlorophenyl]methanesulfonamide;

N-[5-[2-[2-(5,6,7,8-tetrahydro-9H-carbazol-2-yloxy)ethylamino]-1-hydroxyethyl]-2-fluorophenyl]methanesulfonamide;

N-[3-[2-[2-(6,7,8,9-tetrahydrodibenzofuran-3-yloxy)ethylamino]-1-hydroxyethyl]phenyl]methanesulfonamide;

N-[5-[2-[2-(5,6,7,8-tetrahydro-9H-carbazol-2-yloxy)ethylamino]-1-hydroxyethyl]-2-hydroxyphenyl]formamide;

N-[3-[2-[2-(5,6,7,8-tetrahydro-9H-carbazol-2-yloxy)ethylamino]-1-hydroxyethyl]phenyl]formamide;

N-[3-[2-[1-(5,6,7,8-tetrahydro-9H-carbazol-2-yloxy)propane-2R-yl]amino]-1-hydroxyethyl]phenyl]methanesulfonamide;

2-[N-[2-(5,6,7,8-tetrahydro-9H-carbazol-2-yloxy)ethyl]amino]-1-(4-hydroxy-3-nitrophenyl)ethanol;

2-[N-[2-(5,6,7,8-tetrahydro-9H-carbazol-2-yloxy)ethyl]amino]-1-(3-amino-4-hydroxyphenyl)ethanol;

N-[5-[2-[2-(5,6,7,8-tetrahydro-9H-carbazol-2-yloxy)ethylamino]-1-hydroxyethyl]-2-hydroxyphenyl]urea;

N'-[5-[2-[2-(5,6,7,8-tetrahydro-9H-carbazol-2-yloxy)ethylamino]-1-hydroxyethyl]-2-(benzyloxy)phenyl]-N,N-dimethylsulfamide;

N'-[5-[2-[2-(5,6,7,8-tetrahydro-9H-carbazol-2-yloxy)ethylamino]-1-hydroxyethyl]-2-hydroxyphenyl]-N,N-dimethylsulfamide;

2-[N-[2-(5,6,7,8-tetrahydro-9H-carbazol-2-yloxy)ethyl]amino]-1-[3-(methylamino)-4-(benzyloxy)phenyl]ethanol;

2-[N-[2-(5,6,7,8-tetrahydro-9H-carbazol-2-yloxy)ethyl]amino]-1-[3-(methylamino)-4-hydroxyphenyl]ethanol;

N-[5-[2-[2-(5,6,7,8-tetrahydro-9H-carbazol-2-yloxy)ethylamino]-1-hydroxyethyl]-2-hydroxyphenyl]-2-propanesulfonamide;

2-N-[2-(5,6,7,8-tetrahydro-9H-carbazol-2-yloxy)ethyl]amino]-1-(3-nitrophenyl)ethanol;

N'-[3-[2-[2-(5,6,7,8-tetrahydro-9H-carbazol-2-yloxy)ethylamino -1-hydroxyethyl]phenyl]-N,N-dimethylsulfamide;

2-[N-[2-(5,6,7,8-tetrahydro-9H-carbazol-2-yloxy)ethyl]amino]-1-(3-aminophenyl)ethanol;

2-[N-[2-(5,6,7,8-tetrahydro-9H-carbazol-2-yloxy)ethyl]amino]-1-(3-hydroxymethyl)-4-hydroxyphenyl]ethanol;

N-[5-[2-[2-(5,6,7,8-tetrahydro-9H-carbazol-2-yloxy)ethylamino]-1-hydroxyethyl]-3-hydroxyphenyl]methanesulfonamide;

N-[3-[2-[2-(5,6,7,8-tetrahydro-9H-carbazol-2-yloxy)ethylamino]-1-hydroxyethyl]-2-hydroxyphenyl]methanesulfonamide;

N-[3-[2-[2-(5,6,7,8-tetrahydro-9H-carbazol-2-yloxy)ethylamino]-1-hydroxyethyl]-4-hydroxyphenyl]methanesulfonamide;

(R)-N'-[5-[2-[2-(5,6,7,8-tetrahydro-9H-carbazol-2-yloxy)ethylamino]-1-hydroxyethyl]-2-hydroxyphenyl]-N,N-dimethylsulfamide;

(S)-N'-[5-[2-[2-(5,6,7,8-tetrahydro-9H-carbazol-2-yloxy)ethylamino]-1-hydroxyethyl]-2-hydroxyphenyl]-N,N-dimethylsulfamide;

N-[3-[2-[2-(6-acetylamino-5,6,7,8-tetrahydro-9H-carbazol-2-yloxy)ethylamino]-1-hydroxyethyl]phenyl]methanesulfonamide;

N-[5-[2-[2-(6-acetylamino-5,6,7,8-tetrahydro-9H-carbazol-2-yloxy)ethylamino]-1-hydroxyethyl]-2-hydroxyphenyl]methanesulfonamide;

(R)-N-[5-[2-[2-(5,6,7,8-tetrahydro-9H-carbazol-2-yloxy)ethylamino]-1-hydroxyethyl]-2-fluorophenyl]methanesulfonamide;

(S)-N-[5-[2-[2-(5,6,7,8-tetrahydro-9H-carbazol-2-yloxy)ethylamino]-1-hydroxyethyl]-2-fluorophenyl]methanesulfonamide;

(R)-N-[5-[2-[2-(5,6,7,8-tetrahydro-9H-carbazol-2-yloxy)ethylamino]-1-hydroxyethyl]-2-chlorophenyl]methanesulfonamide;

(S)-N-[5-[2-[2-(5,6,7,8-tetrahydro-9H-carbazol-2-yloxy)ethylamino]-1-hydroxyethyl]-2-chlorophenyl]methanesulfonamide;

N,N-dimethyl-[5-[2-[2-(5,6,7,8-tetrahydro-9H-carbazol-2-yloxy)ethylamino]-1-hydroxyethyl]-2-hydroxy]benzenesulfonamide;

N-[5-[2-[2-(5,6,7,8-tetrahydro-9H-carbazol-2-yloxy)ethylamino]-1-hydroxyethyl]-2-iodophenyl]methanesulfonamide;

N'-[5-[2-[2-(5,6,7,8-tetrahydro-9H-carbazol-2-yloxy)ethylamino]-1-hydroxyethyl]-2-fluorophenyl]-N,N-dimethylsulfamide;

N'-[5-[2-[2-(5,6,7,8-tetrahydro-9H-carbazol-2-yloxy)ethylamino]-1-hydroxyethyl]-2-chlorophenyl]-N,N-dimethylsulfamide;

(R)-N-methyl-[5-[2-[2-(5,6,7,8-tetrahydro-9H-carbazol-2-yloxy)ethylamino]-1-hydroxyethyl]-2-hydroxy]benzenesulfonamide;

(R)-N-[5-[2-[2-(5,6,7,8-tetrahydro-9H-carbazol-2-yloxy) ethylamino]-1-hydroxyethyl]-2-(hydroxymethyl)phenyl] methanesulfonamide;

(R)-N-[3-[2-[2-(6,7,8,9-tetrahydrodibenzofuran-3-yloxy) ethylamino]-1-hydroxyethyl]phenyl] methanesulfonamide;

N'-[5-[2-[2-(6,7,8,9-tetrahydrodibenzofuran-3-yloxy) ethylamino]-1-hydroxyethyl]-2-hydroxyphenyl]-N,N-dimethylsulfamide;

(R)-N'-[5-[2-[2-(6,7,8,9-tetrahydrodibenzofuran-3-yloxy) ethylamino]-1-hydroxyethyl]-2-hydroxyphenyl]-N,N-dimethylsulfamide;

(S)-N'-[5-[2-[2-(6,7,8,9-tetrahydrodibenzofuran-3-yloxy) ethylamino]-1-hydroxyethyl]-2-hydroxyphenyl]-N,N-dimethylsulfamide;

N-[5-[2-[2-(6,7,8,9-tetrahydrodibenzofuran-3-yloxy) ethylamino]-1-hydroxyethyl]-2-fluorophenyl] methanesulfonamide;

N-[5-[2-[2-(6,7,8,9-tetrahydrodibenzofuran-3-yloxy) ethylamino]-1-hydroxyethyl]-2-chlorophenyl] methanesulfonamide;

N-[5-[2-[2-(6,7,8,9-tetrahydrodibenzothiophen-3-yloxy) ethylamino]-1-hydroxyethyl]-2-hydroxyphenyl] methanesulfonamide;

N'-[5-[2-[2-(6,7,8,9-tetrahydrodibenzothiophen-3-yloxy) ethylamino]-1-hydroxyethyl]-2-hydroxyphenyl]-N,N-dimethylsulfamide;

N-[3-[2-[2-(6,7,8,9-tetrahydrodibenzothiophen-3-yloxy) ethylamino]-1-hydroxyethyl]phenyl] methanesulfonamide;

(R)-N-[5-[2-[2-(6,7,8,9-tetrahydrodibenzothiophen-3-yloxy)ethylamino]-1-hydroxyethyl]-2-hydroxyphenyl] methanesulfonamide;

N-[5-[2-[2-(6,7,8,9-tetrahydrodibenzothiophen-3-yloxy) ethylamino]-1-hydroxyethyl]-2-fluorophenyl] methanesulfonamnide;

N-[5-[2-[2-(6,7,8,9-tetrahydrodibenzothiophen-3-yloxy) ethylamino]-1-hydroxyethyl]-2-chlorophenyl] methanesulfonamide;

N'-[5-[2-[2-(5,6,7,8-tetrahydro-9H-carbazol-2-yloxy) ethylamino]-1-hydroxyethyl]-2-aminophenyl]-N-benzyl-N-methylsulfamide;

N-[5-[2-[2-(5,6,7,8-tetrahydro-9H-carbazol-2-yloxy) ethylamino]-1-hydroxyethyl]-2-aminophenyl] methanesulfonamide;

N-[5-[2-[2-(5,6,7,8-tetrahydro-9H-carbazol-2-yloxy) ethylamino]-1-hydroxyethyl]-2-(hydroxymethyl)phenyl] methanesulfonamide;

N-[5-[2-[2-(5,6,7,8-tetrahydro-9H-carbazol-2-yloxy) ethylamino]-1-hydroxyethyl]-2-brmophenyl] methanesulfonamide;

(R)-N-[5-[2-[2-(5,6,7,8-tetrahydro-9H-carbazol-2-yloxy) ethylamino]-1-hydroxyethyl]-2-bromophenyl] methanesulfonamide:

N'-[5-[2-[2-(5,6,7,8-tetrahydro-9H-carbazol-2-yloxy) ethylamino]-1-hydroxyethyl]-2-hydroxyphenyl]-N-benzyl-N-methylsulfamide;

N'-[5-[2-[2-(5,6,7,8-tetrahydro-9H-carbazol-2-yloxy) ethylamino]-1-hydroxyethyl]-2-hydroxyphenyl]-N,N-diethylsulfamide;

(R)-N-[5-[2-[2-(5,6,7,8,9,10-hexahydro-cyclohepta[b] indol-2-yloxy)ethylamino]-1-hydroxyethyl]-2-hydroxyphenyl]-methanesulfonamide;

(S)-N-[5-[2-[2-(5,6,7,8,9,10-hexahydro-cyclohepta[b]indol-2-yloxy)ethylamino]-1-hydroxyethyl]-2-hydroxyphenyl] methanesulfonamide;

N-[5-[2-[2-(5,6,7,8,9,10-hexahydro-cyclohepta[b]indol-2-yloxy)ethylamino]-1-hydroxyethyl]-2-hydroxyphenyl] methanesulfonamide;

(R)-N-[3-[2-[2-(5,6,7,8,9,10-hexahydro-cyclohepta[b]indol-2-yloxy)ethylamino]-1-hydroxyethyl]phenyl] methanesulfonamide;

N-[3-[2-[2-(5,6,7,8,9,10-hexahydro-cyclohepta[b]indol-2-yloxy)ethylamino]-1-hydroxyethyl]phenyl] methanesulfonamide;

(R)-N-methyl-[5-[2-[2-(5,6,7,8,9,10-hexahydro-cyclohepta[b]indol-2-yloxy)ethylamino]-1-hydroxyethyl]-2-hydroxy]benzenesulfonamide;

(R)-N-methyl-[5-[2-[2-(5,6,7,8,9,10-hexahydro-cyclohepta[b]indol-2-yloxy)ethylamino]-1-hydroxyethyl]-2-chloro] benzenesulfonamide;

N'-[5-[2-[2-(5,6,7,8,9,10-hexahydro-cyclohepta[b]indol-2-yloxy)ethylamino]-1-hydroxyethyl]-2-hydroxyphenyl]-N,N-dimethylsulfamide;

(R)-N'-[5-[2-[2-(5,6,7,8,9,10-hexahydro-cyclohepta[b] indol-2-yloxy)ethylamino]-1-hydroxyethyl]-2-hydroxyphenyl]-N,N-dimethylsulfamide;

(R)-N-[5-[2-[2-(5,6,7,8,9,10-hexahydro-cyclohepta[b] indol-2-yloxy)ethylamino]-1-hydroxyethyl]-2-bromophenyl]methanesulfonamide;

(R)-N-[5-[2-[2-(5,6,7,8,9,10-hexahydro-cyclohepta[b] indol-2-yloxy)ethylamino]-1-hydroxyethyl]-2-chlorophenyl]methanesulfonamide;

(R)-N-[5-[2-[2-(5,6,7,8,9,10-hexahydro-cyclohepta[b] indol-2-yloxy)ethylamino]-1-hydroxyethyl]-2-fluorophenyl]methanesulfonamide;

The following are concrete examples of the compound in which both R1 and R2 are hydrogen atoms. 2-[N-[2-(5,6,7,8-tetrahydro-9H-carbazol-2-yloxy)ethyl]amino]-1-(4-hydroxyphenyl)ethanol; 2-[N-[2-(5,6,7,8-tetrahydro-9H-carbazole-2-yloxy)ethyl]amino]-1-(2-fluorophenyl) ethanol; 2-[N-[2-(5,6,7,8-tetrahydro-9H-carbazol-2-yloxy)ethyl]amino]-1-(2-hydroxyphenyl)ethanol;

(R,R)-[2-[N-[1-(5,6,7,8-tetrahydro-9H-carbazol-2-yloxy) propane -2-yl]amino]-1-phenyl]ethanol;

[2-[N-[2-(5,6,7,8-tetrahydro-9H-carbazol-2-yloxy)ethyl] amino]-1-phenyl]ethanol;

(R)-[2-[N-[2-(5,6,7,8-tetrahydro-9H-carbazol-2-yloxy) ethyl]amino]-1-phenyl]ethanol;

(S)-[2-[N-[2-(5,6,7,8-tetrahydro-9H-carbazol-2-yloxy) ethyl]amino]-1-phenyl]ethanol; [2-[N-[2-(3-acetylamino-5,6,7,8-tetrahydro-9H-carbazol-2-yloxy) ethyl]amino]-1-phenyl]ethanol; [2-[N-[2-(3-amino-5,6,7,8-tetrahydro-9H-carbazol-2-yloxy)ethyl]amino]-1-phenyl]ethanol; [2-[N-[2-(3-hydroxy-5,6,7,8-tetrahydro-9H-carbazol-2-yloxy)ethyl]amino]-1-phenyl]ethanol; [2-[N-[2-(6-amino-5,6,7,8-tetrahydro-9H-carbazol-2-yloxy)ethyl] amino]-1-phenyl]ethanol; [2-[N-[2-(6-acetylamino-5,6,7,8-tetrahydro-9H-carbazol-2-yloxy) ethyl]amino]-1-phenyl]ethanol; [2-[N-[1-(5,6,7,8-tetrahydro-9H-carbazol-2-yloxy)propane-2-yl]amino]-1-phenyl]ethanol; [2-[N-[2-(6,7,8,9-tetrahydrodibenzofuran-3-yloxy)ethyl] amino]-1-phenyl]ethanol;

Examples of the compounds in which R stands for methyl include the following.

N-[5-[2-[2-(5,6,7,8-tetrahydro-9H-carbazol-2-yloxy) ethylamino]-1-methoxyethyl]-2-hydroxyphenyl] methanesulfonamide;

N-[5-[2-[2-(6,7,8,9-tetrahydrodibenzothiophen-3-yloxy) ethylamino]-1-methoxyethyl]-2-hydroxyphenyl] methanesulfonamide;

N-[5-[2-[2-(5,6,7,8-tetrahydro-9H-carbazol-2-yloxy) ethylamino]-1-methoxyethyl]-2-aminophenyl] methanesulfonamide and The compound represented by the general formula (I) can be produced, for example, by the following methods.

(Production process A)

A compound represented by the general formula (II)

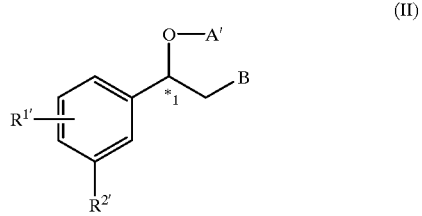

(II)

[in which R1' represents hydrogen atom, halogen atom, a protected hydroxy group protected by a protecting group A, a protcted amino group protected by acetyl group or a protected hydroxymethyl group protected by acetyl group, R2' stands for hydrogen atom, a protected hydroxymethyl group in which the hydroxy group is protected by a protecting group A''', NHR3', SO2NR4R4' or nitro, wherein R3' represents a protecting group for the amino group, methyl, SO2R5, formyl or CONHR6', with R5 being lower alkyl, benzyl or NR4R4' and R6' being hydrogen atom or lower alkyl, R4 and R4' may be identical with or different from each other and stand each for hydrogen atom, lower alkyl or benzyl, R6 denotes hydrogen atom or lower alkyl, A' represents a protecting group for the hydroxy group, B is bromine atom or iodine atom and *1 indicates an asymmetric carbon atom] is reacted with a compound represented by the general formula (III)

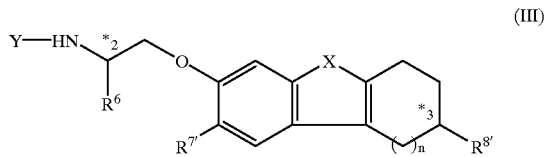

(III)

[wherein Y represents hydrogen atom, R6 is hydrogen atom or lower alkyl, n is 1 or 2, X is secondary nitrogen atom, oxygen atom or sulfur atom and, in case that n is 1, either one of R7' or R8' is hydrogen atom acetylamino or a protected hydroxyl group protected by a protecting group A'', or, in case that n is 2, R8' is hydrogen atom and R7' stands for hydrogen atom, acetylamino or a protected hydroxy group protected by a protecting group A'', and *2 and *3 indicate asymmetric carbon atom, when R6 and R8' are not hydrogen atom], and the protecting groups A (proviso that in case that R1 is benzyloxy and the protecting group A isbenzyl, the protecting group A is not deprotected), A', A'', A''' and the protecting group for amino group in R3' (proviso that if is exist), or the protecting acetyl group in R1' are deprotected to obtain the compound represented by the general formula (I), [wherein R represents hydrogen atom, R1 stands for hydrogen atom, halogen atom, hydroxy, benzyloxy, amino or hydroxymethyl, R2 stands for hydrogen atom, hydroxymethyl, NHR3', SO2NR4R4' or nitro, proviso that R3' is hydrogen atom, methyl, SO2R5, formyl or CONHR6', and R5 is lower alkyl, benzyl or NR4R4' and R4and R4' may be identical with or different from each other and are hydrogen atom, lower alkyl or benzyl group. R6' is represents hydrogen atom for lower alkyl.

As the protecting groups for protecting the hydroxy groups, there is no special limitaion so long as ordinary use is permitted and there may usually be used as a protecting group which can be deprotected easily and selectively, for example, benzyl or t-butyl-dimethylsilyl for the protecting group A, triethylsilyl for the protecting groups A' and A''' and methyl or benzyl for the protecting group A''. For introducing a protecting group into the compound to be protected, known practice is employed and, for exapmle, a method is used for protecting the compound by introducing therein benzyl group, in which the compound is reached with 1 or 2 excess molar benzyl bromide and 1.1 excess molar sodium iodide at room temperature in a reaction solvent, such as dimetyhylformamide, in the presence of potassium carbonate. For protecting the compound by introducing therein triethylsilyl group, the compound is reacted with 1.2–2 molar excess silylating agent, such as triethylsilyl chloride, at a temperature in the range of 0 to 30° C. in the reaction solvent, such as pyridine, for 1–3 hours.

As the protecting group for protecting the amino group in the substituent R3' there is no special limitation so long as ordinary use as a protecting group for protecting aniline is permitted and acetyl group may usually be preferred therefor. For acethylation, a reaction with acetic anhydride in a reaction solvent, such as pyridine, may be exemplified.

The coupling reaction of the compound represented by the general formula (II) with the amine represented by the general formula (III) may be realized using 1 to 1.5 moles of the amine of the general formula (III) per 1 mole of the halide of the general formula (II) in a polar solvent, such as dimethylformamide, dimethylacetamide or dimethylsulfoxide, in the presence of a proton capturing agent, for example, an amine, such as triethylamine or diisopropylethylamine, at a temperature in the range from room temperature to 90° C., preferably by heating at 60° C., 5–10 hours.

Deprotection of the resulting product may be effected either in succession or simultaneously, while deprotection in a successive order of A'', A', A''', the protecting agent for the amino group in R3 and at last A may be preferred. The deprotection of benzyl group for A and A'' is performed by catalytic hydrogenation in a solvent, such as methanol, using a catalyst, such as palladium or nickel. In the case where the substituent R1 in the general formula (I) is benzyloxy, there is no need of elimination of benzyl group as the protecting group A. The deprotection of benzyl or methyl as the protecting groups A and A'' may be realized by treating the product with a Lewis acid, such as boron tribromide, in a solvent, such as methylene chloride. The deprotection of acetyl-protected hydroxy group in the substituent R1' may be realized by a known procedure of hydrolysis of ester. Concretely, it may be performed in an alcohol using an alkali at room temperature or by heating under reflux of the solvent. The deprotection of triethylsilyl as the protecting group A' or A''' may be realized by treating the product by adding thereto acetic acid and 3–5 molar excess tetrabutylammonium fluoride in a solvent of tetrahydrofuran at room temperature for 30 minutes–5 hours. The deprotection of the protecting group, such as acetyl, for the amino group in R3' or of the acetyl-protected amino group in R1' may be realized either by treating the product with hydrochloric acid at room temperature or by heating in a solvent, such as water or methanol, with an alkali.

The compound represented by the general formula (II) can be obtained by subjecting a compound represented by the following general formula (V)

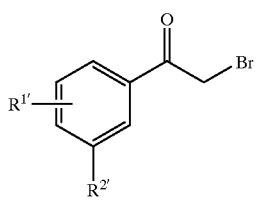
(V)

in which R1' and R2' have the same meanings as given previously, to a reduction in the manner as described below, and replacing the bromide, if the contemplated substituent group B in the general formula (II) is iodine, to iodide, followed by protection of the hydroxy group.

The reduction of the compound represented by the general formula (V) may be attained by using reducing agent, such as a borane, when the steric configuration (*1) of the hydroxy group of the compound represented by the general formula (II) is racemic.

In case where either R- or S-optical isomer is to be obtained as to the *1 structure in the general formula (II), the reduction can be attained by having resort to employment of a chiral assistant, such as given by the following general formula (VI).

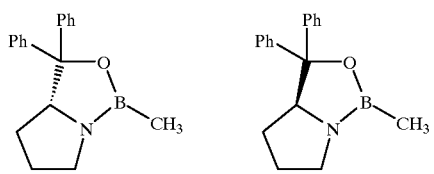
(VI)

Thus, the reduction of the compound represented by the general formula (V) is effected using a borane in the presence of the above-mentioned chiral assistant. The reduction may preferably be performed in a solvent, such as tetrahydrofuran. The preparation of such a chiral assistant and reaction therewith may be carried out in accordance with the teachings in the literature [E. J. Corey et al, J. Org. Chem., Vol. 56, 442, (1991)].

After the reduction of the compound represented by the general formula (V), the bromide thereof is, if necessary, replaced with iodide by, for example, treating the reduced compound with 3–10 excess molar amount of an iodizing agent, such as sodium iodide, in a solvent, such as acetone, with heating under reflux for 1–3 hours.

Then the compound (II) can be obtained by protecting the hydroxyl group with triethylsilyl group according to the protective method for hydroxy group as above described.

The compound represented by the general formula (V) is known and can be synthesized by methods given in literatures, for example, A. A. Larsen et al. J. Med. Chem., 10, 462 (1967); or C. Kaiser et al. J. Med. Chem. 17, 49 (1974).

The compound represented by the general formula (III) can be obtained by reacting a compound represented by the general formula (VII)

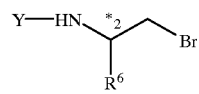
(VII)

in which Y denotes a protecting group for the amino group, R6 and *2 have the same meanings as those given previously, with a compound represented by the general formula (VIII)

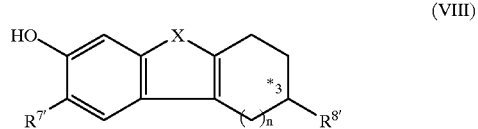
(VIII)

in which n, X, R7' and R8' have the same meanings as those given previously. As the protecting group Y for protecting the amino acid group, there is no special limitation so long as a usual use is permitted and there may be exemplified one which can usually be deprotected easily, for example, benzyloxycarbonyl, a substituted benzyloxycarbonyl, t-butoxycarbonyl, acetyl or trifluoroacetyl.

The reaction of the compound represented by the general formula (VII) with the compound represented by the general formula (VIII) can be realized, for example, in an organic solvent usually in the presence of a base at a temperature from room temperature to the reflux temperature of the solvent employed. As the solvent, there may be employed, for example, dimethylformamide, dimethylacetamide, acetonitrile, diglym and tetrahydrofuran. As the base, there may be employed, for example, potassium carbonate, sodium carbonate, sodium hydroxide, potassium hydroxide, triethylamine, pyridine, sodium hydride or sodium methoxide, in an amount of, preferably, 1–10 moles per one mole of the compound of the general formula (VIII).

The compound represented by the general formula (III) can, in particular, if the above reaction does not proceed promptly, also be synthesized in accordance with the process described in Bull. Chem. Soc. Japan, 55, 2504 (1982) or by an improvement thereof. For example, one mole of the alcohol compound is reacted with 2–5 moles of the compound represented by the general formula (VII) in a solvent, such as dimethylformamide or acetonitrile, in the presence of 5–10 moles of 40% potassium fluoride-alumina at a temperature in the range from room temperature to 90° C. In the improved process, the above reaction is realized with addition of 0.1–0.5 equivalent of potassium iodide.

Then, the protecting group Y for protecting the amino group is deprotected to obtain the amine compound represented by the general formula (III) wherein Y stands for hydrogen atom. The deprotection may be effected by a usual method, for example, by a hydrogenolysis in a solvent, such as methanol, using a catalyst, such as palladium/carbon black or by treating with hydrogen bromide/acetic acid. If the protecting group Y is acetyl or trifluoroacetyl, the deprotection may be attained by treating with an alkali in a solvent, such as methanol, to obtain the compound represented by the general formula (III) in which Y denotes hydrogen atom.

The compound represented by the general formula (VII) can be synthesized from a commercial product of an amino alcohol having the substituent R6 and a stereo structure of *2 by first protcting the amino group thereof with a protecting group Y and, then, the resulting product is subjected to bromination by a usual method. If there is an easily available amino bromo compound, the contemplated compound can be obtained by merely protecting the amino group by a protecting group Y. For example, a hydrobromide salt of a commercial 2-bromoethylamine may be reacted with benzyloxy carbonyl chloride in a solvent, such as methylenechloride, in the presence of triethylamine under cooling with ice water.

The compound (VIII), wherein R7' and R8' are hydrogenation, and n is 1, is a known compound. Namely, a compound, wherein X is secondary nitrogen atom, i.e. 2-hydroxy-5,6,7,8-tetrahydro-9H-carbazole can be produced by the process described in Japanese Patent Unexamined publ. No. Sho 61-57555. A compound, wherein X is oxygen, i.e. 3-hydroxy-6, 7, 8,9-tetrahydrobenzofuran, can be produced by the process described in DT2113455 and Erdtman, H. et al. Acta Chem. Scand. 15, 1761 (1961). Further, a compound, wherein X is sulfur atom, i.e. 3-hydroxy-6,7,8,9 -tetrahydrobenzothiophene can be produced by the process described in DT213455. When n is 2, the compounds can be produced according to the methods described in the above.

The compound (VIII), wherein n is 1, R7' is hydrogen, R8' is acetylamino or hydroxyl protected by protecting group A", and X is secondary nitrogen, can be produced according to the process described in U.S. Pat. No. 3,959,309. The compound of the above wherein X is oxygen or sulfur, can be produced using the compound (IX), which can be produced by conventional process.

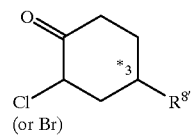

(IX)

wherein R8' and *3 have the same meaning herein above, according to the process described in the above patent specification and references.

The compound (VIII), wherein R8' is hydrogen, R7' is acetyl or hydroxyl group protected by the protecting group A", can be produced by the following process. For example, a hydroxyl group in the known 2-hydroxy-5,6,7,8-tetrahydro-9H-carbazole is benzylated, nitrogenated into the position at substituent R7', and subjected to reduction to convert into amino group. The amino group is acetylated or diazotizated, then hydroxyl group is introduced, thereafter the hydroxyl group is protected by protecting group A". Benzyl group is deprotected to obtain the compound (VIII).

For the nitration, ordinary methods given in the literatures may be employed, wherein, for example, the benzyl-protected product is subjected to nitration in acetic acid using an equivalent amount of diluted fuming nitric acid at room temperature to 60° C. Reduction of the resulting nitro group may be effected by a usually employed method, for example by hydrogen in a solvent, such as methanol, in the presence of a catalyst, such as platinum oxide at room temperature or by using hydrochloric acid with iron powder or in the presence of divalent tin at a temperature in the range from room temperature to the reflux temperature. The resultingamine may be acetylated using acetylchloride in a solvent, such as methylene chloride, at a temperature of from 0° C. to room temperature or may be converted into hydroxy group by first diazotizing it using, for example, sodium nitrite, and then, subjecting the resulting diazonium salt to a thermal decomposition in an acidic aqueous solution, followed by protection of the resulting hydroxy group with a protecting group A" by the technique for protecting hydroxy group described previously and, finally, deprotecting the benzyl gorup.

As a further alternative method, a compound represented by the general formula (IV)

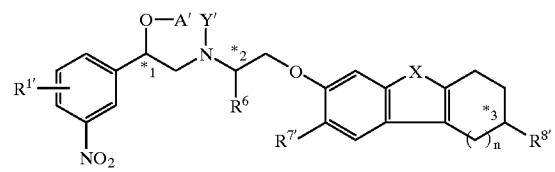

(IV)

in which Y' is hydrogen atom or a protecting group for amino group and R1', A', R6, n, X, R7', R8', *1, *2 and *3 have the same meanings as those given previously, as an important synthesis intermediate.

For producing the compound represented by the general formula (IV), the compound represented by the general formula (II) in which R2' is nitro and the compound represented by the general formula (III) in which Y stands for hydrogen atom are brought into coupling reaction and, if necessary, the amino group of the reaction product is protected. The protecting group for the amino group in the substituent group Y' of the general formula (IV) may be the same as that for the amino group in the substituent group Y explained above and the introduction and elimination thereof may also be effected in the same manner.

For producing the compound represented by the general formula (I) using the compound represented by the general formula (IV) as a synthesis intermediate, the following techniques may be exemplified:

Thus, the compound represented by the general formula (IV) is first reduced, namely, the nitro group thereof is reduced, to obtain a compound represented by the general formula (X)

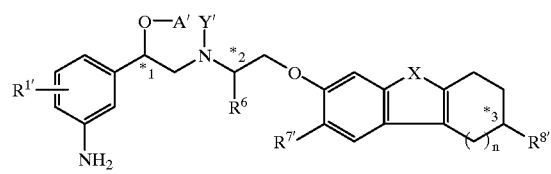

(X)

in which Y' is a protecting group for the amino group and R1, A', R6, n, X, R7', R8', *1, *2 and *3 have the same meanings as those given previously.

For the above-mentioned reduction, the amino group of the compound of the general formula (IV) may preferably have been protected by the protecting group Y' and the reduction may be performed by, for example, hydrogenating the compound in a solvent, such as methanol, in the presence of a catalyst, such as platinum oxide, or by using a system employing hydrochloric acid with iron powder or a divalent tin.

Thereafter, the resulting product is subjected to formylation, sulfonation or urearization of amine (aniline) in accordance with the requirement for providing various substituent groups for R3 by, for example, a method described in the literature, C. Kaiser et al, J. Med. Chem., 17, 49

(1974), to convert it into a compound represented by the general formula (XI)

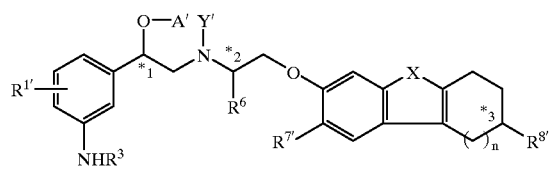

(XI)

in which Y', R1', A', R3, R6, n, X, R7', R8 , *1, *2 and *3 have the same meanings as those given previously, whereupon the existing protecting groups among A, A', A" and that for the amino group in Y' are de-protected by the method for deprotection described prviously, toproduce the compound represented by the general formula (I) in which R is hydrogen atom.

The formylation mentioned above may be effected by, for example, heating the resulting product of the general formula (X) in ethyl formate or by reacting it with a mixture of formic acid/acetic anhydride at a temperature from cooling with ice water to room temperature. The above mentioned sulfonation may be effected by, for example, reacting the resulting compound of the general formula (X) with a sulfonyl chloride substituted by a group R5 in a solvent, such as pyridine, at a temperature from cooling with ice water to room temperature. The urearization mentioned above can be attained by, for example, reacting the resulting compound of the general formula (X) with sodium cyanate (NaOCN) at room temperature or under heating at, for example, 60° C. in a mixed solvent of water/acetic acid.

Alternatively, there is a method in which a racemic compounds is obtained by a brief process step using, in the place of the compound of the general formula (II), the compound represented by the general formula (V)

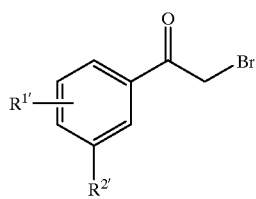

(V)

in which R1' and R2' have the same meanings as given previously.

Thus, the compound represented by the above general formula (V) is reacted with the compound represented by the general formula (III) in which Y is hydrogen atom and the resulting ketoamino compounds is, then, reduced, whereupon the protecting groups A, A", A'" and that for protecting the amino gruop in the group R3' are de-protected, with the proviso that the deprotecting of the protecting group A is unnecessary for the case where R1 stands for benzyloxy and the protecting group A is benzyl, whereby the compound represented by the general formula (I) in which R is hydrogen atom and R1, R2, R6, n, X, R7, R8 and *1, *2 and *3 have the same meanings as those given previously is obtained.

The reaction of the compound of the general formula (V) with the compound of the general formula (III) can be attained by the method disclosed in the literature, A. A. Larsen et al, J. Med. Chem., 10, 462 (1967), with an improvement in such a manner that the reaction is effected in a polar solvent, such as acetonitrile, dimethylformamide, dimethylacetamide or dimethylsulfoxide, in the presence or absence of an amine as the acid-capturing agent under cooling with ice water or with heating at a temperature up to 60° C., followed by reduction of the carbonyl group using a reducing agent, such as sodium borohydride or sodium cyanoborohydride, under cooling with ice water or at room temperature, followed by deprotection of the protecting group. By this reaction, a racemic mixture of *1 is obtained, so that an optical resolution by the method as given afterwards becomes necessary for obtaining each optical active compound.

(Production Process B)

As an alternative production process in which each optical active compund or racemic modification is obtained, a technique using an epoxide may be incorporated.

Thus, the compound represented by the general formula (I) in which R is hydrogen atom and R1, R2, R6, n, X, R7, R8 and *1, *2 and *3 have the same meanings as those given previously can be produced by reacting a compound represented by the general formula (XII),

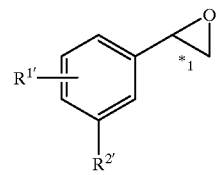

(XII)

in which R1', R2' and *1 have the meanings as those given previously, with the compound represented by the general formula (III) in which Y denotes hydrogen atom and R6, n, X, R7 , R8' and *2, *3 have the same meanings as those defined previously, followed by deprotection of the protecting groups A, (proviso that in case that R1 is benzyloxy and protecting group A is benzyl, the protecting group A is not de-protected) A", A'", that for protecting the amino group in the substituent R3' and the protecting acetyl group for R1' by the method described in the paragraph "Production Process A".

The reaction of the compound represented by the general formula (XII) with the compound represented by the general formula (III) can be carried out in a usual organic solvent, for example, dimethylsulfoxide, a straight chained or cyclic ether, dimethylformamide or dimethylacetamide. While the compound represented by the general formula (XII) and that represented by the general formula (III) are used often in an equimolar proportion, it is preferable to use an excess of the compound represented by the general formula (III) over the compound of the general formula (XII). The reaction is effected at an adequate temperature and, usually, at room temperature or the reflux temperature of the solvent employed. The reaction duration may be selected in accordance with the reaction condition and other factors and, usually, the reaction can be terminated at the point at which the yield becomes maximum.

It was reported that the yield of the reaction can be increased and the reaction duration is reduced by adding to the reaction mixture trimethylsilylacetamide (TMSA) [N,O-bis(trimethylsilylacetamide)], hexamethyldisilazane (HMDS) or bis(trimethylsilyl)urea [Tetrahedron Letters, 27, 2451 (1986)] and this may adequately be incoporated herein.

The compound represented by the general formula (XII) is known and can be synthesized by an ordinary method given in chemical literatures. For example, the general formula (XII) can be produced by oxidizing styrene or substituted styrene derivative using a peracid, such as m-chloroperbenzonic acid, or by reacting dimethylsulfonium methylimide or dimethylsulfoxonium methylide with a substituted benzaldehyde having a substituent group corresponding to R1' or R2 , as described in J. Am. Chem. Soc., 87, 1353 (1956).

A optical active compound represented by the general formula (XII) can be produced by reducing the compound represented by the general formula (II) or a substituted mandelic acid derivative in which the α-carbon atom (*1) is in a desired absolute configuration into a corresponding glycol derivative, tosylating or mesylating or halogenating, then, the resulting primary alcohol and cyclizing the resulting compound using a strong base, such as an alkali metal hydroxide, under a usual intramolecular nucleophilic substitution reaction.

(Production Process C)

Alternatively further, there is a method for producig a racemic modification by condensing a phenylglyoxal compound represented by the general formula (XIII)

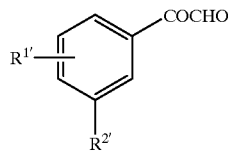

(XIII)

in which R1' and R2' have the same meanings as those given previously with an amine compound represented by the general formula (III) in which Y is hydrogen atom and R6, n, X, R7', R8' and *2, *3 have the same meanings as those given previously and reducing the resulting compound, with final deprotection of the protecting groups A, A''', A''', the protecting group for the amino group of R3 and the protecting acetyl group of R1' by the procedure described in the paragraph of "Production Process A" with the proviso that the deprotection of the protecting group A is unnecessary when R1 is benzyloxy and the protecting group A is benzyl to obtain the compound (I), wherein R is hydrogen atom, R1, R2, R6, n, X, R7, R8 and *1, *2 and *3 have the same meanings herein above.

This reaction is carried out in general in a rection solvent by reducing the Schiff base resulting from the condensation reaction using an adequate reducing agent capable of reducing the Schiff base and at the same time reducing the oxo-group into hydroxyl group. As the reducing agent, there may be employed, for example, sodium borohydride, sodium cyanoborohydride and lithium cyanoborohydride. The proportion of the phenylglyoxal compound to the amine compound is in general 1–3 moles, preferably 1–1.5 moles of the former to 1 mole of the amine compound. Reaction may be carried out at an adequate temperature and, in general, at a temperature from room temperature to the reflux temperature of the solvent employed. The reaction duration may adequately be chosen in accordance with the rection condition and so on and may be terminated at a point at which the reaction yield becomes highest. The above reactions may be carried out in a reaction solvent based on alcohol, such as methanol or ethanol, preferably at a low temperature in the presence of sodium borohydride.

The compound of the general formula (XIII) can be obtained easily by oxidizing an acetophenone derivative substituted by R1' and R2' in a reaction medium of water or an organic solvent, for example, a cyclic ether, such as dioxane or tetrahydrofuran, using an oxidizing agent, such as selenium dioxide. Alternatively, it can be produced by the process described in J. Am. Chem. Soc., 79, 6562 (1957).

(Production Process D)

The compound represented by the general formula (I) in which R is hydrogen and R1, R2, R6, n, R7, R8 and *1, *2 and *3 have the same meanings as those given previously can be obtained also by reacting an amine compound represented by the general formula (XIV),

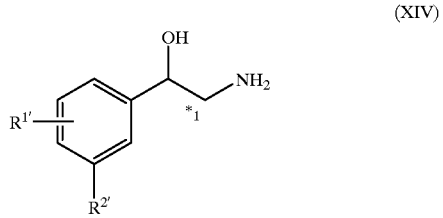

(XIV)

in which R1, R2' and *1 have the same meanings as those given previously, with a compound represented by the general formula (XV),

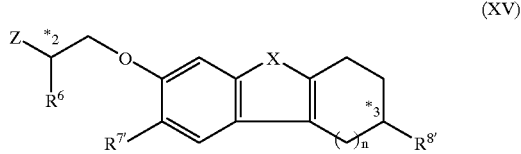

(XV)

in which R6, n, X, R7', R8' and *2, *3 have the same meanings as those given previously and Z denotes an eliminable group, followed by deprotection of the protecting groups A, A'', A''', that protecting the amino group in R3' and the protecting acetyl group in R1' by the method described in the paragraph (Production Process A), with the proviso that the deprotection of the protecting group A is unnecessary when R1 is benzyloxy and the protecting group A is benzyl, to produce the compound (I) wherein R is hydrogen, R1, R2, R6, n, R7, R8 and *1, *2 and *3 have the same meanings hereinbefore.

By effecting the coupling reaction with the amino compound in an organic solvent, if neccessary, in the presence of a proton-acceptor, such as a tertiary amine, for example, triethylamine, the compound represented by the general formula (I) is obtained. The "eliminable group" means a group which is elminated upon the above reaction of the chloride, bromide or iodide group or mesyl or tosyl group with, for exapmle, sulfonate or so on. The reaction may be realized, for example, using, in general, 1–10 moles of the amine compound represented by the general formula (XIV) per one mole of the compound represented by the general formula (XV).

Since this reaction proceeds at a lower velocity, the reaction may preferably be effected in an autoclave in a reaction solvent, for example, an alcohol, such as methanol, ethanol or buthanol, a haloganated hydrocarbon, such as methylene chloride or chloroform, or tetrahydrofuran or dioxane. The reaction temperature is chosen, in general, in the range from 10 to 150° C., preferably from 70 to 130° C. The reaction duration is chosen, in general, in the range from 5 to 100 hours.

The compound of the general formula (XIV) can be obtained by hydrogenating a substituted mandelonitrile substituted by R1' and R2' in the presence of a catalyst, such as Raney nickel. The substituted mandelonitrile can be produced by a reaction of a substituted benzaldehyde with hydrogen cyanide or with sodium cyanate together with sodium hydrogen sulfite as a racemic compound from which each optical active isomer can easily be separated by methods and techniques employed commonly by preparing salts of the diastereomers with an optically active acid selected adequately. The optically active substituted mandelonitrile derivative can be obtained by reacting the optically active carboxylic acid resulting from hydrolysis of the optically active substituted mandelonitrile with ammonia in the presence of a commonly employed condensing agent, followed by reduction of the resulting product.

The compound of the general formula (XV) can be obtained by reacting a phenol compound represented by the general formula (VIII) with a compound represented by the general formula (XVI),

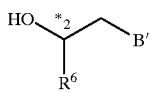

(XVI)

in which R6 and *2 have the same meanings as those given previously and B' is a halogen atom, or with a compound represented by the general formula (XVII),

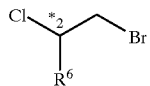

(XVII)

in which R6 and *2 have the same meanings as those given previously, under the condition of synthesizing the compound represented by the general formula (III) described in the paragraph of "Production Process A", followed by tosylating or mesylating the alcohol resulting from the above reaction with the compound represented by the general formula (XVI).

(Production Process E)

The compound represented by the general formula (I) in which R is methyl can be produced by methylating the alcohol compound of the general formula (I) in which R is hydrogen atom produced by the "Production Process A, B, C and D" under a commonly employed acidic condition. Thus, the compound of the general formula (I) in which R is methyl can be produced by treating the compound of the general formula (I) in which R is hydrogen atom with hydrogen chloride in methanol at a temperature from room temperature to the boiling point of the reaction medium.

The compound represented by the general formula (XVIII),

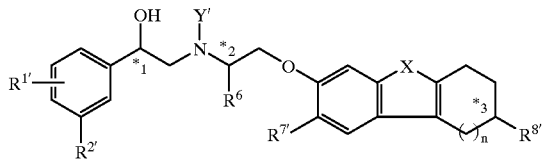

(XVIII)

in which R1', R2', R6, Y', n, X, R7 , R8' and *1, *2 and *3 have the same meanings as those given previously, which is a compound in which the amino group of the amine compound formed in the process for producing the compound represented by the general formula (I) in which R is hydrogen atom is protected by the protecting group Y' and in which a possible protecting group A' for the hydroxy gorup, if present, is de-protected by the method described above, is proceeded by methylation of the hydroxy group by a commonly used technique. By de-protected the protecting group Y' for the amino group and those of A, A", A'" and that protecting the amino group in R3, if present, as well as the protecting acetyl group in R1', with the proviso that the deprotection of the protecting group A is unnecessary when R1 is benzyloxy and the protecting group A is benzyl, the compound represented by the general formula (I) in which R is methyl and R1, R2 , R6, n, X, R7 , R8 and *1, *2 and *3 have the same meanings as those given previously is obtained.

A concrete example of methylation of the hydroxyl group consists in that the compound is reacted with 1–5 equivalents of methyl iodide or methyl bromide in the presence of a base, such as potassium carbonate, triethylamine, sodium hydroxide or sodium hydride, in a solvent, such as dimethylsulfoxide, dimethylformamide, dimethoxyethane or tetrahydrofuran, at a temperature in the range from room temperature to the reflux temperature of the solvent. An alternative embodiment consists in that the compound is reacted, in a form of its alkaline solution containing sodium hydroxide or potassium hydroxide in water or in methanol, with 2–10 equivalents of dimethyl sulfate at a temperature in the range from room temperature to the reflux temperature of the solvent.

The starting compounds of the present invention may, if necessary, be purified, wherein known chromatographic techniques including column-, flush column-, thin layer- and high performance liquid chromatography may be employed therefor by taking into account of such a parameter as the Rf value given in this specification.

As described above, the compound represented by the general formula (I) may be present as two or four or at maximum eight different isomers.

The process according to the present invention can provide both the pure isomer and racemic mixture. The reactions described above do not alter the pertaining stereo chemistry.

Therefore, starting from the compound of the general formula (V) or of the general formula (XIII) having no asymmetric carbon atom, starting from the racemic compound represented by the general formula (II), (XII) or (XIV), or starting from the racemic compound represented by the general formula (III) or (XV), isomeric mixtures are obtained. Similarly, starting from the pure isomer of the general formula (III) or (XV) and, for example, from the R-isomer of the general formula (III), (wherein R8 is hydrogen atom), mixtures of only two isomers (R, R) and (S, R) are obtained and, if an optical active isomer of the general formula (II), (XII) or (XIV) is employed, corresponding pure isomer can be obtained.

When R8 is hydrogen atom and a mixture of the four isomers or of two isomers is obtained, the isomer can be separated by a pertinent technique, such as fractional crystallization or the like, as their additional salts with an optically active acid, such as camphor sulfonic acid, mandelic acid or a substituted mandelic acid. The fractional crystallization may be performed using an adequate solvent, preferably a lower alkanol, such as ethanol or isopropanol or a mixture of them.

Every pair of the enantiomers can be separated into each optical active isomer by, for example, forming a diastereomeric salt and chromatographic separation on an optically active column, or by other means. When one of the starting raw materials is optically active, the mixture of the diastereomers obtained as above can be divided into each pure isomer. By separating each of the optical active isomers and purifying it, it becomes possible to improve the pharmacological effect or to eliminate side effects by using only the isomer having more higher activity which is preferable as a medicament.

As the salt of the compound represented by the general formula (I) according to the present invention, there may be exemplified salts with known acids, for example, addition salts thereof with mineral acids and organic acids, such as hydrochloric acid, hydrobromic acid, sulfuric acid, hydrogen sulfuric acid, dihydrogen phosphoric acid, citric acid, maleic acid, tartaric acid, fumaric acid, gluconic acid and methane sulfonic acid; and with optically active acids, such as camphor sulfonic acid, mandelic acid and substituted mandelic acids, wherein special preference is given to those which are medicamentally acceptable.

For preparing a salt of the compound represented by the general formula (I), the compound of the general formula (I) is dissolved in a alcohol, such as methanol or ethanol, and the acid component is added to the resulting alcoholic solution, whereby the corresponding acid addition salt can be obtained. Examples of the acids to be used therefor include mineral acids and organic acids which are medicamentally acceptable, such as hydrochloric acid, hydrobromic acid, sulfuric acid, hydrogen sulfuric acid, dihyrogen phosphoric acid, citric acid, tartaric acid, fumaric acid, gluconic acid and methane sulfonic acid.

The tricyclic compounds and the pharmacologically acceptable salts according to the present invention have no recognizable toxicity and are useful as medicaments and exhibit, for eaxmple, β3-activity, so that they can be utilized as medicaments for therapeutic and preventive treatments of β3-correlating diseases. The β3-correlating diseases is a generic expression for diseases which can be improved by a functional activity mediated 83-adrenaline receptor and include, for example, diabetes, obesity, hyperlipemia, diseases in a digestive system, such as abnormal motion and ulcer in digestive system, and depression. In particular, the compound according to the present invention serves for treating diabetes, obesity and hyperlipemia. Thus, the compound according to the present invention is effective as a medicament for preventive or herapeutic treatment of diabetes due to its function for decreasing the blood glucose value and is also effective for preventive treatment of hyperlipemia and therapeutic treatment of obesity due to its lipolytic activity.

In preparing a medicament from the compound according to the present invention, it is preferable to admix, if necessary, to an effective amount of the tricyclic compound represented by the general formula (I) or salt thereof a pharmacologically acceptable carrier to formulate a drug composition. As the pharmacologically acceptable carrier, there may be exemplified excipients, binding agents, such as carboxymethyl cellulose etc., disintegrator, lubricants and various additives.

For administering the drug containing the compound according to the present invention to human, oral administration of the drug in a form of tablet, powder, granules, capsule, sugar-coated tablet, solutions or syrup. Drugs for parenteral administration, such as drugs for injection, may be possible. The dose amount of administration may be different in accordance with the age, body weight, significance of the disease, symptom and so on and the dose may, in general, be in an amount of 0.01–2,000 mg per day for an adult all at once or alloted in several administrations. The term for receiving such drug may in general, range from several weeks to several months with daily administration, while it is possible to increase or decrease both the term and the daily dose in accordance with the state of the disease of patient.

The best mode for embodying the invention

Below, the present invention will further be descibed by way of Examples, wherein the present invention shold not be understood as being restricted thereto.

For thin layer chromatography (TLC). Precoated Silica Gel 60 F254 (of the firm Merck) was employed. After development with a mixed solvent of chloroform/methanol (100/1-4/1) or ethyl acetate/n-hexane (100/0-1/10), confirmation by UV-irradiation (254 nm) and color reaction with ninhydrin was performed. The Rf values of TLC cited refer to those of the free amines. For drying the organic solvent, anhydrous magnesium sulfate or anhydrous sodium sulfate was used. A silica gel (Wako-gel C-200, a product of Wako Pure Chemical Ind., Ltd.) was used for the column chromatography and Silica Gel 60 (230–400 mesh, a product of the firm Merck) was used for the flush column chromatography. Pre-coated Silica Gel 60 F254 (20×20 cm. 2 mm ; supplied from Merck) was used for the preparative thin layer chromatography. Elution was effected using a mixed developer of chloroform/methanol (1/1).

For observing the nuclear magnetic resonance spectrum (NMR), Gemini -300 (FT-NMR ; of the firm Varian) was employed. As the solvent, CDC13 was used so long as no special mention is made. Tetramethylsilane (TMS) was used as the internal standard for the chemical shift which was recorded in terms of (δ ppm). The coupling constant is indicated by J(Hz). For observing mass spectrum (MS), JEOL-SX102 was employed and the observation was made by fast atom bombard mass spectrum (FAB-MS). The analyzed results are summarized in Table 1.

Intermediate 1

Synthesis of 2-benzyloxycarbonylamino-1-bromoethane

To a solution of 2-bromoethylamine hydrochloride (25 g: a product of Tokyo Kasei Kogyo Co., Ltd.) and triethylamine (34 ml) in methylene chloride (450 ml), benzyloxycarbonyl chloride (19 ml) was added dropwise over a period of 20 minutes and the mixture was agitated at room temeprature for 19 hours. The resulting reaction mixture was washed with water, with saturated aqueous sodium bicarbonate solution and with saturated aqueous sodium chloride succeedingly, whereupon the separated organic layer was dried and, then, removed off the solvent by distilling it of under reduced pressure. The residue was cooled with ice and the crystals were collected by filtration and washed with hexane, whereby the above-identified compound was obtained (29.4 g).

Rf=0.58 (chlorogorm)

Intermediate 2

Synthesis of 2-(2-benzyloxycarbonylaminoethoxy)-5,6,7,8-tetrahydro-9H-carbazole

A solution of 2-hydroxy-5,6,7,8-tetrahydro-9H-carbazole (4.33 g prepared by the method disclosed in Japanese patent kokai sho 61-57555) and the above intermediate 1 (0.76 g) in acetone (200 ml) was refluxed by heating at 70° C. for 23 hours with addition of potassium carbonate (11.28 g). The heating reflux was further continued for 4.7 hours after adding thereto the intermediate 1 (3.51 g) and potassium carbonate (3.76 g). Thererto were then added ethyl acetate (1.5 liters) and water (1 liter) to effect extraction. After the extraction, the organic layer was washed with saturated aqueous sodium chloride solution and dried, whereupon the solvent was distilled off under reduced pressure. The resulting residue was purified by a columnchromatography (conc. ammonia water/methanol/chloroform=1/9/150) to obtain the above-identified compound (1.384 g).

Rf=0.61 (ethyl acetate/n-hexane=1/1)

Intermediate 3

Synthesis of 2-(5,6,7,8-tetrahydro-9H-carbazol-2-yloxy) ethylamine

To the above intermediate 2 (5.4 g), 30% solution (28.6 ml) of hydrogen bromide in acetic acid was added and the mixture was agitated at room temperature for 1.0 hour. Thereto was added diethyl ether and the thereby deposited precipitate was collected by filtration and washed with diethyl ether. This precipitate was introduced into a mixture of water and ethyl acetate and the mixture was adjusted at pH 10 by adding 6N NaOH solution, whereupon the mixture was subjected to extraction with ethyl acetate. After drying the organic layer, the solvent was distilled off under reduced pressure, whereby the above-identified compound was obtained (3.23 g).

Rf=0.07 (methanol/chloroform=1/10)

Intermediate 4

Synthesis of 3-(2-benzyloxycarbonylaminoethoxy)-6,7,8, 9-tetrahydrodibenzofuran

To a solution of 3-hydroxy-6,7,8,9-tetrahydrodibenzofuran {0.999 g; prepared in accordance with the disclosure by Erdtman, H. et al, Acta Chem. Scand. 15, p 1761 (1961)} and the above intermediate 1 (1.65 g) in dimethylformamide (11 ml), potassium carbonate (2.20 g) was added and the mixture was agitated at room temperature for 70.5 hours. Thereto was further added the intermediate 1 (0.42 g) and potassium carbonate (0.74 g) and the mixture was agitated for further 5 hours. The reaction mixture was heated to 60° C. and agitated for 4 hours, whereupon the mixture was cooled down to room temperature. Water (100 ml) was added thereto and the mixture was agitated vigorously for 14.5 hours. The deposited precipitate was collected by filtration and washed with water, whereupon it was dried under reduced pressure at 50° C. for 3.5 hours to obtain the above-identified compound (1.91 g).

Rf=0.18 (ethyl acetate/n-hexane=1/5)

Intermediate 5

Synthesis of 2-(6,7,8,9-tetrahydrodibenzofuran-3-yloxy) ethylamine

To the above intermediate 4 (3.5 g), 30% solution (50 g) of hydrogen bromide in acetic acid was added and the mixture was agitated at room temperature for 1.2 hours. Thereto was added diethyl ether (500 ml) and the thereby deposited precipitate was collected by filtration and washed with diethyl ether. This precipitate was suspended in water (100 ml) and the mixture was adjusted at pH 11 by adding 5N NaOH solution, whereupon the mixture was subjected to extraction with ethyl acetate (200 ml×twice). After drying the organic layer, the solvent was distilled off under reduced pressure, whereby the above-identified compound was obtained (2.14 g).

Rf=0.16 (methanol/chloroform=1/10)

Intermediate 6

Synthesis of 3-(2-benzyloxycarbonylaminoethoxy)-6,7,8, 9-tetrahydrodibenzothiophene To a solution of 3-hydroxy-6,7,8,9-tetrahydrodibenzothiophene (237 mg; prepared in accordance with the method given in DT 2113455) and the above intermediate 1 (600 mg) in dimethylformamide (3 ml), potassium carbonate (500 mg) was added and the mixture was agitated at room temperature for 20 hours. Water was added thereto and extraction was effected with ethyl acetate, followed by washing with saturated aqueous sodium chloride solution, drying and evaporating under reduced pressure. The resulting residue was purified by a column chromatography (ethyl acetate/n-hexane=1/4) to obtain a purified product of the above-identified compound (475.1 mg).

Rf=0.64 (ethyl acetate/n-hexane=1/1)

Intermediate 7

Synthesis of 2-(6,7,8,9-tetrahydrodibenzothiophen-3-yloxy) ethylamine

To the above intermediate 6 (475.1 mg), 30% solution (5 ml) of hydrogen bromide in acetic acid was added and the mixture was agitated at room temperature for 2 hours. Thereto was added diethyl ether (25 ml) and the thereby deposited precipitate was collected by filtration and washed with diethyl ether. This precipitate was dissolved in water (100 ml) and the solution was adjusted at pH 11 by adding 8 N NaOH solution, followed by extraction with ethyl acetate (50 ml×thrice), drying of the organic layer and evaporated under reduced pressure, whereby the above-identified compound was obtained (155.2 mg).

Rf=0.19 (methanol/chloroform=1/10)

Intermediate 8

Synthesis of (R)-2-bromo-1-[3-nitro-4-(benzyloxy) phenyl]ethanol

To a solution of 2-bromo-1-[3-nitro-4-(benzyloxy) phenyl]ethanone {1.01 g, 70% purity; prepared by the method reported by C. Kaiser et al in J. Med. Chem., 17, 49 (1974) } and (R)-3,3-diphenyl-1-methyltetrahydro-1H, 3H-pyrolo [1,2-c] [1.3.2]oxazaborol (100 mg, a product of Tokyo Kasei Kogyo Co., Ltd.; denoted in the following as "the asymmetric catalyst", which may exist either in R- or S-form) in anhydrous tetrahydrofuran (20 ml, prepared upon each use), there was added dropwise a 2 M solution of borane-dimethyl sulfide complex in tetrahydrofuran (2.16 ml, a product of the firm Aldrich) with agitation under cooling with an ice/salt freezing mixture over a period of 5 minutes and agitation was continued at this same temperature for 2 hours. Then, the reaction mixture was diluted with ethyl acetate, followed by washing with saturated ammonium chloride solution and with saturated aqueous sodium chloride solution succeedingly, drying and evaporating under reduced pressure. The resulting residue was purified by a column chromatography (ethyl acetate/n-hexane=1/2-1/1) to obtain a purified product of the above-identified compound (1.015 g).

Rf=0.41 (ethyl acetate/n-hexane=1/1)

Retention time: 35.7 minutes

Analysis conditions:

Column: CHIRALCEL AD (4.6 mm ϕ×25 cm), supplied from Daicel Chemical Industries, Ltd.

Mobile phase: n-hexane/2-propanol=7/3

Flow rate: 0.5 ml/min.

Detection wave length: 254 nm

Temperature: 35° C.

Intermediate 9

Synthesis of (R)-3-nitro-4-benzyloxy-[2-iodo-1-(triethylsilyloxy) ethyl]benzene

To a solution of the intermediate 8 (695.6 mg) in a acetone (30 ml), sodium iodide (2.96 g; a product of Wako Pure Chemical Industries, Ltd.) was added and the mixture was refluxed with heating for 2 hours. After cooling down to room temperature, the mixture was filtered and the filtrate was distilled off under reduced pressure. To the residue, there were added chloroform and water. The organic layer was washed with saturated sodium thiosulfate solution, followed by drying and evaporating under reduced pressure. The resulting oily product (0.78 g) was dissolved together with imidazole (408.5 mg) and dimethylaminopyridine (24.4 mg) in dimethylformamide (5 ml), whereupon chlorotriethylsilane (452 mg) was added to the solution with ice-cooling. The reaction mixture was warmed at once to room temperature and agitated for 1.5 hours. The mixture was diluted with ethyl acetate and was washed with water, with 2% copper sulfate solution, with water and finaly with saturated aqueous sodium chloride solution succeedingly, followed by drying and evaporating under reduced pressure. The residue was purified by a column chromatography (ethyl acetate/n-hexane=1/3), whereby a purified product of the above-identified compound was obtained (915 mg).

Rf=0.76 (ethyl acetate/n-hexane=1/1)

Intermediate 10

Synthesis of (S)-3-nitro-4-benzyloxy-[2-iodo-1-(triethylsilyloxy) ethyl]benzene

A. Synthesis of (S)-2-bromo-1-[3-nitro-4-(benzyloxy) phenyl]ethanol

The reaction and the after-treatment as in the case of intermdiate 8 were pursued, except that an asymmetric catalyst of S-form (a product of Tokyo Kasei Kogyo Co., Ltd.) was used.

Retention time: 47.3 minutes
Analysis conditions:
Column: CHIRALCEL AD (of the firm Daicel Chemical)
Mobile phase: n-hexane/2-propanol=7/3
Flow rate: 0.5 ml/min.
Detection wave length: 254 nm
Temperature: 35° C.

B. Synthesis of (S)-3-nitro-4-benzyloxy-[2-iodo-1-(triethylsilyloxy) ethyl]benzen Using the intermediate obtained as above, the reaction and the after-treatment as in the case of synthesis of intermediate 9 were pursued.

Rf=0.76 (ethyl acetate/n-hexane=1/1)

Intermediate 11

Synthesis of (±)-N-[5-(2-bromo-1-hydroxyethyl)-2-benzyloxyphenyl]-N,N-dimethylsulfamide To an ice-cooled solution of 2-bromo-1-[4-(benzyloxy)-3-(dimethylsulfamoylamino)phenyl]ethanone {15.1 g; prepared by the method reported by C. Kaiser et al in J. Med. Chem., 17, 49–57 (1974)} anhydrous tetrahydrofuran (197 ml), 1 M solution of a borane/tetrahydrofuran complex in tetrahydrofuran (61.9 ml; a product of the firm Aldrich) was added all at once under an argon atomsphere and mixture was agitated at this same temperature for 75 minutes. The mixture was then dilluted with 500 ml of ethyl acetate and thereto was added saturated aqueous ammonium chloride solution little by little, whereupon the organic layerwas washed twice. The organic layer was collected by phase separation and washed with saturated aqueous sodium chloride solution, followed by drying over anhydrous sodium sulfate and evaporating under reduced pressure. After a further drying under reduced pressure using a vacume pump overnight, the above-identified compound was obtained (14.91 g).

Rf=0.27 (ethyl acetate/n-hexane=1/2)

Intermediate 12

Synthesis of (±)-N-[5-[2-iodo-1-(triethylsilyloxy)ethyl]-2-benzyloxyphenyl]-N,N-dimethylsulfamide To a solution of the intermediate 11 (14.9 mg) in a acetone (212.9 ml), sodium iodide (58.09 g) was added and the mixture was refluxed with heating for 105 minutes. After cooling down to room remperature, filtration and evaporating under reduced pressure were followed. The residue was partitioned between dichloromethane (240 ml) and water (240 ml) and organic layer was washed twice with 23.5% (w/w %) aqueous sodium hydrogen sulfite, then, with water and finally with saturated aqueous sodium chloride solution, followed by drying and evaporating under resuced pressure. The resulting masswas further dried under a reduced pressure using a vacuum pump for 2 hours, whereby a brown tar-like product (iodide product, 15.51 g) was obtained. This product was dissolved in dimethylformamide (75.6 ml), whereto imidazole (6.1 g) and 4-dimethylaminopyridine (346 mg) were added at room temperature and, then, chlorotriethylsilane (5.83 ml) was further added. After agitation for 35 minutes', the mixture was dilluted with ethyl acetate (250 ml) and n-heptane (100 ml), followed by washing with water (125 ml), with saturated copper sulfate solution (125 ml, twice), with water (125 ml) and with saturated aqueous sodium chloride solution (125 ml), drying and evaporating under reduced pressure. The residue was treated by a silica gel column chromatography, whereby the objective product (15.41 g) was obtained as a pale brown solid from a n-hexane eluate fraction.

Rf=0.86 (ethyl acetate/n-hexane=1/1)

Intermediate 13

Synthesis of (R)-N'-[5-[2-iodo-1-(triethylsilyloxy)ethyl]-2-benzyloxyphenyl]-N,N-dimethylsulfamide A. Synthesis of (R)-N'-[5-(2-bromo-1-hydroxyethyl)-2-benzyloxyphenyl]-N,N-dimethylsulfamide In accordance with the practice of synthesis of the intermediate 8, the above-identified compound (925.7 mg) was obtained from 2-bromo-1-[4-(benzyloxy)-3-(dimethylsulfamoylamino)phenyl]ethanone [1.058 g; prepared by the method reported by C. Kaiser et al in J. Med. Chem., 17, 49–57 (1974)].

Retention time: 19.5 minutes for R-compound (17.5 minutes for S-compound)
Analysis conditions:
Column: 4.6 mm ID×250 mm; CHIRALCEL OJ (of the firm Daicel Chemical)
Mobile phase: ethanol/n-hexane=1/1
Flow rate: 0.7 ml/min.
Detection wave length: 254 nm
Temperature: room temperature B. Synthesis of (R)-N'-[5-[2-iodo-1-(triethylsilyloxy)ethyl]-2-benzyloxyphenyl]-N,N-dimethylsulfamide From the above intermediate (925 mg), the above-identified compound (1.27 g) was obtained in two process steps in a similar way as in the synthesis of the intermediate 12 (racemate).

Intermediate 14

Synthesis of (S)-N'-[5-[2-iodo-1-(triethylsilyloxy)ethyl]-2-benzyloxyphenyl]-N,N-dimethylsulfamide A. Synthesis of (S)-N'-[5-(2-bromo-1-hydroxyethyl)-2-benzyloxyphenyl]-N,N-dimethylsulfamide In accordance with the practice of synthesis of the intermediate 10, the above-identified compound (928.1 mg) was obtained from 2-bromo-1-[4-(benzyloxy)-3-(dimethylsulfamoylamino)phenyl]ethanone [1.05 g; prepared by the method reported by C. Kaiser et al in J. Med. Chem., 17, 49–57 (1974)] using S-form compound as the asymmetric catalyst.

Retention time: (19.6 minutes for R-compound), 17.4 minutes for S-compound
Analysis conditions:
Column: 4.6 mm ID×250 mm; CHIRALCEL OJ (of the firm Daicel Chemical)
Mobile phase: ethanol/n-hexane=1/1
Flow rate: 0.7 ml/min.

Detection wave length: 254 nm
Temperature: room temperature
B. Synthesis of (S)-N'-[5-[2-iodo-1-(triethylsilyloxy)-ethyl]-2-benzyloxyphenyl]-N,N-dimethylsulfamide (intermediate 14)

From the above intermediate (868.1 mg), the above-identified compound (1.18 g) was obtained in two process steps in a similar way as in the synthesis of the intermediate 12 (racemate).

Intermediate 15

Synthesis of 1-(4-fluoro-3-nitrophenyl)ethanone

To fuming nitric acid (100 ml) cooled at −10° C., there was added with agitation 4'-fluoroacetophenone (13.8 g: a product of the firm Tokyo Kasei Kogyo) alloted in two portions. After warmed up to room temperature, the mixture was agitated for 4 hours. This mixture was poured into ice water (1.0 liter) and was extracted with ethyl acetate (500 ml). After drying the organic layer, the solvent was distilled off under reduced pressure. The resulting product was purified twice by a column chromatography (n-hexane/ethyl acetate=9/1-4/1), whereby the above-identified compound (4.16 g) was obtained.

Rf=0.50 (chloroform)

Intermediate 16

Synthesis of 1-(3-amino-4-fluorophenyl)ethanone

To an argon-purged methanol solution (305 ml) of the intermediate 15 (4.16 g), platinum oxide (anhydrous, 189.7 mg) was added, whereupon reduction was effected under 1 atm. hydrogen at room temperature. After agitation for 6 hours, the reaction system was replaced by argon and the reaction mixture was diluted with chloroform, followed by filtration. The solvent was distilled off under reduced pressure, whereby the above-identified compound was obtained (3.52 g).

Rf=0.47 (ethyl acetate/n-hexane=1/1)

Intermediate 17

Synthesis of 1-[4-fluoro-3-[(methylsulfonyl)amino]phenyl]ethanone

To a solution of the intermediate 16 (3.48 g) in pyridine (100 ml), methanesulfonyl chloride (1.93 ml) was added at room temperature. After agitation for 2.5 days', the reaction mixture was poured into saturated ammonium chloride solution and was extracted with ethyl acetate (200 ml). The organic layer was washed with saturated aqueous sodium chloride solution (100 ml×thrice), followed by drying and concentration under reduced pressure, whereby a crude product was obtained. By purifying this crude product by a column chromatography (n-hexane/ethyl acetate=1/1), the above-identified compound was obtained (3.9 g).

Rf=0.23 (ethyl acetate/n-hexane=1/1)

Intermediate 18

Synthesis of 2-bromo-1-[4-fluoro-3-[(methylsulfonyl)amino]phenyl]ethanone

To a solution of the intermediate 17 (3.9 g) in 1,4-dioxane (50 ml), bromine (2.83 g) was added with agitation. This mixture was warmed to 60° C. and was agitaed for 1 hour. After cooling down to room temperature, the mixture was concentrated under reduced pressure. Water is added to the residue and the deposited precipitate was triturated and collected by filtration. The filtrated mass was washed with cold ethanol and dried, followed by recrystallization from ethanol to obtain the above-identified compound (3.69 g).

Rf=0.30 (ethyl acetate/n-hexane=1/2, developed three times)

Intermediate 19

Synthesis of (±)-N-[5-[2-iodo-1-(triethylsilyloxy)ethyl]-2-fluorophenyl]methanesulfonamide Reaction and after-treatment were effected in accordance with the procedures of synthesis of the intermediates 11 and 12, whereby the above-identified compound was obtained (10.22 g).

Rf=0.36 (ethyl acetate/n-hexane=1/3)

Intermediate 20

Synthesis of (R)-N-[5-(2-bromo-1-hydroxyethyl)-2-fluorophenyl]methanesulfonamide From the above intermediate 18 (1.53 g), the above-identified compound (1.79 g) was obtained by reaction and after-treatment in accordance with the procedures of synthesis of the intermediate 8.

Retention time: 31.1 minutes for R-compound (33.3 minutes for S-compound

Analysis conditions:
Column: 4.6 mm ID×250 mm; CHIRALPAK AD (of the firm Daicel Chemical)
Mobile phase: ethanol/n-hexane=1/1
Flow rate: 0.3 ml/min.
Detection wave length: 254 nm
Temperature: room temperature Intermediate 21

Synthesis of (R)-N-[5-[2-iodo-1-[(triethylsilyl)oxy]ethyl]-2-fluorophenyl]methanesulfonamide From the above intermediate 20 (1.78 g), the above-identified compound (2.29 g) was obtained by reaction and after-treatment in accordance with the procedures of synthesis of the intermediate 9.

Rf=0.36 (ethyl acetate/n-hexane=1/3)

Intermediate 22

Synthesis of (S)-N-[5-(2-bromo-1-hydroxyethyl)-2-fluorophenyl]methanesulfonamide From the above intermediate 18 (1.53 g), the above-identified compound (1.36 g) was obtained by reaction using S-compound as the asymmetric catalyst and after-treatment in accordance with the procedures of synthesis of the intermediate 8.

Retention time : (31.1 minutes for R-compound) 33.3 minutes for S-compound

Analysis conditions:
Column: 4.6 mm ID×250 mm; CHIRALPAK AD (of the firm Daicel Chemical)
Mobile phase: ethanol/n-hexane=1/1
Flow rate: 0.3 ml/min.
Detection wave length: 254 nm
Temperature: room temperature Intermediate 23

Synthesis of (S)-N-[5-[2-iodo-1-[(triethylsiliyl)oxy]ethyl]-2-fluorophenyl]methanesulfonamide From the above intermediate 22 (1.36 g), the above-identified compound (1.85 g) was obtained by reaction and after-treatment in accordance with the procedures of synthesis of the intermediate 9.

Rf=0.36 (ethyl acetate/n-hexane=1/3)

Intermediate 24

Synthesis of 1-(4-chlolo-3-nitrophenyl)ethanone

To fuming nitric acid (100 ml) cooled at −10° C., there were added with agitation 4'-chloroacetophenone (15.5 g; a product of the firm Tokyo Kasei Kogyo) allotted in two portions. After warmed up to room temperature, the mixture was agitated for 4 hours. This mixture was poured onto ice water (1.6 liters) and was extracted with ethyl acetate (800 ml). After drying the organic layer, the solvent was distilled off under reduced pressure. The resulting product was treated by a column chromatography (n-hexane/ethyl acetate=9/1-4/1), whereby the above-identified compound (1.2 g) was obtained.

Rf=0.52 (chloroform)
Intermediate 25

Synthesis of 1-(3-amino-4-chlorophenyl)ethanone

To a solution of the intermediate 24 (1.4 g) in methanol (260 ml), tin (II) chloride (7.63 g) and concentrated hydrochloric acid (5.48 ml) were added and the mixture was agitated at room temperature for 3.5 hours. The mixture was concentrated and was washed with saturated aqueous sodium bicarbonate solution, followed by extraction with ethyl acetate. The organic layer was concentrated under reduced pressure, whereby the above-identified compound was obtained (970 mg).

Rf=0.49 (ethyl acetate/n-hexane=1/1)
Intermediate 26

Synthesis of 1-[4-chloro-3-[(methylsulfonyl)amino]phenyl]ethanone

To a solution of the intermediate 25 (970 mg) in pyridine (50 ml), methanesulfonyl chloride (487 µl) was added at room temperature. After agitation for 2.5 days', the reaction mixture was poured into saturated ammonium chloride solution and was extracted with ethyl acetate (100 ml). The organic layer was washed with saturated aqueous sodium chloride solution (50 ml×thrice), followed by drying and concentration under reduced pressure, whereby a crude product was obtained. By purifying this crude product by a column chromatography (n-hexane/ethyl acetate 3/2-1/1), the above-identified compound was obtained (890 mg).

Rf=0.41 (ethyl acetate/n-hexane=1/1)
Intermediate 27

Synthesis of 2-bromo-1-[4-chloro-3-[(methylsulfonyl)amino]phenyl]ethanone

To a solution of the intermediate 26 (890 mg) in 1,4-dioxane (10 ml), bromine (605 mg) was added with agitation. This mixture was warmed to 60° C. and was agitation for 1 hour. After cooling down to room temperature, the mixture was concentrated under reduced pressure. Water is added to the residue and the precipitate was triturated and collected byfiltration. The filtrated mass was washed with cold ethanol and dried, followed by recrystallization from ethanol to obtain the above-identified compound (620 mg).

Rf=0.39 (ethyl acetate/n-hexane=1/1)
Intermediate 28

Synthesis of (R)-N-[5-(2-bromo-1-hydroxyethyl)-2-chlorophenyl]methanesulfonamide From the above intermediate 27 (800 mg), the above-identified compound (880 mg) was obtained by reaction and after-treatment in accordance with the procedures of synthesis of the intermediate 8.

Retention time: 14.1 minutes for R-compound (16.8 minutes for S-compound

Analysis conditions:
Column: 4.6 mm ID×250 mm; CHIRALPAK AD (of the firm Daicel Chemical)
Mobile phase: ethanol/n-hexane=4/1
Flow rate: 0.5 ml/min.
Detection wave length: 254 nm
Temperature: room temperature
Intermediate 29

Synthesis of (R)-N-[5-[2-iodo-1-[(triethylsiliyl)oxy]ethyl]-2-chlorophenyl]methanesulfonamide From the above intermediate 28 (880 mg), the above-identified compound (1.24 g) was obtained by reaction and after-treatment in accordance with the procedures of synthesis of the intermediate 9.
Intermediate 30

Synthesis of (S)-N-[5-(2-bromo-1-hydroxyethyl)-2-chlorophenyl]methanesulfonamide From the above intermediate 27 (780 mg), the above-identified compound (753.4 mg) was obtained by reaction using S-compound as the asymmetric catalyst and after-treatment in accordance with the procedures of synthesis of the intermediate 8.

Retention time: (14.1 minutes for R-compound) 16.8 minutes for S-compound

Analysis conditions:
Column: 4.6 mm ID×250 mm; CHIRALPAK AD (of the firm Daicel Chemical)
Mobile phase: ethanol/n-hexane=4/1
Flow rate: 0.5 ml/min.
Detection wave length: 254 nm
Temperature: room temperature
Intermediate 31

Synthesis of (S)-N-[5-[2-iodo-1-[(triethylsiliyl)oxy]ethyl]-2-chlorophenyl]methanesulfonamide From the above intermediate 30 (753 mg), the above-identified compound (1.06 g) was obtained by reaction and after-treatment in accordance with the procedures of synthesis of the intermediate 9.
Intermediate 32

Synthesis of 1-[4-bromo-3-[(methylsulfonyl)amino]phenyl]ethanone

To a solution of 4-bromo-3-nitroacetophenone (5.0 g, supplied from the firm Lancaster) in methanol (890 ml), tin (II) chloride (19.4 g) and concentrated hydrochloric acid (17 ml) were added and the mixture was agitated at room temperature for 3.5 hours. Thereto was added saturated aqueous sodium bicarbonate solution (470 ml) and the deposited precipitate was collected by filtration, followed by extraction with ethyl acetate. The organic layer was dried and, then, concentrated under reduced pressure, whereby the above-identified compound was obtained (3.97 g).

Rf=0.43 (ethyl acetate/n-hexane=1/2)

To a solution of the above compound (3.97 g) in pyridine (21 ml), methanesulfonyl chloride (1.8 ml) was added at room temperature. After agitation for 1 hour, the reaction mixture was poured into water (142 ml). After agitation for overnight, the deposited precipitate was collected by filtration, which was then dissolved in ethyl acetate. The organic layer was washed with saturated aqueous sodium chloride solutionand dried, followed by concentration under reduced pressure, whereby a crude product (4.08 g) was obtained.

Rf=0.41 (ethyl acetate/n-hexane=1/1)
Intermediate 33

Synthesis of 2-bromo-1-[4-bromo-3-[(methylsulfonyl)amino]phenyl]ethanone

To a solution of the intermediate 32 (4.08 g) in 1,4-dioxane (40 ml), bromine (0.75 ml) was added with agitation under an argon atmosphere. This mixture was warmed to 60° C. and was agitated for 1.5 hour. After cooling down to room temperature, water was extracted with ethyl acetate, whereupon the organic layer was washed with saturated aqueous sodium chloride solution and dried, followed by concentration under reduced pressure, whereby a crude product was obtained (6.28 g). To this crude product was added a 1/1 mixture acetate/n-hexane and the resulting mixture was warmed. After cooling, the deposited precipitate was collected by filtration, whereby the above-identified compound (4.0 g) was obtained.

Rf=0.54 (ethyl acetate/n-hexane=1/1)
Intermediate 34

Synthesis of (R)-N-[5-[2-bromo-1-hydroxyethyl]-2-bromophenyl]methanesulfonamide

From the above intermediate 33 (22.0 g), the above-identified compound (23.1 g) was obtained by reaction and after-treatment in accordance with the procedures of synthesis of the intermediate 8.

Rf=0.36 (ethyl acetate/n-hexane=1/1)

Intermediate 35

Synthesis of (R)-N-[5-[2-iodo-1-[(triethylsilyl)oxy]ethyl]-2-bromophenyl]methanesulfonamide From the above intermediate 34 (1.85 g), the above-identified compound (2.48 g) was obtained by reaction and after-treatment in accordance with the procedures of synthesis of the intermediate 9.

Rf=0.26 (ethyl acetate/n-hexane=1/5)

Intermediate 36

Synthesis of 2-benzyloxy-5-acetylbenzenesulfonyl chloride 1-(3-amino-4-benzyloxyphenyl)ethanone {2.41 g, prepared by the method reported by A. A. Larsen et al in J. Med. Chem., 10, 462–472 (1967)} was dissolved in acetic acid (5 ml) and thereto were added 5 ml of concentrated hydrochloric acid. Thereto was added an aqueopus solution (7 ml) of sodium nitrite (1.0 g) with agitation at −10° C. over a period of 50 minutes. The resulting mixture was agitated for further 28 minutes with ice-cooling, whereupon a solution of thionyl chloride (3.5 ml) in acetic acid (6.5 ml) and an aqueous solution (3 ml) of cupric chloride dihydrate (720 mg) were added thereto succeedingly, followed by agitation for 6 hours while getting the temperature thereof back to room temperature. The deposited precipitate was collected by filtration and dissolved in chloroform and the resulting solution was washed with water and dried, before it was concentrated to a volume of 50 ml under a reduced pressure to prepare a chloroform solution of 2-benzyloxy-5-acetyl-benzenesulfonyl chloride.

Intermediate 37

Synthesis of N-methyl-(2-benzyloxy-5-acetylbenzene)sulfonamide

To a chloroform solution of the intermediate 36, a 40% aqueous solution (1.0 ml) of methylamine was added and the mixture was agitated at room temperature for 16.5 hours. Water (50 ml) was added to the reaction mixture and the organic layer was collected by phase separation. The aqueous phase was extracted with chloroform (50 ml) once and the combined organic phase was washed with saturated aqueous sodium chloride solution and dried, whereupon the solvent was distilled off under reduced pressure. By purifying with a silica gel chromatography (chloroform-methanol/chloroform=1/19), the above-identified compound was obtained (200 mg).

Rf=0.05 (chloroform)

Intermediate 38

Synthesis of N-methyl-[2-benzyloxy-5-(2-bromoacetyl)benzene]sulfonamide

Cupric bromide (6.02 g) was suspended in ethyl acetate (150 ml) under an argon atmosphere, whereto a solution of the intermediate 37 (3.91 g) in chloroform (150 ml) was added under reflux with heating. After refluxing for 5.5 hours, the mixture was cooled down to 62° C. and was diluted with chloroform, whereupon the suspension was hot filtered and the filtrate was subjected to concentration under reduced pressure. The residue was suspended in isopropyl alcohol and the deposited precipitate was collected by filtration, followed by washing with cold isopropyl alcohol and drying, whereby the above-identified compound was obtained (2.04 g).

Rf=0.83 (ethyl acetate/n-hexane=1/1)

Intermediate 39

Synthesis of (R)-N-methyl-[5-(2-bromo-1-hydroxyethyl)-2-benzyloxy]benzenesulfonamide From the above intermediate 38 (800 mg), the above-identified compound (752.2 mg) was obtained by reaction and after-treatment in accordance with the procedures of synthesis of the intermediate 8.

Rf=0.15 (ethyl acetate/n-hexane=1/2)

Intermediate 40

Synthesis of (R)-N-methyl-[5-[2-iodo-1-[(triethylsilyl)oxy]ethyl]-2-benzyloxy]benzenesulfonamide From the above intermediate 39 (462.8 mg), the above-identified compound (587.9 mg) was obtained by reaction and after-treatment in accordance with the procedures of synthesis of the intermediate 9.

Rf=0.53 (ethyl acetate/n-hexane=1/2)

Intermediate 41

Synthesis of N-methyl-[2-chloro-5-(2-bromoacetyl)benzene]sulfonamide

To a solution of N-methyl-(2-chloro-5-acetylbenzene)sulfonamide {3.29 g; prepared by the method described by T. Fujikura et al in Chem. Pharm. Bull., 30 (II), 4092–4101 (1982)} in 1,4-dioxane (35 ml), bromine (0.72 ml) was added with agitation. This mixture was warmed to 60° C. and was agitated for 2 hours. After cooling down to room temperature, the mixture was concentrated under reduced pressure. Water (25 ml) was added to the residue and the mixture was extracted with ethyl acetate (40 ml), followed by washing with aqueous sodium chloride solution and drying, whereupon the solvent was distilled off under reduced pressure. After purification by a silica gel chromatography (ethyl acetate/n-hexane=1/2), the above-identified compound (2.35 g) was obtained as a yellowish oily substance.

Rf=0.49 (ethyl acetate/n-hexane=1/1)

Intermediate 42

Synthesis of (R)-N-methyl-[5-(2-bromo-1-hydroxyethyl)-2-chloro]benzenesulfonamide From the above intermediate 41 (2.35 g), the above-identified compound (2.10 g) was obtained by reaction and after-treatment in accordance with the procedures of synthesis of the intermediate 8.

Rf=0.58 (ethyl acetate/n-hexane=1/1)

Intermediate 43

Synthesis of (R)-N-methyl-[5-[2-iodo-1-[(triethylsilyl)oxy]ethyl]-2-chloro]benzenesulfonamide From the above intermediate 42 (2.05 g), the above-identified compound (1.75 g) was obtained by reaction and after-treatment in accordance with the procedures of synthesis of the intermediate 9.

Rf=0.58 (ethyl acetate/n-hexane=1/2)

Intermediate 44

Synthesis of (1)-N-[3-[2-iodo-1-[(triethylsilyloxy]ethyl]phenyl]methanesulfonamide From 2-bromo-1-[3-(methylsulfonyl)aminophenyl]-ethanone [45 g, prepared by the method reported by A. A. Larsen et al in J. Med. Chem., 9, 88–97 (1966)], the above-identified compound (68.25 g) was obtained in accordance with the procedures of synthesis of the intermediates 11 and 12.

Rf=0.48 (methanol/chloroform=1/10)

Intermediate 45

Synthesis of (R)-2-bromo-1-(3-nitrophenyl)ethanol

To a solution of 2-bromo-1-(3'-nitrophenyl)ethanone (769 mg) and an asymmetric catalyst (100 mg, R-compound; produced by the firm Tokyo Kasei Kogyo) in anhydrous tetrahydrofuran (20 ml; prepared upon each use), there was added dropwise 2 M solution of boranedimethyl sulfide complex in tetrahydrofuran (2.16 ml; produced by the firm Aldrich) with agitation under cooling by an ice/salt refrigerant mixture over a periodof 5 minutes, followed by reaction and after-treatment, whereby the above-identified compound was obtained (768 mg).

Rf=0.72 (ethyl acetate/n-hexane=1/1)
Retention time: 9.00 minutes
Analysis conditions:
Column: CHIRALCEL AD (of the firm Daicel Chemical)
Mobile phase: n-hexane/ethanol 1/1
Flow rate: 0.5 ml/min.
Detection wave length: 254 nm
Temperature: 35° C.

Intermediate 45'

Synthesis of (R)-3-[2-iodo-1-(triethylsilyloxy)ethyl]-nitrobenzene

To a solution of the above intermediate 45 (768 mg) in acetone (30 ml), sodium iodode (2.96 g, a product of the firm Wako Pure Chemical Industries, Ltd.) was added, followed by reaction and after-treatment. The resulting iodide (795 mg) was dissolved in dimethylformamide (5 ml) together with imidazole (408.5 mg) and dimethylaminopyridine (24.4 mg), whereto triethylsilane chloride (452 mg) was added under ice-cooling, followed by reaction and after-treatment, whereby the above-identified compound was obtained (994 mg).

Rf=0.43 (ethyl acetate/n-hexane=1/3)

Intermediate 46

Synthesis of N-methyl-3-(2-bromoacetyl)benzenesulfonamide

A. Synthesis of N-methyl-3-acetylbenzenesulfonamide

To a solution of 3-acetylbenzenesulfonyl fluoride (2 g, a product of the firm Acros) in pyridine (20 ml), there was added a 40% solution of methylamine in methanol (2.02 ml, a product of the firm Wako Pure Chemical) and the mixture was agitated for 2 hours. Thereto was further added a 40% solution (2.02 ml) of methylamine in methanol and agitation was continued for further 40 minutes. 5 N hydrochloric acid and water (about 40 ml) were added to the reaction mixture to terminate the reaction (pH=4), whereupon the mixture was extracted with ethyl acetate. The organic layer was collected by phase separation, followed by drying and evaporating under reduced pressure, whereby the above-identified compound was obtained (996 mg).

Rf=0.64 (methanol/chloroform=1/10)

B. Synthesis of N-methyl-3-(2-bromoacetyl)benzenesulfonamide

To a solution of the above compound (990 mg) in 1,4-dioxane (15.8 ml) was added bromine (769 mg) and the mixture was agitated at 60° C. for 1 hour. The resulting mixture was concentrated under reduced pressure, whereupon water (18 ml) was added to the residue and the mixture was agitated vigorously under ice-cooling. The thereby formed precipitate was triturated and collected by filtration, followed by water wash. By drying at room temperature under reduced pressure, the above-identified compound was obtained (1.18 g).

Rf=0.63 (methanol/chloroform=1/10)

Intermediate 47

Synthesis of 1-(3,5-dinitrophenyl)ethanone

To a solution of dimethyl malonate (8 ml) in anhydrous tetrahydrofuran (70 ml), a 0.92 M solution of methylmagnesium bromide in tetrahydrofuran (78 ml, product of the firm Aldrich) was added dropwise at a temperature of −10° C. or lower over a period of 30 minutes under an argon atmosphere. Agitation was continued further for 15 minutes, whereupon a solution of 3,5-dinitrobenzoyl chloride (8.0 g, a product of the firm Tokyo Kasei Kogyo) in chloroform (35 ml) was added thereto dropwise over a period of 15 minutes. The reaction solution was brought back to room temeperature and agitation was continued for further 59 hours. The solvent was distilled off under reduced pressure and the resulting yellow amorphous substance (36.72 g) was dissolved in acetic acid (42 ml)/water (35 ml) mixture, whereto concentrated sulfuric acid (5 ml) was added and the solution was agitated for 5 hours under reflux with heating. The reaction mixture was poured onto 300 ml of the ice water and the deposited precipitate was collected, washed and dried at room temperature (6.35 g) under reduced pressure, whereupon the dried product was subjected to recrystallization from ethanol (5 ml) to obtain the above-identified compound (2.1 g).

Rf=0.79 (ethyl acetate/n-hexane=1/2)

Intermediate 48

Synthesis of 1-(3-amino-5-nitrophenyl)ethanone

To an agitated solution of the intermediate 47 (503 ml) in acetic acid (10 ml), there was added a solution of stannous chloride (1.43 g, anhydrous) in concentrated hydrochloric acid (5 ml) dropwise over a period of 5 minutes under cooling with ice/salt refrigerant mixture. The reaction mixture was removed from the cooling bath and stood to warm gradually upto room temperature, while continuing agitation for further 3 hours. The reaction mixture was poured into saturated aqueous sodium bicarbonate solution (100 ml) and the mixture was replenished further with saturated aqueous sodium bicarbonate solution so as to adjust the pH thereof at 8, whereupon the mixture was subjected to extraction with ethyl acetate (50 ml×3 times). The organic layer was washed with saturated aqueous sodium chloride solution and dried, whereupon the solvent was distilled off under reduced pressure to obtain the above-identified compound (160 mg).

Rf=0.51 (ethyl acetate/n-hexane=1/2)

Intermediate 49

Synthesis of 1-(3-hydroxy-5-nitrophenyl)ethanone

The intermediate 48 (350 mg) was dissolved in a sulfuric acid solution (prepared by adding 5 ml of concentrated sulfuric acid 5 ml of water), whereto an aqueous solution (5 ml) of sodium nitrite (140 mg) was added dropwise a period of 5 minutes with agitation under ice-cooling. After a further agitation for 25 minutes, the reaction mixture was supplemented with the above-mentioned sulfuric acid solution (10 ml) and the mixture was agitated for 30 minutes under reflux with heating at 120° C. After cooling down to room temperature, the mixture was extracted with ethyl acetate (40 ml×twice). The organic layer was dried and solvent was distilled off under reduced pressure, whereby a crude product was obtained (293 mg). By treating this crude product with a silica gel chrompatography (chloroform-methanol/chloroform=3/97-5/95), the above-identified compound was obtained (154 mg).

Rf=0.40 (methanol/chloroform=1/9)

Intermediate 50

Synthesis of 1-(3-benzyloxy-5-nitrophenyl)ethanone

The intermediate 49 (154 mg) was dissolved in anhydrous dimethylformamide (5 ml), whereto anhydrous potassium carbonate (360 mg), benzyl bromide (0.22 ml) and sodium iodide (130 mg) were added succeedingly and the mixture was agitated for 11.5 hours. To the reaction mixture, there were added 10 ml of water to terminate the reaction, whereto 50 ml of water were further added and the mixture was extracted with ethyl acetate (50 ml×twice). The organic layer was washed with water (100 ml) and saturated aqueous sodium chloride solution succeesingly and dried, whereupon the solvent was distilled off under reduced pressure, whereby a crude product was obtained (277 mg). By purifying this crude product with a silica gel chromatography (elution with ethyl acetate/n-hexane=1/9), the above-identified compound was obtained (140 mg).

Rf=0.91 (methanol/chloroform=1/9)

Intermediate 51

Synthesis of 1-(3-amino-5-benzyloxyphenyl)ethanone

The intermediate 50 (140 mg) was dissolved in methanol (20 ml), whereto platinum oxide (5 mg) was added under an argon atmosphere, where-the reaction system was replaced with hydrogen under ice-cooling, whereupon the reaction system was replaced with argon and thereto was added chloroform (20 ml). After removal of the catalyst by filtration, the above-identified compound was obtained (116 mg) by evaporating under reduced pressure.

Rf=0.82 (methanol/chloroform=1/9)

Intermediate 52

Synthesis of 1-[3-benzyloxy-5-[(methylsulfonyl)amino]phenyl]ethanone

From the intermediate 51 (116 mg) and methanesulfonyl chloride (40 μl), the above-identified compound was obtained (142 mg) by reaction and after-treatment in accordance with the method reported by A. A. Larsen et al in J. Med. Chem., 10, 462–472 (1967) and subsequent purification by a silica gel chromatography (elution with methanol/chloroform=5/95).

Rf=0.47 (methanol/chloroform=1/9)

Intermediate 53

Synthesis of 2-bromo-1-[3-benzyloxy-5-[(methylsulfonyl)amino]phenyl]ethanone

In the same manner as described in the synthesis of the intermediate 38, the above-identified compound was obtained (172 mg) from the intermediate 52 (140 mg) and cupric bromide (223 mg).

Rf=0.78 (ethyl acetate/n-hexane=1/1)

Intermediate 54

Synthesis of 1-[4-(ethoxycarbonyl)phenyl]ethanone ethylene acetal ethyl 4-acetyl-benzoate (9.61 g, a product of the firm Wako Pure Chemical Ind.) was dissolved in toluene (200 ml) under an argon atmosphere whereto ethylene glycol (20 ml) and p-toluenesulfonic acid hydrate (200 mg) were added, whereupon the mixture was refluxed with heating for 24 hours while dehydrating on a Dean-Stark apparatus. After cooling down to room temerature, the toluene layer was washed with water (100 ml×twice) and with saturated aqueous sodium chloride solution (100 ml) succeedingly, followed by drying and concentrating to dryness under reduced pressure, whereby the above-identified compound was obtained (12.76 g).

Rf=0.58 (ethyl acetate/m-hexane=1/2)

Intermediate 55

Synthesis of 1-[4-(hydroxymethyl)phenyl]ethanone

Litium aluminum hydride (1.90 g) was suspended in anhydrous tetrahydrofuran (120 ml) under an argon atmosphere, whereto a solution of the above intermediate 54 (12.76 g) in anhydrous tetrahydrofuran (40 ml) was added dropwise over a period of 15 minutes with ice-cooling, followed by agitation for further 90 minutes. Thereto was added gradually ethyl acetate (100 ml) over a period of 25 minutes to terminate the reaction, whereupon 1 N aqueous sulfuric acid (100 ml) was added thererto over a period of 30 minutes. Then, the reaction mixture was agitated at room temperature for 45 minutes, whereupon water (100 ml) was added thereto and the organic layer was collected by phase separation. The aqueous phase was extracted with ethyl acetate (100 ml×twice) and the organic phases were combined and washed with water (100 ml) and with saturated aqueous sodium chloride solution (100 ml) succeedingly, followed by drying and evaporating under reduced pressure. The residue (12.25 g) was dissolved in acetone (200 ml) and thereto was added p-toluensulfonic acid hydrate (200 mg), whereupon the mixture was agitated at room temperature for 20 hours. After confirmation of end of the reaction by $^1$H-NMR, the acetone solvent was distilled off under reduced pressure. The residue was subjected to partition between ethyl acetate (50 ml) and water (50 ml) whereupon the organic layer was collected by separation and washed with saturated aqueous sodium chloride solution, followed by drying and evaporating under reduced pressure, whereby the above-identified compound was obtained (6.688 g).

Rf=0.19 (ethyl acetate/n-hexane=1/2)

Intermediate 56

Synthesis of 1-[4-(acetoxymethyl)phenyl]ethanone

The intermediate 55 (6.67 g) was dissolved in pyridine (7.3 ml), whereto acetic anhydride (6.3 ml) was added and the mixture was agitated at room temperature for 12.5 hours. Thereto was added water (300 ml) to terminate the reaction, whereupon the mixture was extracted with ethyl acetate (50 ml). The aqueous layer was extracted with ethyl acetate (50 ml×twice) and the organic layer was combined and washed with water (100 ml), with 1 N aqueous hydrochloric acid (50 ml) and with saturated aqueous sodium chloride solution (50 ml) succeedingly, followed by drying and evaporating under reduced pressure, whereby the above-identified compound was obtained (8.27 g).

Rf=0.56 (ethyl acetate/n-hexane=1/1)

Intermediate 57

Synthesis of 1-[3-nitro-4-(acetoxymethyl)phenyl]ethanone

To fuming nitric acid (80 ml) cooled by ice/salt cooling mixture, intermediate 126 (8.09 g) was added all at once. After agitation for 10 minutes while maintaning the temperature as such, the reaction mixture was poured into an ice/water mixture (300 ml). The mixture was extracted with ethyl acetate (80 ml×3) and the organic layer was washed with water (100 ml×thrice), with saturated aqueous sodium bicarbonate solution and with saturated aqueous sodium chloride solution succeedingly, followed by drying and evaporating under reduced pressure. The residue (9.70 g) was purified by silica gel chromatography (ethyl acetate/n-hexane=1/2) to obtain the above-identified compound (8.41 g).

Rf=0.36 (ethyl acetate/n-hexane=1/2)

Intermediate 58

Synthesis of 1-[3-amino-4-(acetoxymethyl)phenyl]ethanone

The intermediate 57 (1.97 g) was dissolved in methanol (358 ml), whereto stannous chloride (10.55 g) and concentrated hydrochloric acid (7.5 ml) were added under an argon atmosphere and the mixture was agitated at room temperature for 2 hours. Thererto was added saturated aqueous sodium bicarbonate solution (200 ml) and the mixture was agitated at room temperature for 75 minutes, whereupon the deposited inorganic salt was filtered off with Celite and the filtrate was concentrated to about 200 ml under reduced pressure. This solution was extracted with ethyl acetate (300 ml) and the extract was washed with saturated aqueou sodium chloride solution, followed by drying and evaporating. The residue (1.32 g) was purified by silica gel chromatography (ethyl acetate/n-hexane=1/2) whereby the above-identified compound was obtained (0.56 g).

Rf=0.31 (ethyl acetate/n-hexane=1/2)

Intermediate 59

Synthesis of 1-[3-(methylsulfonyl)amino-4-(acetoxymethyl) phenyl]ethanone

The intermediate 58 (0.56 g) was dissolved in pyridine (3.6 ml), whereto methanesulfonyl chloride (215 μl) was added and mixture was agitated at room temperature for 26 hours. Thererto was added water (5 ml) and the mixture was extracted with ethyl acetate (20 ml×thrice), whereupon the organic phase was washed with 1 N aqueous hydrochloric acid (50 ml×twice) and with saturated aqueous sodium chloride solution succeedingly, followed by drying and evaporating under reduced pressure, whereby the above-identified compound was obtained (0.58 g).

Rf=0.39 (ethyl acetate/n-hexane=1/1)

Intermediate 60

Synthesis of 2-bromo-1-[3-(methylsulfonyl)amino-4-(acetoxymethyl) phenyl]ethanone In the same manner as described in the synthesis of the intermediate 38, the above-identified compound was produced (430 mg) from the intermediate 59 (285 mg) and cupric bromide (491 mg, a product of Kanto Chemical Co., Inc.).

Rf=0.44 (ethyl acetate/n-hexane=1/2)

Intermediate 61

Synthesis of 2-methoxy-5,6,7,8,9,10-hexahydro-cyclohepta[b]indole

Hydrochloride salt of 3-methoxyphenylhydrazine (2.62 g, a product of the firm Lancaster) and cycloheptanone (1.77 ml, a product of the firm Tokyo Kasei Kogyo) were dissolved in glacial acetic acid (30 ml), whereto a 4 N hydrogen chloride solution in 1,4-dioxane (1.77 ml, a product of the firm Aldrich) was added and the mixture was refluxed under an argon atmosphere with heating at 110° C. for 1 hour. The reaction mixture was poured into an ice/water mixture (300 ml), whereto 8 N aqueous sodium hydroxide was added carefully to adjust the pH at 6–7. whereupon the mixture was extracted with ethyl acetate (400 ml), followed by drying and evaporating. By purifying with a silica gel chromatography (ethyl acetate/n-hexane=1/5), the above-identified compound was obtained (1.29 g).

Rf=0.43 (ethyl acetate/n-hexane=1/3)

Intermediate 62

Synthesis of 2-hydroxy-5,6,7,8,9,10-hexahydro-cyclohepta[b]indole

To a solution of the intermediate 61 (1.29 g) in anhydrous dichloromethane (35 ml), 1 N boron tribromide solution in dichloromethane (18 ml) was added dropwise over a period of 5 minutes with agitation under an argon atmosphere while cooling with ice/salt refrigerant mixture. The mixture was agitated at this temperature for 7 minutes, whereupon the mixture was agitated for further 2.5 hours under ice-cooling. Thereto was added methanol (35 ml) dropwise carefully to terminate the reaction and the mixture was diluted with water (300 ml). This mixture was extracted with chloroform (200 ml×twice) and the combined organic phase was washed with saturated aqueous sodium chloride solution, followed by drying and evaporating under reduced pressure. After a further drying at room temperature under reduced pressure, the above-identified compound was obtained (1.23 g).

Rf=0.17 (ethyl acetate/n-hexane=1/3)

Intermediate 63

Synthesis of 2-(2-benzyloxycarbonylaminoethoxy)-5,6,7,8,9,10-hexahydro-cyclohepta[b]indole To a solution of the intermediate 62 (4.33 g) and the intermediate 1 (4.65 g) in acetone (20 ml), potassium carbonate (4.15 g) was added and the mixture was refluxed with heating at 60° C. for 22 hours. Thereto were added water and ethyl acetate to effect extraction, whereupon the organic layer was washed with saturated aqueous sodium chloride solution and dried, them the solvent was distilling off under reduced pressure. The residue was purified by a column chromatography (ethyl acetate/n-hexane=1/4). whereby the above-identified compound was obtained (969.3 mg).

Rf=0.48 (developed once with ethyl acetate/n-hexane=1/10, followed by one further development with ethyl acetate/n-hexane=1/1)

Intermediate 64

Synthesis of 2-(5,6,7,8,9,10-hexahydro-cyclohepta[b]indole-2-yloxy)ethylamine

To the intermediate 63 (969.3 mg), a 30% hydrogen bromide solution in acetic acid (10 ml) was added and the mixture was agitated at room temperature for 2.0 hours. Thereto was added diethyl ether and the deposited precipitate was collected by filtration and washed with diethyl ether. The precipitate was dissolved in water and the solution was adjusted at pH 10 by adding thereto 8 N aqueous NaOH, whereupon the solution was extracted with ethyl acetate three times. After drying the organic layer, the solvent was distilling off under reduced pressure, whereby the above-identified compound was obtained (579.7 mg).

Rf=0.14 (methanol/chloroform=1/10)

Intermediate 65

Synthesis of 4-acetylaminocyclohexanone

To an aqueous suspension (21.6 ml) of trans-4-acetamidocyclohexanol (20.85 g, a product of the firm Tokyo Kasei Kogyo), there was added with ice-cooling Jone's reagent, prepared from chromium trioxide (9.28 g), concentrated sulfuric acid (8.1 ml) and water (33.4 ml) under ice-cooling, over a period of 8 minutes. The mixture was agitated thereafter for 5 hours under ice-cooling, whereupon the mixture was stored in a refrigerator over two consecutive nights. This mixture was extractedwith chloroform (70 ml×ten times) and the extract was washed with saturated aqueous sodium bicarbonate solution, followed by drying and distilling off the solvent under reduced pressure. After a further drying under reduced pressure at room temperature, the above-identified compound was obtained (8.45 g).

Rf=0.40 (methanol/chloroform=1/10)

Intermediate 66

Synthesis of (±)-6-acetylamino-2-methoxy-5,6,7,8-tetrahydro-9H-carbazole

Hydrochloride salt of 3-methoxyphenylhydrazine (9.77 g, a product of the firm ACROS) and the intermediate 65 (8.58 g) were dissolve in ethanol (83 ml), whereto 4 N solution of hydrogen chloride in 1,4-dioxane (35 ml, a product of the firm Aldrich) was added, whereupon the mixture was refluxed with heating for three hours. The mixture was then cooled down to room temperature and the precipitate was filtered off, whereupon the solvent was distilled off from the filtrate under reduced pressure. Ethanol/n-heptane was added to the residue and the mixture was evaporated to dryness. The residue was dissolved in a small amount of ethanol and thereto was added water, whereupon the deposited precipitate was triturated and, then, collected by filtrtion, followed by washing with water and drying under reduced pressure at 42° C. This was triturated with a small amount of ethanol, whereupon it was crystallized out with ethyl acetate (200 ml) and the crystals were collected by filtration and washed with ethyl acetate, followed by drying under reduced pressure at room temperature, whereby the above-identified compound was obtained (5.188 g as a primary crystalline product).

Rf=0.45 (methanol/chloroform=1/10)

Intermediate 67

Synthesis of (±)-2-hydroxy-5,6,7,8-tetrahydro-6-acetylamino-9H-carbazole

To a solution of the intermediate 66 (246 mg) in anhydrous dichloromethane (20 ml), 1N solution (2.0 ml) of boron tribromide in dichloromethane was added dropwise over a period of 5 minutes under an argon atmosphere with cooling by ice/salt refrigerant mixture with agitation. At this temperature, the mixture was agitated for 2.75 hours. Methanol (10 ml) was added thereto dropwise carefully to terminate the reaction, whereupon the mixture was caused to warm to room temperature and was diluted with water (50 ml). This mixture was extracted with dichloromethane (50 ml×twice) and the combined organic layer was washed with saturated aqueous sodium chloride solution and dried, whereupon the solvent was distilled off under reduced pressure. By purifying on a silica gel column chromatography (methanol/chloroform=1/19-1/9). the above-identified compound was obtained (38 mg).

Rf=0.18 (methanol/chloroform=1/9)

Intermediate 68

Synthesis of 2-(2-benzyloxycarbonylaminoethoxy)-5,6,7,8-tetrahydro-6-acetylamino-9H-carbazole To a solution of the intermediate 67 (65 mg) and the intermediate 1 (217 mg) in acetone (10 ml), potassium carbonate (193 mg) was added and the mixture was held under reflux with heating at 60° C. for 19 hours. Thereto were added ethyl acetate (100 ml) and water (100 ml). After extraction, the organic layer was washed with saturated aqueous solution of sodium chloride and dried, whereupon the solvent was distilled off under reduced pressure. The residue was subjected to a preliminary purification by a column chromatography (chloroform-methanol/chloroform=1/100-5/95) and, then, to a final purification by PTLC (ethyl acetate/n-hexane=9/1), whereby the above-identified compound was obtained (10.1 mg).

Rf=0.26 (ethyl acetate/n-hexane=9/1)

EXAMPLE 1

(R)-N'-[5-[2-[2-(5,6,7,8-tetrahydro-9H-carbazol-2-yloxy)ethylamino]-1-hydroxyethyl]-2-benzyloxyphenyl]-N,N-dimethylsulfamide A. Synthesis of (R)-N'-[5-[2-[2-(5,6,7,8-tetrahydro-9H-carbazol-2-yloxy)ethylamino]-1-(triethylsilyloxy)ethyl]-2-benzyloxyphenyl]-N,N-dimethylsulfamide (intermediate 69)

A solution of the intermediate 3 (0.5 g), the intermediate 13 (1.2 4 g) and diisopropylethylamine (2.2 ml) in anhydrous dimethylacetamide (6.3 ml) was agitated at 50° C. under an argon atmosphere for 25 hours. After dilution with water (100 ml), it was extracted with ethyl acetate (50 ml×twice). The combined organic layer was washed with saturated aqueous sodium chloride and dried, whereupon the solvent was distilled off under reduced pressure. The residue was filtered with silica gel pad (eluted with ethyl acetate) and then purified by a silicagel chromatography (methanol/chloroform=1/20). whereby the above-identified compound was obtained (497.9 mg).

Rf=0.35 (methanol/chloroform=1/20)

B. Synthesis of (R)-N'-[5-[2-[2-(5,6,7,8-tetrahydro-9H-carbazol-2-yloxy)ethylamino]-1-hydroxyethyl]-2-benzyloxyphenyl]-N,N-dimethylsulfamide To a solution of the intermediate 69 (497.9 mg) in anhydrous tetrahydrofuran (26 ml), there were added glacial acetic acid (333 µl) and 1 N tetra-n-butyl-ammonium fluoride solution in tetrahydrofuran (5.2 ml) and the mixture was agitated at room temperature for 1.6 huors. After dilution with saturated aqueous sodium bicarbonate solution, the mixture was extracted with ethyl acetate. The organic layer was washed with saturated aqueous sodium chloride solution and dried, whereupon the solvent was distilled off under reduced pressure. After purification by a silica gel chromatography (methanol/chloroform=1/20 to 1/10), the above-identified compound was obtained (281.6 mg).

Rf=0.08 (methanol/chloroform=1/20)

EXAMPLE 2

(R)-N'-[5-[2-[2-(5,6,7,8-tetrahydro-9H-carbazol-2-yloxy)ethylamino]-1-hydroxyethyl]-2-hydroxyphenyl]-N,N-dimethylsulfamide hydrochloride The compound of Example 1 (281.6 mg) was dissolved in anhydrous dichloromethane (20 ml) and the solution was cooled under an argon atmosphere to −70° C., whereupon 1 N boron tribromide solution in dichloromethane (1.3 ml) was added thereto dropwise over a period of 3 minutes with agitation. After agitation for two hour, methanol (20 ml) was added thereto dropwise carefully to terminate the reaction, whereupon the mixture was dilluted with water (200 ml) after it had been warmed to room temperature. The mixture was then washed with diethyl ether (200 ml) and the aqueous layer was extracted with ethyl acetate (200 ml×twice) after it had been adjusted at pH 10 with 8 N aqueous sodium hydroxide solution. The organic layer was washed with saturated aqueous sodium chloride solution and dried, whereupon the solvent was distilled off under reduced pressure. After purification by a silica gel chromatography (ammonia solution/methanol/chloroform=1/9/100) and conversion to hydrochloride salt with 0.1 N hydrogen chloride solution in ethanol, the above-identified compound was obtained (94.6 mg).

Rf=0.07 (methanol/chloroform=1/10)

Retention time: 14.6 min. for R-compound (17.0 min. for S-compound)

Analysis condition:

Column: 4.6 mm ID×150 mm; CHIRALCEL OJ-R (of the firm Daicel Chemical); two sets Mobile phase: 0.5 M NaClO4-HClO4 buffer solution (pH 2.0)/acetonitrile=6/4

Flow rate: 0.5 ml/min.

Detection wave length: 254 nm

Temperature: 40° C.

EXAMPLE 3

(S)-N'-[5-[2-[2-(5,6,7,8-tetrahydro-9H-carbazol-2-yloxy)ethylamino]-1-hydroxyethyl]-2-hydroxyphenyl]-N,N-dimethylsulfamide hydrochloride The reaction and after-treatment were carried out in the same manner as in the synthesis of the compounds in Example 1 and 2 using the intermediate 14 and intermediate 3, whereby the above-identified compound was obtained.

MS: 489 (MH+)

Retention time: (14.6 min. for R-compound) 17.0 min. for S-compound)

Analysis condition:

Column: 4.6 mm ID×150 mm; CHIRALCEL OJ-R (of the firm Daicel Chemical); two sets Mobile phase: 0.5 M NaClO4-HClO4 buffer solution (pH 2.0)/acetonitrile=6/4

Flow rate: 0.5 ml/min.

Detection wave length: 254 nm

Temperature: 40° C.

EXAMPLE 4

(±)-N'-[5-[2-[2-(5,6,7,8-tetrahydro-9H-carbazol-2-yloxy)ethylamino]-1-hydroxyethyl]-2-hydroxyphenyl]-N,N-dimethylsulfamide hydrochloride The reaction and after-treatment were carried out in the same manner as in the synthesis of the compounds in Example 1 and 2 using the intermediate 12 (590.6 mg) and intermediate 3 (277 mg), whereby the above-identified compound was obtained (14.2 mg).

Rf=0.07 (methanol/chloroform=1/10), MS: 489 (MH+)

EXAMPLE 5

(R)-N-[5-[2-[2-(5,6,7,8-tetrahydro-9H-carbazol-2-yloxy) ethylamino]-1-hydroxyethyl]-2-benzyloxyphenyl] methanesulfonamide hydrochloride A. Synthesis of
(R)-N,N-[[2-(5,6,7,8-tetrahydro-9H-carbazol-2-yloxy) ethyl]-[2-(triethylsilyloxy)-2-[3-nitro-4-(benzyloxy) phenyl]]ethyl]amine (intermediate 70)

A solution of the intermediate 9 (770 mg), the intermediate 3 (350 mg) and Huhnig's base (1.3 ml, a product of the firm Aldrich) in dimethylacetamide (5 ml) was agitated at 70° C. for 7 hours, followed by further agitation at room temperature for 13.6 hours. To the reaction solution, there were added ethyl acetate (30 ml) and water (50 ml) to effect extraction. The aqueous layer was further extracted with ethyl acetate (30 ml). The combined organic layer was washed with water and with saturated aqueous sodium chloride solution succeedingly and was dried, whereupon the solvent was distilled off under reduced pressure. The residue was purified by a column chromatography (ethyl acetate/n-hexane=1/1 to 1/2), whereby the above-identified compound was obtained (334 mg).

Rf=0.41 (methanol/chloroform=1/19)

B. Synthesis of
(R)-N,N,N-[(benzyloxycarbonyl)-[2-(5,6,7,8-tetrahydro-9H-carbazol-2-yloxy)ethyl]-[2-(triethylsilyloxy)-2-[3-nitro-4-(benzyloxy)phenyl]]ethyl]amine (intermediate 71)

The intermediate 70 (148 mg) was dissolved in methylene chloride (10 ml) under an argon atmosphere and thereto was added triethylamine (60 µl), whereto benzyl chloroformate (0.2 ml, a product of the firm Aldrich) was added under ice-cooling with agitation. After agitation 30 minutes was continued at room temperature for further 5.3 hours. The mixture was diluted with saturated aqueous sodim bicarbonate solution (20 ml) and was extracted with chloroform (20 ml×twice). The combined organic layer was washed with saturated aqueous sodium chloride solution and dried, whereupon the solvent was distilled off under reduced pressure. The residue was purified by a column chromatography (ethyl acetate/n-hexane=1/2), whereby the above-identified compound was obtained (78 mg).

Rf=0.67 (ethyl acetate/n-hexane=1/1

C. Synthesis of
(R)-N,N,N-[(benzyloxycarbonyl)-[2-(5,6,7,8-tetrahydro-9H-carbazol-2-yloxy)ethyl]-[2-(triethylsilyloxy)-2-[3-amino-4-(benzyloxy)phenyl]]ethyl]amine (intermediate 72)

To an argon-replaced solution of intermediate 71 (65 mg) in methanol (6 ml), there was added under ice-cooling platinum oxide (anhydrous, 6 mg, a product of the firm Wako Pure Chemical) and reduction was effected with hydrogen gas of 1 atm. After agitation for 3.4 hours, the reaction system was replaced with argon, whereupon the reaction mixture was diluted with chloroform and the catalyst was removed by filtration. By evaporating under reduced pressure, followed by purification by a silica gel chromatography (ethyl acetate/n-hexane=1/4 to 1/3) the above-identified compound was obtained (32 mg).

Rf=0.12 (ethyl acetate/n-hexane=1/4)

D. Synthesis of
(R)-N-[5-[2-[(benzyloxycarbonyl)-[2-(5,6,7,8-tetrahydro-9H-carbazol-2-yloxy)ethyl]amino]-1-(triethylsilyloxy)ethyl]-2-(benzyloxy)phenyl] methanesulfonamide (intermediate 73)

To a solution of the intermediate 72 (183 mg) in pyridine (1 ml), there was added methanesulfonyl chloride (20 µl) at room temperature and the mixture was agitated for 1 hour. Thereto was added water and agitation was continued for 3 hours, whereupon the mixture was ice-cooled and the thereby deposited precipitated was collected by filtration. This precipitated was dissolved in ethyl acetate and the organic layer was washed with saturated aqueous sodium chloride solution and dried, whereupon the solvent was distilled off under reduced pressure. After purification by a silica gel chromatography (ethyl acetate/n-hexane=1/4 to 1/2), the above-identified compound was obtained (192 mg).

Rf=0.54 (ethyl acetate/n-hexane=1/2)

E. Synthesis of
(R)-N-[5-[2-[2-(5,6,7,8-tetrahydro-9H-carbazol-2-yloxy) ethylamino]-1-hydroxyethyl]-2-benzyloxyphenyl] methanesulfonamide hydrochloride The intermediate 73 (192 mg) was admixed at room temperature to 30% solution (4 ml) of hydrogen bromide in acetic acid the mixture was agitated for 1 hours, whereupon the mixture was diluted with diethyl ether and further agitated. The deposited precipitate was collected by filtration and washed with diethyl ether, whereupon it was dissolved in water. After adjusting the pH thereof at 10 with 8 N aqueous sodium hydroxide, the solution was extracted with ethyl acetate twice, followed by washing with saturated aqueous sodium chloride solution and drying, whereupon the solvent was distilled off under reduced pressure. By purifying by a silica gel chromatography (methanol/chloroform=5/95 to 7/93) and converting into hydrochloride salt with 0.1 N hydrogen chloride solution in ethanol, the above-identified compound was obtained (105.9 mg).

Rf=0.34 (methanol/chloroform=1/9)

EXAMPLE 6

(R)-N-[5-[2-[2-(5,6,7,8-tetrahydro-9H-carbazol-2-yloxy) ethylamino]-1-hydroxyethyl]-2-hydroxyphenyl] methanesulfonamide hydrochloride The free base of the compound of Example 5 (378 mg) was subjected CA to reaction and after-treatment in accordance with the procedures of synthesis of the compound in Example 2 and, by conversion into the hydrochloride salt in an ordinary practice, the above-identified compound was obtained (178 mg).

Rf=0.03 (methanol/chloroform=1/9)

Retention time: 29.1 min. for R-compound (34.0 min. for S-compound)

Analysis condition:
Column: CHIRALCEL OJ-R (of the firm Daicel Chemical); two sets
Mobile phase: 0.5 M NaClO4-HClO4 buffer solution (pH 2.0)/CH3CN =70/30
Flow rate: 0.5 ml/min.
Pressure: 56 kg/cm$^2$
Detection wave length: 254 nm
Temperature: 40° C.

EXAMPLE 7

(S)-N-[5-[2-[2-(5,6,7,8-tetrahydro-9H-carbazol-2-yloxy) ethylamino]-1-hydroxyethyl]-2-hydroxyphenyl] methanesulfonamide hydrochloride The reaction and after-treatment were carried out in the same manner as in the synthesis of the compounds in Examples 5 and 6 using the intermediate 3 and intermediate 10, whereby the above-identified compound was obtained. MS: 460 (MH+)

Retention time: 29.1 min. for R-compound (34.0 min. for S-compound)

Analysis condition:
Column: CHIRALCEL OJ-R (of the firm Daicel Chemical); two sets
Mobile phase: 0.5 M NaClO4-HClO4 buffer solution (pH 2.0)/CH3CN=70/30
Flow rate: 0.5 ml/min.
Pressure: 56 kg/cm$^2$
Detection wave length: 254 nm
Temperature: 40° C.

EXAMPLE 8

(±)-N-[5-[2-[2-(5,6,7,8-tetrahydro-9H-carbazol-2-yloxy) ethylamino]-1-hydroxyethyl]-2-hydroxyphenyl] methanesulfonamide hydrochloride The intermediate 3 and the racemic modification of the intermediate 9 (prepared from the starting intermediate corresponding to intermediate 8, which was obtained without using the asymmetric catalyst using 1 M solution of borane-tetrahydrofuran complex in tetrahydrofuran as the agent) were subjected to reaction and after-treatment in accordance with the synthesis procedures of Examples 5 and 6, whereby the above-identified compound was synthesized.

Rf=0.03 (methanol/chloroform=1/9), MS: 460 (MH+)

EXAMPLE 9

(R)-N-[5-[2-[2-(5,6,7,8-tetrahydro-9H-carbazol-2-yloxy) ethylamino]-1-hydroxyethyl]-2-fluorophenyl] methanesulfonamide hydrochloride
A. (R)-N-[5-[2-[2-(5,6,7,8-tetrahydro-9H-carbazol-2-yloxy) ethylamino]-1-[(triethylsilyl)oxy]ethyl]-2-fluorophenyl] methanesulfonamide (intermediate 74)

A solution of the intermediate 21 (429.7 mg), the intermediate 3 (250 mg) and Huhnig's base (945 µl, a product of the firm Aldrich) in dimethylacetamide (2 ml) was agitated at 60° C. for 10 hours. To the reaction solution, there were added ethyl acetate and water to effect extraction and organic layer was washed with saturated aqueous sodium chloride solution and dried, whereupon the solvent was distilled off under reduced pressure. The residue was purified by a column chromatography (chloroform-methanol/chloroform=1/100), whereby the above-identified compound was obtained (210.6 mg).

Rf=0.60 (methanol/chloroform=1/10)
B. Synthesis of
(R)-N-[5-[2-[2-(5,6,7,8-tetrahydro-9H-carbazol-2-yloxy) ethylamino]-1-hydroxyethyl]-2-fluorophenyl] methanesulfonamide hydrochloride To a solution of the intermediate 74 (199.5 mg) in anhydrous tetrahydrofuran (11 ml), acetic acid (146g 1) and 1 M solution (2.28 ml) of tetrabutylammonium fluoride in tetrahydrofuran were added and the mixture was agitated at room temperature for 80 minutes. The reaction mixture was diluted with ethyl acetate and washed with saturated aqueous sodium chloride solution, followed by drying, whereupon the solvent was distilled off under reduced pressure. The residue was purified by a silica gel chromatography (methanol/chloroform=1/20), whereby the product was obtained as free amide (158.7 mg).

Rf=0.20 (methanol/chloroform=1/10)

To this product was added 0.1N solution of hydrogen chloride in ethanol (in an amount of 1.1 equivalent) to convert it into a hydrochloride salt, followed by evaporating under reduced pressure. To the residue, diethyl ether was added and the thereby precipitate was collected by filtration and dried under reduced pressure at 50° C. to obtain the above identified compound (138.6 mg) as a powdery product.

Retention time: 16.7 min. for R-compound (26.1 min. for S-compound)

Analysis condition:
Column: 4.6 mm ID×250 mm; CHIRALPAK AD (of the firm Daicel Chemical); single set
Mobile phase: hexane/ethaol (3/7)
Flow rate: 0.5 ml/min.
Detection wave length: 254 nm
Temperature: room temperature

EXAMPLE 10

(S)-N-[5-[2-[2-(5,6,7,8-tetrahydro-gH-carbazol-2-yloxy) ethylamino]-1-hydroxyethyl]-2-fluorophenyl] methanesulfonamide hydrochloride Using the intermediate 23 and the intermediate 3, the above-identified compound was obtained in accordance with the procedures described in Example 9.

Rf=0.20 (methanol/chloroform 1/10) MS: 462 (MH+)

Retention time: (16.7 min. for R-compound) 26.1 min. for S-compound

Analysis condition:
Column: 4.6 mm ID×250 mm; CHIRALPAK AD (of the firm Daicel Chemical); single set
Mobile phase: hexane/ethaol (3/7)
Flow rate: 0.5 ml/min.
Detection wave length: 254 nm
Temperature: room temperature

EXAMPLE 11

(±)-N-[5-[2-[2-(5,6,7,8-tetrahydro-9H-carbazol-2-yloxy) ethylamino]-1-hydroxyethyl]-2-fluorophenyl] methanesulfonamide hydrochloride Using the intermediate 19 and the intermediate 3, the above-identified compound was obtained in accordance with the procedures described in Example 9.

Rf=0.20 (methanol/chloroform=1/10) MS: 462 (MH+)

EXAMPLE 12

(R)-N-[5-[2-[2-(5,6,7,8-tetrahydro-9H-carbazol-2-yloxy) ethylamino]-1-hydroxyethyl]-2-chlorophenyl] methanesulfonamide hydrochloride
A. (R)-N-[5-[2-[2-(5,6,7,8-tetrahydro-9H-carbazol-2-yloxy) ethylamino}-1-[(triethylsilyl)oxy]ethyl]-2-chlorophenyl] methanesulfonamide (intermediate 75)

A solution of the intermediate 29 (850.8 mg), the intermediate 3 (400 mg) and Huhnig's base (2.0 ml, a product of the firm Aldrich) in dimethylacetamide (5.2 ml) was agitated at 60° C. for 11 hours. To the reaction solution, there were added ethyl acetate (100 ml) and water (100 ml) to effect extraction and the organic layer was washed with saturated aqueous sodium chloride solution and dried, whereupon the solvent was distilled off under reduced pressure. The residue was purified by a column chromatography (chloroform-3% methanol/chloroform), whereby the above-identified compound was obtained (330 mg).

Rf=0.44 (methanol/chloroform=1/10)
B. Synthesis of
(R)-N-[5-[2-[2-(5,6,7,8-tetrahydro-9H-carbazol-2-yloxy) ethylamino]-1-hydroxyethyl]-2-chlorophenyl] methanesulfonamide hydrochloride To a solution of the intermediate 75 (330 mg) in anhydrous tetrahydrofuran (20 ml), acetic acid (120 µl) and 1 M solution (874g 1) of tetrabutylammonium fluoride in tetrahydrofuran were added and the mixture was agitated at room temperature for 70 minutes. The reaction mixture was diluted with ethyl acetate (200 ml) and washed with saturated aqueous sodium bicarbonate solution (200 ml) and, then, with saturated aqueous sodium chloride solution, followed by drying, whereupon the solvent was distilled off under reduced pressure. The residue was purified by a silica gel chromatography (chloroform-5% methanol/chloroform), whereby the product was obtained as free amide (196 mg).

Rf=0.22 (methanol/chloroform=1/10)

To this product was added 0.1 N solution of hydrogen chloride in ethanol (in an amount of 1.1 equivalent) to convert it into a hydrochloride salt, followed by evaporating under reduced pressure. To the residue, diethyl ether was added and the thereby deposited precipitate was collected by filtration and dried under reduced pressure at 50° C. to obtain the above-identified compound (208.5 mg) as a powderly product.

Retention time: 20.8 min. for R-compound (27.0 min. for S-compound)

Analysis condition:

Column: 4.6 mm ID×250 mm; CHIRALPAK AD (of the firm Daicel Chemical); single set Mobile phase: hexane/ethaol (3/7)

Flow rate: 0.5 ml/min.

Detection wave length: 254 nm

Temperature: room temperature

EXAMPLE 13

(S)-N-[5-[2-[2-(5,6,7,8-tetrahydro-9H-carbazol-2-yloxy)ethylamino]-1-hydroxyethyl]-2-chlorophenyl]methanesulfonamide hydrochloride Using the intermediate 31 and the intermediate 3, the above-identified compound was obtained in accordance with the procedures described in Example 9.

Rf=0.22 (methanol/chloroform=1/10) MS: 478 (MH+)

Retention time: (20.8 min. for R-compound) 27.0 min. for S-compound

Analysis condition:

Column: 4.6 mm ID×250 mm; CHIRALPAK AD (of the firm Daicel Chemical); single set Mobile phase: hexane/ethaol (3/7)

Flow rate: 0.5 ml/min.

Detection wave length: 254 nm

Temperature: room temperature

EXAMPLE 14

(±)-N-[5-[2-[2-(5,6,7,8-tetrahydro-9H-carbazol-2-yloxy)ethylamino]-1-hydroxyethyl]-2-chlorophenyl]methanesulfonamide hydrochloride The intermediate 27 was synthesized in accordance with the procedures of synthesis of the intermediates 11 and 12, whereby (±)-N-[5-[2-iodo-1-(triethylsilyloxy)ethyl]-2-chlorophenyl]methanesulfonamide was obtained. Using this intermediate and the intermediate 3, the above -identified compound was obtained in accordance with the procedures described in Example 12.

Rf=0.22 (methanol/chloroform=1/10) MS: 478 (MH+)

EXAMPLE 15

(R)-N-[5-[2-[2-(5,6,7,8-tetrahydro-9H-carbazol-2-yloxy)ethylamino]-1-hydroxyethyl]-2-bromophenyl]methanesulfonamide hydrochloride A. (R)-N-[5-[2-[2-(5,6,7,8-tetrahydro-9H-carbazol-2-yloxy)ethylamino]-1-[(triethylsilyl)oxy]ethyl]-2-bromophenyl]methanesulfonamide (intermediate 76)

A solution of the intermediate 35 (482.7 mg), the intermediate 3 (250 mg) and Huhnig's base (945 µl, a product of the firm Aldrich) in dimethylacetamide (2 ml) was agitated at 60° C. for 10 hours. To the reaction mixture, there were added ethyl acetate and water to effect extraction and the organic layer was washed with saturated aqueous sodium chloride solution and dried, whereupon the solvent was distilled off under reduced pressure. The residue was purified by a column chromatography (methanol/chloroform=1/100), whereby the above-identified compound was obtained (225.0 mg).

Rf=0.66 (methanol/chloroform=1/10)

B. Synthesis of
(R)-N-[5-[2-[2-(5,6,7,8-tetrahydro-9H-carbazol-2-yloxy)ethylamino]-1-hydroxyethyl]-2-bromophenyl]methanesulfonamide hydrochloride To a solution of the intermediate 76 (218.5 mg) in anhydrous tetrahydrofuran (11 ml), acetic acid (144µl) and 1 M solution (2.26 ml) of tetrabutylammonium fluoride in tetrahydrofuran were added and the mixture was agitated at room temperature for 80 minutes. The reaction mixture was diluted with ethyl acetate and washed with saturated aqueous sodium bicarbonate solution (15 ml) and, then, with saturated aqueous sodium chloride solution, followed by drying, whereupon the solvent was distilled off under reduced pressure. The residue was purified by a silica gel chromatography (methanol/chloroform=1/10), whereby the product was obtained as free amide (151.9 mg).

Rf=0.28 (methanol/chloroform=1/10)

To this product was added 0.1 N solution of hydrogen chloride in ethanol (in an amount of 1.1 equivalent) to convert it into a hydrochloride salt, followed by evaporating under reduced pressure. To the residue, diethyl ether was added and the thereby deposited precipitate was collected by filtration and dried under reduced pressure at 50° C. to obtain the above-identified compound (138.6 mg) as a powderly product.

Retention time: 22.7 min. for R-compound (29.2 min. for S-compound)

Analysis condition:

Column: 4.6 mm ID×250 mm; CHIRALPAK AD (of the firm Daicel Chemical); single set Mobile phase: hexane/ethaol (3/7)

Flow rate: 0.5 ml/min.

Detection wave length: 254 nm

Temperature: room temperature

EXAMPLE 16

(±)-N-[5-[2-[2-(5,6,7,8-tetrahydro-9H-carbazol-2-yloxy)ethylamino]-1-hydroxyethyl]-2-bromophenyl]methanesulfonamide hydrochloride The intermediate 33 was synthesized in accordance with the procedures of synthesis of the intermediates 11 and 12, whereby (±)-N-[5-[2-iodo-1-(triethylsilyloxy)ethyl]-2-bromophenyl]methanesulfonamide was obtained. Using this intermediate and the intermediate 3, the above-identified compound was obtained in accordance with the procedures described in Example 15.

Rf=0.28 (methanol/chloroform=1/10) MS: 524 (MH+)

EXAMPLE 17

(±)-N-[3-[2-[2-(5,6,7,8-tetrahydro-9H-carbazol-2-yloxy)ethylamino]-1-hydroxyethyl]phenyl]methanesulfonamide hydrochloride A. (±)-N-[3-[2-[2-(5,6,7,8-tetrahydro-9H-carbazol-2-yloxy) ethylamino]-1-[(triethylsilyl)oxy]ethyl]phenyl] methanesulfonamide (intermediate 77)

A solution of the intermediate 44 (494.4 mg), the intermediate 3 (250 mg) and Huhnig's base (1.92 ml, a product of the firm Aldrich) in dimethylacetamide (3.26 ml) was agitated at 60° C. for 4.5 hours. To the reaction solution, there were added ethyl acetate (80 ml) and water (80 ml) to effect phase extraction and the organic layer was washed with saturated aqueous sodium chloride solution and dried, whereupon the solvent was distilled off under reduced pressure. The residue was purified by a column chromatography (chloroform-3% methanol/chloroform), whereby the above-identified compound was obtained (149.6 mg).

Rf=0.39 (methanol/chloroform=1/10)

B. (+)-N-[3-[2-[2-(5,6,7,8-tetrahydro-9H-carbazol-2-yloxy) ethylamino]-1-hydroxyethyl]phenyl]methanesulfonamide hydrochloride To a solution of the intermediate 77 (149.6 mg) in anhydrous tetrahydrofuran (9.4 ml), acetic acid (51 µl) and 1 M solution (420µl) of tetrabutylammonium fluoride in tetrahydrofuran were added and the mixture was agitated at room temperature for 15 hours. The reaction mixture was diluted with ethyl acetate and washed with saturated aqueous sodium bicarbonate solution and, then, with saturated aqueous sodium chloride solution, followed by drying, whereupon the solvent was distilled off under reduced pressure. The residue was purified by a silica gel chromatography (chloroform-10% methanol/chloroform), whereby the product was obtained as free amide (110.7 mg).

Rf=0.18 (methanol/chloroform=1/10)

To this product was added 0.1 N solution of hydrogen chloride in ethanol (in an amount of 1.1 equivalent) to convert it into a hydrochloride salt, followed by evaporating under reduced pressure and drying under reduced pressure at 50° C., whereby the above-identified compound was obtained (115 mg).

EXAMPLE 18

(R)-N-[3-[2-[2-(5,6,7,8-tetrahydro-9H-carbazol-2-yloxy) ethylamino]-1-hydroxyethyl]phenyl]methanesulfonamide hydrochloride From the intermediates 45' and 3, the above-identified compound was obtained in accordance with the procedures described in Example 6.

Rf=0.18 (methanol/chloroform=1/10) MS: 444 (MH+)

Retention time: 16.3 min. for R-compound (24.1 min. for S-compound)

Analysis condition:
Column: 4.6 mm ID×250 mm; CHIRALPAK AD (of the firm Daicel Chemical); single set
Mobile phase: hexane/ethaol (3/7)
Flow rate: 0.5 ml/min.
Detection wave length: 254 nm
Temperature: room temperature

EXAMPLE 19

(S)-N-[3-[2-[2-(5,6,7,8-tetrahydro-9H-carbazol-2-yloxy) ethylamino]-1-hydroxyethyl]phenyl]methanesulfonamide hydrochloride Reaction and after-treatment were carried out in accordance with the procedures synthesis of the intermediates 8 and 9, except that an S-form asymmetric catalyst (a product of the firm Tokyo Kasei Kogyo) and 2-bromo-1-(3'-nitrophenyl)ethanone were used, whereby (S)-3-[2-iodo-1-(triethylsilyloxy)ethyl]nitrobenzene was obtained. From the above intermediate and the intermediate 3, the above-identified compound was obtained in accordance with the procedures described in Example 6.

Rf=0.18 (methanol/chloroform 1/10) MS : 444 (MH+)

Retention time: (16.3 min. for R-compound) 24.1 min. for S-compound)

Analysis condition:
Column: 4.6 mm ID×250 mm; CHIRALPAK AD (of the firm Daicel Chemical); single set
Mobile phase: hexane/ethaol (3/7)
Flow rate: 0.5 ml/min.
Detection wave length: 254 nm
Temperature: room temperature

EXAMPLE 20

(R)-N-methyl-[5-[2-[2-(5,6,7,8-tetrahydro-9H-carbazol-2-yloxy)ethylamino]-1-hydroxyethyl]-2-chloro] benzenesulfonamide hydrochloride A. Synthesis of
(R)-N-methyl-[5-[2-[2-(5,6,7,8-tetrahydro-9H-carbazol-2-yloxy)ethylamino}-1-[(triethylsilyl)oxy]ethyl]-2-chloro] benzenesulfonamide (intermediate 78)

A solution of the intermediate 43 (735 mg), the intermediate 3 (35 0 mg) and Huhnig's base (1.3 ml, a product of the firm Aldrich) in dimethylacetamide (5 ml) was agitated at 60° C. for 4 hours. To the reaction solution, there were added ethyl acetate and water to effect extraction and the organic layer was washed with saturated aqueous sodium chloride solution and dried, whereupon the solvent was distilled off under reduced pressure. The residue was roughly purified by a column chromatography (chloroform-2% methanol/chloroform) and, then, purified by a column chromatography (ethyl acetate/n-hexane 7/3), whereby the above-identified compound was obtained (142 mg).

Rf=0.28 (methanol/chloroform=1/9)

Retention time: 16.9 min. for R-compound (25.3 min. for S-compound)

Analysis condition:
Column: 4.6 mm ID×150 mm; CHIRALPAK AD (of the firm Daicel Chemical); single set
Mobile phase: n-hexane/ethaol (3/7)
Flow rate: 0.5 ml/min.
Detection wave length: 254 nm
Temperature: room temperature B. (R)-N-methyl-[5-[2-[2-(5,6,7,8-tetrahydro-9H-carbazol-2-yloxy)ethylamino]-1-hydroxyethyl]-2-chloro] benzenesulfonamide hydrochloride To a solution of the intermediate 78 (140 mg) in anhydrous tetrahydrofuran (3 ml), acetic acid (90 µl) and 1 M solution (1.56 ml) of tetrabutylammonium fluoride in tetrahydrofuran were added and the mixture was agitated at room temperature for 3.5 hours. The reaction mixture was diluted with ethyl acetate and washed with saturated aqueous sodium bicarbonate solution and, then, with saturated aqueous sodium chloride solution, followed by drying, whereupon the solvent was distilled off under reduced pressure. The residue was purified by a silica gel chromatography (7% methanol/chloroform), whereby the product was obtained as free amide (148 mg).

Rf=0.24 (methanol/chloroform=1/9)

To this product was added 0.1 N solution of hydrogen chloride in ethanol (in an amount of 1.1 equivalent) to convert it into a hydrochloride salt, followed by evaporating under reduced pressure. To the residue, methanol diethyl ether was added and the thereby deposited precipitate was collected by filtration and was dried under reduced pressure at 50° C., whereby the above-identified compound was obtained (61 mg).

EXAMPLE 21

(R)-N'-[5-[2-[2-(6,7,8,9-tetrahydrodibenzofuran-3-yloxy) ethylamino]-1-hydroxyethyl]-2-benzyloxyphenyl]-N,N-dimethylsulfamide A. Synthesis of
(R)-N'-[5-[2-[2-(6,7,8,9-tetrahydrodibenzofuran-3-yloxy) ethylamino]-1-(triethylsilyloxy)ethyl]-2-benzyloxyphenyl]-N,N-dimethylsulfamide (intermediate 79)

A solution of the intermediate 5 (2.14 g), the intermediate 13 (5. 47 g) and diisopropylethylamine (11 ml) in anhydrous dimethylacetamide (31.5 ml) was agitated under an argon atmosphere at 50° C. for 25 hours. After dilution with ethyl acetate (300 ml), washing with saturate aqueous sodium chloride solution (200 ml×thrice) and drying of the organic phase, the solvent was distilled off under reduced pressure. The residue was subjected to filtration through a silica gel pad (elution with ethyl acetate), followed by purification by a silica gel chromatography (methanol/chloroform=1/20), whereby the above-identified compound was obtained (2.05 g).

Rf=0.60 (methanol/chloroform=1/20)

B. Synthesis of
R)N-[5-[2-[2-(6,7,8,9-tetrahydrodibenzofuran-3-yloxy) ethylamino]-1-hydroxyethyl]-2-benzyloxyphenyl]- N,N-dimethylsulfamide To a solution of the intermediate 79 (2.05 g) in anhydrous tetrahydrofuran (100 ml), glacial acetic acid (1.25 ml) and 1 N solution (19.5 ml) of tetrabutylammonium fluoride in tetrahydrofuran were added and the mixture was agitated at room temperature for 2.4 hours. After dilution with saturated sodium bicarbonate solution and extraction with ethylacetate, the organic phase was washed with saturated aqueous sodium chloride solution, followed by drying, whereupon the solvent was distilled off under reduced pressure. By purifying by a silica gel column chromatography (methanol/chloroform=3/97-5/95), the above-identified compoud was obtained (1.42 g).

Rf=0.25 (methanol/chloroform=1/20)

EXAMPLE 22

(R)-N'-[5-[2-[2-(6,7,8,9-tetrahydrodibenzofuran-3-yloxy) ethylamino]-1-hydroxyethyl]-2-hydroxyphenyl]-N,N-dimethylsulfamide hydrochloride The compound (1.13 g) of Example 21 was dissolved in anhydrous dichloromethane (76 ml) and cooled down to −70° C. under an argon atmosphere, whereto 1 N solution (5.3 ml) of boron tribromide in dichloromethane was added dropwise with agitation over a period of 5 minutes. After agitation for 2 hours, methanol (50 ml) was added dropwise thereto carefully to terminate the reaction and the mixture was caused to elevate its temperature up to room temperature, before it was diluted with water (500 ml). After washing with diethyl ether (400 ml), the aqueous phase was adjusted at pH 10 by 8 N aqueous sodium hydroxyde solution and was extracted with ethyl acetate (250 ml×thrice). The organic layer was washed with saturated aqueous sodium chloride solution and dried, whereupon the solvent was distilled off under reduced pressure. By purifying with a silica gel column chromatography (methanol/chroloform 3/97-5/95) and converting into hydrochloride salt with 0.1 N solution of hydrogen chloride in ethanol, the above-identified compound was obtained (498.5 mg).

Rf=0.11 (methanol/chloroform=1/10)

Retention time: 17.8 min. for R-compound (21.4 min. for S-compound)

Analysis condition:
Column: 4.6 mm ID×150 mm; CHIRALCEL OJ-R (of the firm Daicel Chemical); two sets
Mobile phase: 0.5M NaCl04-HCl04 buffer (pH 2.0)/ acetonitrile (6/4)
Flow rate: 0.5 ml/min.
Detection wave length: 254 nm
Temperature: 40° C.

EXAMPLE 23

(S)-N'-[5-[2-[2-(6,7,8,9-tetrahydrodibenzofuran-3-yloxy) ethylamino]-1-hydroxyethyl]-2-hydroxyphenyl]-N,N-dimethylsulfamide hydrochloride The intermediates 14 and 5 were reacted and after-treated as in the synthesis of the compounds of Examples 1 and 2, whereby above-identified compound was obtained. MS : 490 (MH+)

Retention time: (17.8 min. for R-compound) 21.4 min. for S-compound

Analysis condition:
Column: 4.6 mm ID×150 mm; CHIRALCEL OJ-R (of the firm Daicel Chemical); two sets
Mobile phase: 0.5M NaCl04-HCl04 buffer (pH 2.0)/ acetonitrile (6/4)
Flow rate: 0.5 ml/min.
Detection wave length: 254 nm
Temperature: 40° C.

EXAMPLE 24

(±)-N'-[5-[2-[2-(6,7,8,9-tetrahydrodibenzofuran-3-yloxy) ethylamino]-1-hydroxyethyl]-2-hydroxyphenyl]-N,N-dimethylsulfamide hydrochloride The intermediates 12 and 5 were reacted and after-treated as in the synthesis of the compounds of Examples 1 and 2, whereby above-identified compound was obtained.

Rf=0.11 (methanol/chloroform=1/10) MS: 490 (MH+)

EXAMPLE 25

(R)-N-[5-[2-[2-(6,7,8,9-tetrahydrodibenzofuran-3-yloxy) ethylamino]-1-hydroxyethyl]-2-benzyloxyphenyl] methanesulfonamide The intermediates 9 and 5 were reacted and after-treated in accordance with the procedures described in Example 5, whereby the above-identified compound was obtained.

Rf=0.36 (methanol/chloroform=1/10)

EXAMPLE 26

(R)-N-[5-[2-[2-(6,7,8,9-tetrahydrodibenzofuran-3-yloxy) ethylamino]-1-hydroxyethyl]-2-hydroxyphenyl] methanesulfonamide hydrochloride Reaction and after-treatment were carried out in accordance with the procedures described in Example 6, except that the compound of Example 25 (313.6 mg) and 1 M solution (1.52 ml) of boron tribromide in methylene chloride were used, followed by purification by a silica gel chromatography (chloroform-methanol 10% of concentrated ammonia solution /chloroform=1/10), whereby the product of free sulfonamide was obtained (148 mg).

Rf=0.15 (methanol/chloroform 1/10)

To this product was added 0.1 N solution of hydrogen chloride in ethanol (in an amount of 1.1 equivalent) to convert it into a hydrochloride salt, followed by evaporating under reduced pressure. To the residue, diethyl ether was added and the thereby deposited precipitate was collected by filtration and was dried under reduced pressure 50° C., whereby the above-identified compound was obtained (140.3 mg).

Retention time: 37.8 min. for R-compound (44.9 min. for S-compound)

Analysis condition:
Column: 4.6 mm ID×150 mm; CHIRALCEL OJ-R (of the firm Daicel Chemical); two sets
Mobile Phase: 0.5M NaClO4-HClO4 buffer (pH 2.0)/acetonitrile (7/3)
Flow rate: 0.5 ml/min.
Detection wave length: 254 nm
Temperature: 40° C.

EXAMPLE 27

(R)-N-[5-[2-[2-(6,7,8,9-tetrahydrodibenzofuran-3-yloxy)ethylamino]-1-hydroxyethyl]-2-benzyloxyphenyl]methanesulfonamide The intermediates 9 and 7 were reacted and after-treated in accordance with the procedures described in Example 5, whereby the above-identified compound was obtained.

Rf=0.35 (methanol/chloroform=1/10)

EXAMPLE 28

(R)-N-[5-[2-[2-(6,7,8,9-tetrahydrodibenzothiophen-3-yloxy)ethylamino]-1-hydroxyethyl]-2-hydroxyphenyl]methanesulfonamide hydrochloride Reaction and after-treatment were carried out in accordance with the procedures described in Example 6, except that the compound of Example 27 (54 mg) and 1 M solution (0.27 ml) of boron tribromide in methylene chloride were used, followed by purification by a silica gel chromatography (chloroform-methanol containing 10% of concentrated ammonia solution/chloroform=1/10), whereby the product of free sulfonamide was obtained (19.4 mg).

Rf=0.11 (methanol/chloroform=1/10)

To this product was added 0.1 N solution of hydrogen chloride in ethanol (in an amount of 1.1 equivalent) to convert it into a hydrochloride salt, followed by evaporating under reduced pressure. To the residue was added diethyl ether, followed by concentration and drying under reduced pressure at 50° C., whereby the above-identified compound was obtained (18.7 mg).

Retention time: 48.1 min. for R-compound (54.9 min. for S-compound)

Analysis condition:
Column: 4.6 mm ID×150 mm; CHIRALCEL OJ-R (of the firm Daicel Chemical); two sets
Mobile phase: 0.5M NaClO4-HClO4 buffer (pH 2.0)/acetonitrile (7/3)
Flow rate: 0.5 ml/min.
Detection wave length: 254 nm
Temperature: 40° C.

EXAMPLE 29

(R)-N'-[5-[2-[2-(5,6,7,8,9,10-hexahydrocyclohepta[b]indol-2-yloxy)ethylamino]-1-hydroxyethyl]-2-hydroxyphenyl]-N,N-dimethylsulfamide hydrochloride A. Synthesis of
(R)-N'-[5-[2-[2-(5,6,7,8,9,10-hexahydrocyclohepta[b]indol-2-yloxy)ethylamino]-1-(triethylsilyloxy)ethyl]-2-benzyloxyphenyl]-N,N-dimethylsulfamide (intermediate 80)

A solution of the intermediate 64 (579 mg), the intermediate 13 (1. 36 g) and diisopropylethylamine (2.5 ml) in anhydrous dimethylacetamide (2.5 ml) was agitated under an argon atmosphere at 50° C. for 62 hours.

After dilution with water (200 ml). extraction with ethyl acetate(200 ml) was performed. The organic layer was washed with saturated aqueous sodium chloride solution and dried, whereupon the solvent was distilled off under reduced pressure. The residue was subjected to filtration through a silica gel pad (elution with ethyl acetate), followed by purification by a silica gel column chromatography (methanol/chloroform=2/98), whereby the above-identified compound was obtained (777.9 mg).

Rf=0.56 (methanol/chloroform=1/10)

B. Synthesis of
(R)-N'-[5-[2-[2-(5,6,7,8,9,10-hexahydrocyclohepta[b]indol-2-yloxy)ethylamino]-1-hydroxyethyl]-2-benzyloxyphenyl]-N,N-dimethylsulfamide (intermediate 81)

To a soution of the intermediate 80 (777.9 mg) in anhydrous tetrahydrofuran (39 ml), glacial acetic acid (208 μl) and 1 N solution (1.73 ml) of tetra-n-butylammonium fluoride in tetrahydrofuran were added and the mixture was agitated at room temperature for 18 hours. After dilution with saturated sodium bicarbonate solution and extraction with ethyl acetate, the organic phase was washed with saturated aqueous sodium chloride solution, followed by drying, whereupon the solvent was distilled off under reduced pressure. By purifying with a silica gel column chromatography (methanol/chloroform=2/98-5/95), the above-identified compound was obtained (451.9 mg).

Rf=0.33 (methanol/chloroform=1/10)

C. Synthesis of
(R)-N'-[5-[2-[2-(5,6,7,8,9,10-hexahydrocyclohepta[b]indol-2-yloxy)ethylamino]-1-hydroxyethyl]-2-hydroxyphenyl]-N,N-dimethylsulfamide hydrochloride The intermediate 81 (451 mg) was dissolved in anhydrous dichloromethane (33.5 ml) and cooled down to −70° C. under an argon atmosphere, whereto 1 N solution (2.03 ml) of boron tribromide in dichloromethane was added dropwise with agitation over a period of 3 minutes. After agitation for 2 hours methanol (17 ml) was added dropwise thereto carefully to terminate the reaction and the mixture was caused to elevate its temperature up to room temperature, before it was diluted with water (20 0 ml). After washing with diethyl ether (200 ml), the aqueous phase adjusted atpH 10 by 8 N aqueous sodium hydroxide solution and was extracted with ethyl acetate (300 ml). The organic layer was washed with saturated aqueous sodium chloride solution and dried, whereupon the solvent was distilled off under reduced pressure. By purifying with a silica gel column chromatography (methanol/chloroform=5/95-1/9) and converting into hydrochloride salt with 0.1 N solution of hydrogen chloride in ethanol, the above-identified compound was obtained (108.8 mg).

Rf=0.11 (methanol/chloroform=1/10)

Retention time: 18.2 min. for R-compound (21.7 min. for S-compound)

Analysis condition:
Column: 4.6 mm ID×150 mm; CHIRALCEL OJ-R (of the firm Daicel Chemical); two sets
Mobile phase: 0.5M NaClO4-HClO4 buffer (pH 2.0)/acetonitrile (6/4)
Flow rate: 0.5 ml/min.
Detection wave length: 254 nm
Temperature: 40° C.

Furthermore, compounds of other Examples as given in Table 2 were produced in the same procedures given for the intermediate of this Example

TEST EXAMPLE 1

Human β3-agonist Activity Human β3-agonist activity was examined using CHO cells (chinese hamster ovarian cells) to which pcDNA3 (in vitrogen) inserted the 1st exon of human β3 gene was transfected. Human β3 fragment was obtained by PCR using human fat tissue cDNA (supplied from Clontech) with a 63 primer [Krief et al, J. Clin. Invest., Vol. 91, p344–349 (1993)]. And then full length of human 83 gene was cloned using this fragment as a probe.

The cells were cultured in a HAM F-12 medium containing 10% of fetal bovine serum, 400 µg/ml of Geneticin (Gibco BRL), 100 U/ml penicillin and 100 µg/ml streptomycin. $5 \times 10^5$ cells were placed on a 6-well plate and cultured for 24 hours, after which the medium was changed to a HAM F-12 medium without serum and was kept for 2 hours. Each test compound was first dissolved in DMSO, and then diluted with a HAM F-12 medium containing 1 mM isobutylmethyl xanthine and 1 mM ascorbic acid. A 10-fold dilution in the range of $10^{-5}$ to $10^{-12}$ M was added into the cells.

After culturing for 30 minutes, culture medium was withdrawn, 0.5 ml of 1 N NaOH was added and was kept for 20 minutes. Ater then 0.5 ml of 1 N acetic acid was added with subsequent agitation and centrifugation. Finally, concentration of cAMP were analyzed using cAMP EIA KIT (Cayman). Intrinsic activities and $ED_{50}$ of 10 compounds in Example are shown in Table 2. BRL37344 was synthesized by the method given in "Drugs of the future", Vol.16, p797–800 (1991). CL316,243 was synthesized by the method given in J. Med. Chem., Vol. 35, p3081–3084 (1992). Isoproterenol was purchased from RBI (Research Biochimicals International).

As seen in Table 3, the activities of these compounds were found to be higher than BRL37344 and CL316,243.

TEST EXAMPLE 2

Effect on Heart

The hearts of male guinea pigs having body weights in the range of 180–250 g were excised and isolated right atrium was prepared. And then it was set in an organ bath filled with aerated Krebs solution. The beat of isolated right atrium was measured using an isometric transducer (TB-611T of the firm Nippon Koden) connected to a polygraph (MR-6000 of the firm Nippon Koden). The $ED_{50}$ values for the inventive compounds in Examples were higher than that of 83 and these compounds was selective and have almost no contribution to increase heart rate, so that it was expected to have lower side effects.

TEST EXAMPLE 3

Lipolytic Activity in Rat Adipocytes

Adipose tissues were collected from epididymis and minced. Krebs-Ringer buffer solution containing 1 mg/ml Collagenase (Sigma) and 1% of bovine serum albumin was added in an amount of 3 ml per one gram of the tissue. These cells were incubated at 37° C. for 30 minutes with shaking and then undigested tissues were removed with a nylon filter.

The resulting adipocytes were washed four times with Krebs-Ringer buffer, and then cells was diluted to $2 \times 10^5$ cells/ml with Krebs-Ringer buffer solution containing 4% of bovine serum albumin. These cells were transferred to Eppendorf tubes each in an amount of 300 µl.

Each 300 µl of a culture medium containing the test compounds was added to these tubes and was held at 37° C. for 1 hour with shaking.

Stimulation was stopped by cooling with ice. After centrifugation, the adipocytes were taken off with an aspirator, and then the concentration of glycerol was determined using F-KIT GLYCEROL (Behringer-Manheim).

A shown in Table 4, the compounds according to the present inventive exhibited in vitro lipolytic activities and, therefore, it was expected that they may be effective also in vivo lipolysis.

TEST EXAMPLE 4

Blood Glucose Lowering Effect and Lipolytic Effect

Glucose was subcutaneously administered to male ddy mice (supplied from the dirm Nippon Charles Liver) of 6 weeks age at a dose of 2 g/kg. The animals were also treated with either one of test compounds via oral or intraperitoneal administration at a dose of 0.1 ml per 10 g of body weight. After one hour, blood sample was taken from abdominal aorta, serum was separated and served as the sample.

Blood Glucose Lowering Effect:

The samples prepared as above were analyzed for the serum glucose concentration by Auto analyzer (SUPER Z of the firm M. C. Medical). For the analyzer kit, Glucose 11 HA TEST WAKO (of the firm Wako Pure Chemical) was used. % decrease in blood glucose=$[(A-B)/(A-C)] \times 100$
in whcih A represents the glucose concentration after loading glucose, B represents the glucose concentration after administration of the compound and C is the usual level of the glucose concentration.

The compound of Example 2 showed a reduction of blood glucose by an intraperitoneal administration of 10 mg/kg. Therefore, it was proven that the compounds according to the present invention are effective for therapeutic and preventive treatment of diabetes.

Lipolytic Effect:

Amount of free fatty acid in the samples was determined using NEFA HA TEST WAKO (of the firm Wako Pure Chemical). The compounds of Example 2 showed an increase of free fatty acid concentration by an intraperitoneal administration of 10 mg/kg. This shows that these compounds have lipolytic activity. Therefore, it was shown that they are useful for preventive and therapeutic treatment of hyperlipemia and obesity.

TEST EXAMPLE 5

Toxicity Test

The compounds of Example 2 was orally administered to 6 weeks age male ddy mice (supplied from the firm Nippon Chrles Liver) at a dose of 100 mg/kg. For all 8 mice, no fatal case was found, which was the case for other compounds, so that the compound according to the present invention exhibits low toxicity.

Effect of the invention

The compounds according to the present invention are novel and are useful for therapeutic and preventive treatment of β3-relating diseases, such as diabetes, obesity and hyperlipemia.

TABLE 1

| Compound No. | 1H-NMR (CDCl3): δ(ppm), J (Hz) | MS m/z |
|---|---|---|
| Intermed. 1 | 3.47 (2H, t, J=6.0), 3.61 (2H, q, J=6.0), 5.11 (1H, s), 5.29 (1H, br. s), 7.30–7.38 (5H, m) | |
| Intermed. | 1.87 (4H, m), 2.67 (4H, m), 3.61 | 365 |

TABLE 1-continued

| Compound No. | 1H-NMR (CDCl3): δ(ppm), J (Hz) | MS m/z |
|---|---|---|
| 2 | (2H, m), 4.06 (2H, t, J=5.2), 5.12 (2H, s), 5.28 (1H, br. s), 6.70 (1H, dd, J=8.5, 2.2), 6.78 (1H, d, J=2.0), 7.31 (1H, d, J=8.5), 7.3–7.39 (5 H, m), 7.56 (1H, br. s) | (MH+) |
| Intermed. 3 | (DMSO-d6): 1.78 (4H, m), 2.56 (2H, m), 2.64 (2H, m), 2.87 (2H, t, J=5.8), 3.88 (2H, t, J=5.8), 6.58 (1H, dd, J=8.5, 2.5), 6.75 (1H, d, J=2.2), 7.18 (1H, d, J = 8.5), 10.40 (1H, s) | 231 (MH+) |
| Intermed. 4 | 1.75–1.96 (4H, m), 2.58 (2H, m), 2.70 (2, m), 3.62 (2H, q, J=5.2), 4.06 (2H, q, J=5.2), 5.12 (2H, s), 5.26 (1H, br. s), 6.79 (1H, dd, J=8.5, 2.2), 6.93 (1H, d, J = 2.2), 7.25 (1H, d, J=8.5), 7.27 – 7.38 (5H, m) | 366 (MH+) |
| Intermed. 5 | 1.77–1.96 (4H, m), 2.59 (2H, m), 2.71 (2H, m), 3.10 (2H, t, J=5.2), 4.01 (2H, t, J=5.2), 6.83 (1 H, dd, J=8.5, 2.2), 6.97 (1H, d, J=2.2), 7.26 (1H, d, J=8.5) | 232 (MH+) |
| Intermed. 6 | 1.84–1.97 (4H, m), 2.66–2.74 (2H, m), 2.76–2.85 (2H, m), 3.6 2 (2H, t, J=5.2), 4.08 (2H, t, J = 4.9), 5.12 (2H, s), 5.26 (1H, br s), 6.92 (1H, dd, J=8.5, 2.2) 7.23 (1H, d, J=8.5, 2.2), 7.27–7.39 (5H, m), 7.43 (1H, d, J=8.8) | 382 (MH+) |
| Intermed. 7 | (CDCl3-CD3OD): 1.84–1.98 (4H, m), 2.67–2.75 (2H, m), 2.77–2.85 (2H, m), 3.12 (2H, t, J=4.9), 3.30 (2H, br. s), 4.07 (2H, t, J = 4.9), 6.96 (1H, dd, J=8.8, 2.5), 7.28 (1H, d, J=2.5), 7.45 (1H, d, J=8.8) | 248 (MH+) |
| Intermed. 8 | 2.70 (1H, d, J=3.3), 3.50 (1H, d d, J=10.4, 8.5), 3.63 (1H, dd, J = 10.4, 3.3), 4.92 (1H, m), 5.25 (2H, s), 7.13 (1H, d, J=8.5) 7.30–7.48 (5H, m), 7.53 (1H, d d, J = 8.8, 2.5), 7.91 (1H, d, J=2.5) | |
| Intermed. 9 | 0.53–0.62 (6H, m), 0.91 (9H, t, J=7.7), 3.81 (2H, m), 4.75 (1H, t, J=5.8), 5.24 (2H, s), 7.13 (1H, d, J=8.8), 7.31–7.52 (6H, m) 7.87 (1H, d, J=2.2) | |
| Intermed. 11 | 2.71 (1H, br. s), 2.79 (6H, s), 3.51 (1H, dd, J=10.2, 3.6), 3.59 (1H, dd, J=10.4, 3.6), 4.48 (1H, dd, J=8.5, 8.6), 5.12 (2H, s), 6.89 (1H, br. s), 6.95 (1H, d, J = 8.2), 7.09 (1H, dd, J=8.5, 1.6), 7.33–7.45 (5H, m), 7.52 (1H, d, J=1.9) | 430 (MH+) |
| Intermed. 12 | 0.52–0.63 (6H, m), 0.87–0.94 (9H, m), 2.77 (6H, s), 3.28–3.33 (2H, m), 4.71 (1H, m), 5.10 (2H, s), 6.83 (1H, br. s), 6.93 (1H, dd, J=8.5, 5.2), 7.05 (1H, dd, J = 8.5, 2.2), 7.37–7.43 (5H, m), 7.50 (1H, d, J=2.2) | |
| Intermed. 15 | 2.68 (3H, m), 7.42 (1H, dd, J=10.2, 8.4), 8.26 (1H, ddd, J=8.4, 4.2, 2.1), 8.65 (1H, dd, J=7.2, 2.1) | |
| Intermed. 16 | 2.55 (3H, s), 3.88 (2H, br. s) 7.04 (1H, ddd, J=10.5, 8.4, 0.6) 7.28–7.35 (1H, m), 7.41 (1H, ddd, J=8.7, 2.1, 0.6) | |
| Intermed. 17 | 2.61 (3H, s), 3.09 (3H,s), 6.69 (1H, br. s), 7.25 (1H, dd, J=9.9, 9.6), 7.82 (1H, ddd, J=8.4, 4.8, 2.1), 8.17 (1H, dd, J=7.5, 2.1) | |
| Intermed. | 3.16 (3H, s), 4.41 (2H, s), 6.62 | |
| 18 | (1H, br. s), 7.28 (1H, t, J=9.0), 7.86 (1H, ddd, J=8.7, 4.8, 2.1), 8.21 (1H, dd, J=7.5, 2.1) | |
| Intermed. 19 | 0.52–0.62 (6H, m), 0.87–0.94 (9H, m), 3.03 (3H, s), 3.3–3.34 (2H, m), 4.74 (1H, m), 6.54 (1H, br. s), 7.08–7.2 (2H, m), 7.57 (1H, dd, J=7.6, 2.2) | |
| Intermed. 24 | 2.65 (3H, s), 7.68 (1H, d, J=8.4), 8.09 (1H, dd, J=8.7, 2.1) 8.43 (1H, d, J=2.1) | |
| Intermed. 25 | 2.55 (3H, s), 4.19 (2H, br. s) 7.23–7.37 (3H, m) | |
| Intermed. 26 | 2.61 (3H, s), 3.07 (3H, s), 6.86 (1H, br. s), 7.54 (1H, d, J=8.4) 7.75 (1H, dd, J=8.4, 2.1), 8.24 (1H, d, J=2.1) | |
| Intermed. 27 | 3.10 (3H, s), 4.41 (2H, s), 6.90 (1H, br. s), 7.58 (1H, d, J=8.4) 7.78 (1H, dd, J=8.4, 2.1), 8.24 (1H, d, J=2.1) | |
| Intermed. 29 | 0.54–0.63 (6H, m), 0.87–0.95 (9H, m), 3.02 (3H, s), 3.28–3.34 (2H, m), 4.74 (1H, m), 6.81 (1H, br. s), 7.16 (1H, dd, J=8.2, 2.2), 7.40 (1H, d, J=8.2), 7.65 (1H, d, J=2.2) | |
| Intermed. 32 | 2.61 (3H, s), 3.06 (3H, s), 7.66 (1H, dd, J=8.5, 2.2), 7.71 (1H, d, J=8.5), 8.20 (1H, d, J=2.2) | |
| Intermed. 33 | 3.09 (3H, s), 4.42 (2H, s), 7.68 (1H, dd, J=8.4, 1.8), 7.75 (1H, d, J=8.4), 8.21 (1H, d, J=1.8) | |
| Intermed. 34 | 2.74 (1H, d, J=3.6), 3.03 (3H, s), 3.48–3.56 (1H, m), 3.65 (1H, dd, J=10.7, 3.6), 4.92 (1H, ddd, J=8.0, 4.4, 3.6), 6.82 (1H, br. s), 7.15 (1H, dd, J=8.2, 1.9), 7.61 (1H, d, J=8.2), 7.67 (1H, d, J=1.9) | |
| Intermed. 35 | 0.52–0.68 (6H, m), 0.86–0.96 (9H, m), 3.01 (3H, s), 3.32 (2H, d, J=5.8), 4.73 (1H, t, J=5.8), 6.82 (1H, br. s), 7.10 (1H, dd, J = 8.2, 2.2), 7.56 (1H, d, J=8.2) 7.65 (1H, d, J=2.2) | |
| Intermed. 36 | 2.61 (3H, s), 5.45 (2H, s), 7.22 (1H, d, J=8.8), 7.34–7.55 (5H, m), 8.26 (1H, dd, J=8.8, 2.2), 8.55 (1H, d, J=2.5) | |
| Intermed. 37 | 2.57 (3H, d, J=5.2), 2.61 (3H, s), 4.70 (1H, q, J=5.5), 5.32 (2H, s), 7.17 (1H, d, J=8.8), 7.24–7.51 (5H, m), 8.18 (1H, dd, J = 8.8, 2.2), 8.50 (1H, d, J=2.2) | |
| Intermed. 38 | 2.58 (3H, s), 4.43 (2H, s), 4.74 (1H, s), 5.34 (2H, s), 7.20 (1H, d, J=8.8), 7.36–7.51 (5H, m) 8.20 (1H, dd, J=8.8, 2.2), 8.52 (1H, d, J=2.2) | |
| Intermed. 39 | 2.49 (3H, d, J=5.2), 3.28 (1H, d, J=3.0), 3.47 (1H, dd, J=10.7 8.0), 3.56 (1H, dd, J=10.7, 4.1), 4.83 (1H, q, J=5.5), 4.88 (1H, m), 5.22 (2H, s), 7.09 (1H, d, J=8.8), 7.30–7.48 (5H, m), 7.55 (1H, dd, J=8.8, 2.5), 7.88 (1H, d, J=2.2) | |
| Intermed. 40 | 0.47–0.66 (6H, m), 0.85–0.95 (9H, m), 2.52 (3H, d, J=5.5), 3.28–3.35 (2H, m), 4.66 (1H, m) 4.77 (1H, m), 5.23 (2H, s), 7.09 (1H, d, J=8.5), 7.34–7.52 (5H, m), 7.55 (1H, dd, J=8.5, 2.5) 7.91 (1H, d, J=2.2) | |
| Intermed. | 2.69 (3H, d, J=5.4), 4.45 (2H, | |

TABLE 1-continued

| Compound No. | 1H-NMR (CDCl3): δ(ppm), J (Hz) | MS m/z |
|---|---|---|
| 41 | s), 4.95 (1H, br. s), 7.69 (1H, d, J=8.2), 8.15 (1H, dd, J=8.2, 2.2), 8.65 (1H, d, J=2.2) | |
| Intermed. 42 | 2.65 (3H, d, J=5.5), 3.52 (1H, dd, J=10.6, 8.2), 3.67 (1H, dd, J=10.6, 3.6), 4.93 (1H, br. s) 5.00 (1H, dd, J=8.2, 3.6), 7.56 (1H, d, J=8.2), 7.61 (1H, dd, J = 8.2, 1.9), 8.11 (1H, d, J=1.9) | |
| Intermed. 43 | 0.56–0.63 (6H, m), 0.86–0.94 (9H, m), 2.63 (3H, d, J=5.2), 3.30–3.35 (2H, m), 4.80 (1H, d, J = 5.8), 4.86–4.94 (1H, m), 7.52–7.55 (2H, m), 8.08 (1H, d, J=1.9) | |
| Intermed. 44 | 0.47–0.68 (6H, m), 0.91 (9H, t, J=7.7), 3.01 (3H, s), 3.33 (2H, d, J=5.8), 4.75 (1H, t, J=5.8), 6.49 (1H, br. s), 7.13–7.19 (2H, m), 7.22 (1H, m), 7.33 (1H, t, J = 7.7) | |
| Intermed. 45 | 2.86 (1H, d, J=3.6), 3.56 (1H, dd, J=10.7, 8.5), 3.70 (1H, dd, J=10.7, 3.6), 5.06 (1H, dt, J = 8.5, 3.6), 7.58 (1H, t, J=7.7), 7.75 (1H, ddd, J=7.7, 1.1, 0.5) 8.20 (1H, m), 8.30 (1H, dd, J = 2.2, 1.6) | |
| Intermed. 46 | 2.72 (½H, s), 2.73 (½H, s), 4.46 (2H, s), 7.70 (1H, dd, J=7.8, 7.8), 8.11 (1H, ddd, J=7.8, 1.8), 8.21 (1H, ddd, J=7.8, 1.8), 8.45 (1H, dd, J=1.8, 1.8) | |
| Intermed. 47 | 2.79 (3H, s), 9.08 (2H, d, J=2.2), 9.25 (1H, dd, J=2.2) | |
| Intermed. 48 | 2.63 (3H, s), 4.19 (2H, br. s), 7.53 (1H, dd, J=2.2), 7.67 (1H, dd, J=2.2), 8.10 (1H, dd, J=2.2) | |
| Intermed. 49 | 2.68 (3H, s), 6.34 (1H, br. s), 7.79 (1H, dd, J=2.5), 7.92 (1H, dd, J=2.2), 8.34 (1H, dd, J=1.9) | |
| Intermed. 50 | 2.66 (3H, s), 5.20 (2H, s), 7.30–7.48 (5H, m), 7.88 (1H, dd, J = 2.5), 8.01 (1H, dd, J=2.5, 1.9), 8.36 (1H, dd, J=1.9) | |
| Intermed. 51 | 2.53 (3H, s), 3.80 (2H, br. s), 5.07 (2H, s), 6.50 (1H, dd, J=1.9), 6.89 (1H, dd, J=1.9), 6.98 (1H, dd, J=2.2), 7.30–7.48 (5H, m) | |
| Intermed. 52 | 2.58 (3H, s), 3.00 (3H, s), 5.12 (2H, s), 6.88 (1H, br. s), 7.15 (1H, d, J=2.2), 7.27–7.47 (7H, m) | |
| Intermed. 53 | 3.02 (3H, s), 4.40 (2H, s), 5.13 (2H, s), 6.95 (1H, br. s), 7.15–7.18 (1H, m), 7.31–7.50 (7H, m) | |
| Intermed. 54 | 1.39 (3H, t, J=7.1), 1.66 (3H, s), 3.76 (2H, m), 4.05 (2H, m) 4.38 (2H, q, J=7.1), 7.56 (2H, d, J=8.5), 8.03 (2H, d, J=8.5) | |
| Intermed. 55 | 2.61 (3H, s), 4.79 (2H, s), 7.46 (2H, d, J=8.0), 7.96 (2H, d, J = 8.2) | |
| Intermed. 56 | 2.14 (3H, s), 2.61 (3H, s), 5.17 (2H, s), 7.45 (2H, d, J=8.5), 7.96 (2H, d, J=8.5) | |
| Intermed. 57 | 2.20 (3H, s), 2.68 (3H, s), 5.57 (2H, s), 7.73 (1H, d, J=8.2), 8.22 (1H, dd, J=8.2, 1.6), 8.65 (1H, d, J=1.6) | |
| Intermed. 58 | 2.10 (3H, s), 2.56 (3H, s), 4.18 (2H, br. s), 5.12 (2H, s), 7.27–7.31 (3H, m) | |
| Intermed. 59 | 2.11 (3H, s), 2.62 (3H, s), 3.12 (3H, s), 5.18 (2H, s), 7.52 (1H, d, J=8.0), 7.74 (1H, br. s), 7.79 (1H, dd, J=8.0, 1.6), 8.08 (1H, d, J=1.6) | |
| Intermed. 60 | 2.12 (3H, s), 3.14 (3H, s), 4.43 (2H, s), 5.18 (2H, s), 7.55 (1H, d, J=8.0), 7.80 (1H, br. s), 7.83 (1H, dd, J=8.0, 1.7), 8.12 (1H, d, J=1.7) | |
| Intermed. 61 | 1.71–1.82 (4H, m), 1.82–1.93 (2H, m), 2.71–2.86 (4H, m), 3.83 (3H, s), 6.75 (1H, dd, J=8.5, 2.5), 6.78 (1H, d, J=1.9), 7.33 (1H, d, J=8.5), 7.54 (1H, br. s) | |
| Intermed. 62 | 1.70–1.81 (4H, m), 1.81–1.93 (2H, m), 2.70–2.86 (4H, m), 4.56 (1H, br. s), 6.63 (1H, dd, J=8.5, 2.2), 6.73 (1H, d, J=2.2), 7.28 (1H, d, J=8.5), 7.41 (1H, br. s) | |
| Intermed. 63 | 1.71–1.82 (4H, m), 1.82–1.93 (2H, m), 2.72–2.83 (4H, m), 3.60 (2H, q, J=5.2), 4.05 (2H, t, J = 5.2), 5.11 (2H, s), 5.28 (1H, br. s), 6.71 (1H, dd, J=8.5, 2.2), 6.75 (1H, d, J=2.2), 7.32 (1H, d, J=8.5), 7.3–7.39 (5H, m), 7.58 (1H, br. s) | |
| Intermed. 64 | 1.60–1.81 (4H, m), 1.81–1.92 (2H, m), 2.69–2.80 (4H, m), 3.05 (2H, t, J=5.2), 3.97 (2H, t, J=5.2), 6.71–6.79 (2H, m), 7.32 (1H, d, J=9.1), 7.85 (1H, br. s) | |
| Intermed. 65 | 1.58–1.73 (2H, m), 2.00 (3H, s), 2.20–2.32 (2H, m), 2.35–2.55 (4H, m), 4.25 (1H, m), 5.48 (1H, br. s) | |
| Intermed. 66 | (DMSO-d6): 1.75 (1H, m), 1.82 (3H, s), 1.94 (1H, m), 2.42 (1H, dd, J=14.6, 8.5), 3.73 (3H, s), 4.01 (1H, m), 6.57 (1H, dd, J=8.2, 2.2), 6.75 (1H, d, J=2.2), 7.18 (1H, d, J=8.5), 7.93 (1H, d, J=8.0), 10.50 (1H, s) | |
| Intermed. 67 | (DMSO-d6): 1.68–1.76 (1H, m), 1.82 (3H, s), 1.90–1.99 (1H, m), 2.35–2.44 (1H, m), 2.67–2.75 (2H, m), 2.77–2.86 (1H, m), 3.92–4.05 (1H, m), 6.44 (1H, dd, J = 8.8, 1.9), 6.61 (1H, d, J=1.9), 7.06 (1H, d, J=8.8), 7.91 (1H, d, J=7.1), 8.70 (1H, s), 10.27 (1H, s) | |
| Intermed. 68 | 1.97 (3H, s), 1.97–2.10 (2H, m), 2.57 (1H, dd, J=15.7, 6.0), 2.68–2.88 (4H, m), 3.04 (1H, dd, J=15.7, 5.2), 3.61 (2H, q, J=5.2), 4.05 (2H, t, J=5.2), 4.38–4.48 (1H, m), 5.12 (2H, s), 5.23–5.32 (1H, m), 5.63 (1H, d, J=8.2) 6.72 (1H, dd, J=8.5, 2.2), 6.79 (1H, d, J=2.2), 7.28 (1H, d, J=8.5), 7.30–7.40 (5H, m), 7.75 (1H, br. s) | |
| Intermed. 69 | 0.47–0.61 (6H, m), 0.82–0.92 (9H, m), 1.74–1.95 (4H, m), 2.61–2.77 (5H, m), 2.75 (6H, s), 2.86 (1H, dd, J=11.5, 8.0), 2.99 (2H, t, J=5.2), 4.07 (2H, t, J=5.2), 4.79 (1H, dd, J=8.0, 4.4), 5.08 (2H, s), 6.71 (1H, dd, J=8.5, 2.2), 6.80 (1H, d, J=2.2), 6.90 (1H, d, J=8.5), 7.05 (1H, dd, J = 8.2, 1.9), 7.30 (1H, d, J=7.7), 7.35–7.45 (5H, m), 7.53 (1H, d, J=1.9), 7.69 (1H, s) | |
| Example 1 | 1.78–1.93 (4H, m), 2.62–2.70 (4H, m), 2.72–2.78 (1H, m), 2.75 (6H, s), 2.93 (1H, dd, J=12.1, 3.6), | 579 (MH+) |

TABLE 1-continued

| Compound No. | 1H-NMR (CDCl3): δ(ppm), J (Hz) | MS m/z |
|---|---|---|
| | 2.99–3.05 (2H, m), 4.07 (2H, t, J=5.2), 4.68 (1H, dd, J=9.1, 3.6), 5.07 (2H, s), 6.71 (1H, dd, J=8.5, 2.2), 6.81 (1H, d, J=2.2), 6.89 (1H, d, J=8.2), 7.08 (1H, dd, J=8.5, 1.9), 7.30 (1H, d, J=8.5), 7.35–7.44 (5H, m), 7.51 (1H, d, J=2.2), 7.77 (1H, s) | |
| Example 2 | 1.70–1.85 (4H, m), 2.52–2.59 (2H, m), 2.60–2.69 (4H, m), 2.65 (6H, s), 2.87–2.94 (2H, m), 3.94–4.02 (2H, m), 4.49–4.56 (1H, m), 5.24 (1H, br. s), 6.56 (1H, dd, J=8.5, 2.2), 6.75 (1H, d, J=2.2), 6.78 (1H, d, J=8.2), 6.96 (1H, dd, J=8.2, 1.9), 7.17 (1H, d, J=8.5), 7.28 (1H, d, J=1.9), 10.40 (1H, s) | 489 (MH+) |
| Intermed. 70 | 0.50–0.60 (6H, m), 0.89 (9H, t, J=7.8), 1.80–1.92 (4H, m), 2.63–2.71 (4H, m), 2.75 (1H, dd, J = 11.8, 4.4), 2.86 (1H, dd, J=11.8, 4.4), 2.86 (1H, dd, J=11.8, 7.7), 2.97–3.02 (2H, m), 4.07 (2H, t, J=5.2), 4.83 (1H, dd, J=7.7, 4.4), 5.21 (2H, s), 6.71 (1H, dd, J=8.5, 2.2), 6.76 (1H, d, J=2.2), 7.06 (1H, d, J=8.8), 7.31 (1H, d, J=8.5), 7.32–7.46 (5H, m), 7.49 (1H, dd, J=8.8, 2.2), 7.61 (1H, br. s), 7.88 (1H, d, J=2.2) | |
| Intermed. 71 | 0.38–0.55 (6H, m), 0.77–0.9 (9H, m), 1.78–1.92 (4H, m), 2.60–2.70 (4H, m), 3.37–3.77 (4H, m), 3.85–4.12 (2H, m), 4.83 (½H, t, J=6.3), 5.06–5.12 (½H, m), 5.09 (⅔H, s), 5.15 (½H, s), 5.16 (2H, s), 6.59–6.64 (1H, m), 6.67 (½H, dd, J=8.5, 2.2), 6.72 (½H, d, J=2.2), 6.97 (½H, d, J=8.8), 7.03 (½H, d, J=8.8), 7.24–7.58 (12H, m), 7.73 (½H, d, J=1.7), 7.90 (½H, d, J=2.2) | |
| Intermed. 72 | 0.39–0.55 (6H, m), 0.78–0.89 (9H, m), 1.80–1.93 (4H, m), 2.60–2.70 (4H, m), 3.35–4.10 (8H, m), 4.71 (½H, m), 4.94 (½H, m), 5.03 (⅔H, s), 5.04 (⅔H, s), 5.13 (½H, s), 5.18 (½H, s), 6.51–6.82 (5H, m), 7.23–7.49 (11H + ½H, m), 7.58 (½H, br. s) | |
| Intermed. 73 | 0.37–0.56 (6H, m), 0.75–0.89 (9H, m), 1.79–1.94 (4H, m), 2.60–2.71 (4H, m), 2.83 (⅔H, s), 2.84 (⅔H, s), 3.40–3.65 (4H, m), 3.89–4.12 (2H, m), 4.79 (½H, m), 5.02 (½H, m), 5.05 (⅔H, s), 5.06 (⅔H, s), 5.11 (½H, s), 5.16 (½H, s), 6.61 (½H, dd, J=8.5, 2.2), 6.66 (½H, dd, J=8.5, 2.2), 6.70 (½H, d J=1.9), 6.77 (1H, m), 6.78 (½H, d, J=1.9), 6.89 (½H, d, J = 8.5), 6.93 (½H, d, J=8.5), 6.97 (½H, dd, J=8.2, 1.9), 7.11 (½H, dd, J=8.2, 1.9), 7.23–7.45 (11H, m), 7.51 (½H, d, J = 1.9), 7.54 (½H, br. s), 7.60 (½H, d, J=1.7), 7.65 (½H, br. s) | |
| Example 5 | 1.80–1.95 (4H, m), 2.62–2.70 (4H, m), 2.74 (1H, dd, J=12.4, 9.1), 2.89 (3H, s), 2.96 (1H, dd, J=12.4, 3.6), 3.00–3.07 (2H, m), 4.08 (2H, t, J=4.9), 4.68 (1H, dd, J=9.1, 3.6), 5.08 (2H, s), 6.72 (1H, dd, J=8.5, 1.9), 6.81 (1H, d, J=1.7), 6.96 (1H, d, J = 8.2), 7.17 (1H, dd, J=8.5, 1.9), 7.31 (1H, d, J=8.5), 7.34–7.44 (4H, m), 7.53 (1H, d, J=1.9), 7.73 (1H, br. s) | 550 (MH+) |
| Example 6 | (DMSO-d6): (HCl) 1.70–1.90 (4H, m), 2.54–2.61 (2H, m), 2.61–2.70 (2H, m), 2.95 (3H, s), 3.00–3.14 (1H, m), 3.15–3.27 (1H, m), 3.37–3.50 (2H, m), 4.20–4.30 (2H, m), 4.85–4.92 (1H, m), 6.10 (1H, br. s), 6.64 (1H, dd, J = 8.5, 2.5), 6.83 (1H, d, J=2.2), 6.92 (1H, d, J=8.0), 7.07 (1H, dd, J=8.5, 2.2), 7.23 (1H, d, J = 8.5), 7.26 (1H, d, J=1.9), 8.80 (1H, s), 8.82 (1H, br. s), 8.92 (1H, br. s), 10.00 (1H, s), 10.51 (1H, s) | 460 (MH+) |
| Intermed. 74 | 0.55–0.60 (6H, m), 0.88 (9H, t, J=8.0), 1.8–1.92 (4H, m), 2.63–2.72 (4H, m), 2.75 (1H, dd, J = 11.8, 4.4), 2.86 (1H, dd, J=11.8, 7.8), 2.97 (3H, s), 3.00 (2H, t, J=5.1), 4.07 (2H, t, J=5.1), 4.83 (1H, dd, J=7.8, 4.4), 6.70 (1H, dd, J=8.5, 2.2), 6.80 (1H, d, J=2.2), 7.08 (1H, dd, J=9.9, 8.5), 7.14–7.20 (1H, m), 7.30 (1H, d, J=8.5), 7.57 (1H, dd, J = 7.8, 2.2), 7.67 (1H, br. s) | |
| Example 9 | 1.82–1.94 (4H, m), 2.63–2.75 (5H, m), 2.96–3.08 (5H, m), 3.01 (3H, s), 4.10 (2H, t, J=5.2), 4.69 (1H, dd, J=9.0, 3.6), 6.72 (1H, dd, J=8.5, 2.2), 6.82 (1H, d, J=2.2), 7.11 (1H, dd, J=9.9, 8.5), 7.19–7.25 (1H, m), 7.32 (1H, d, J=8.5), 7.56 (1H, dd, J = 7.7, 1.9), 7.65 (1H, br. s) | 462 (MH+) |
| Intermed. 75 | 0.51–0.61 (6H, m), 0.89 (9H, t, J=7.8), 1.8–1.93 (4H, m), 2.63–2.72 (4H, m), 2.77 (1H, dd, J=11.8, 4.4), 2.86 (1H, dd, J=11.8, 7.7), 2.95 (3H, s), 3.00 (2H, t, J=5.2), 4.08 (2H, t, J=5.2), 4.83 (1H, dd, J=7.7, 4.4), 6.70 (1H, dd, J=8.5, 2.2), 6.81 (1H, d, J=2.2), 7.16 (1H, dd, J=8.2, 1.9), 7.30 (1H, d, J=8.2), 7.37 (1H, d, J=8.5), 7.63 (1H, br. s), 7.67 (1H, d, J=1.9) | |
| Example 12 | (DMSO-d6) (HCl): 1.72–1.85 (4H, m), 2.53–2.60 (2H, m), 2.62–2.68 (2H, m), 2.97–3.06 (1H, m), 3.05 (3H, s), 3.16–3.24 (1H, m), 3.29–3.36 (2H, m), 4.36–4.45 (2H, m), 4.90–4.99 (1H, m), 6.16–6.24 (1H, m), 6.64 (1H, dd, J = 8.5, 1.9), 6.82 (1H, d, J=1.9), 7.22 (1H, d, J=8.5), 7.28 (1H, dd, J=8.2, 1.9), 7.54 (1H, d, J = 1.9), 7.54 (1H, d, J=8.2), 8.5–9.0 (2H, br. s), 10.49 (1H, s) | 478 (MH+) |
| Intermed. 76 | 0.50–0.60 (6H, m), 0.89 (9H, t, J=7.8), 1.8–1.95 (4H, m), 2.63–2.93 (4H, m), 2.77 (1H, dd, J=11.8, 4.4), 2.86 (1H, dd, J=11.8, 7.7), 2.95 (3H, s), 2.99 (2H, t, J=5.2), 4.07 (2H, t, J=5.2), 4.83 (1H, dd, J=7.7, 4.4), 6.70 (1H, dd, J=8.5, 2.2), 6.80 (1H, | |

TABLE 1-continued

| Compound No. | 1H-NMR (CDCl3): δ(ppm), J (Hz) | MS m/z |
|---|---|---|
| | d, J=2.2), 7.09 (1H, dd, J=8.2, 1.9), 7.30 (1H, d, J=8.5), 7.53 (1H, d, J=8.2), 7.64–7.70 (2H, m) | |
| Example 15 | 1.82–1.94 (4H, m), 2.63–2.75 (5H, m), 2.96–3.08 (5H, m), 3.01 (3H, s), 4.10 (2H, t, J=5.2), 4.69 (1H, dd, J=9.0, 3.6), 6.72 (1H, dd, J=8.5, 2.2), 6.82 (1H, d, J=2.2), 7.11 (1H, dd, J=9.9, 8.5), 7.19–7.25 (1H, m), 7.32 (1H, d, J=8.5), 7.56 (1H, dd, J = 7.7, 1.9), 7.65 (1H, br. s) | 524 (M + 2)+ |
| Intermed. 77 | 0.48–0.58 (6H, m), 0.83–0.91 (9H, m), 1.78–1.93 (4H, m), 2.62–2.71 (4H, m), 2.78 (1H, dd, J = 11.8, 4.4), 2.88 (1H, dd, J=11.8, 7.4), 2.91 (3H, s), 2.96–3.02 (2H, m), 4.06 (2H, t, J=5.1), 4.82 (1H, dd, J=7.4, 4.4), 6.69 (1H, dd, J=8.5, 2.2), 6.75 (1H, d, J=2.2), 7.12–7.20 (3H, m), 7.27 (1H, m), 7.30 (1H, d, J=8.5), 7.84 (1H, s) | |
| Example 17 | 1.80–1.95 (4H, m), 2.64–2.76 (5H, m), 2.98 (1H, m), 2.98–3.08 (3H, m), 4.10 (2H, t, J=5.2), 4.72 (1H, dd, J=8.9, 3.4), 6.72 (1H, dd, J=8.5, 2.2), 6.80 (1H, d, J=1.9), 7.14–7.22 (3H, m), 7.30–7.32 (2H, m), 7.67 (1H, br. s) | 444 (MH+) |
| Intermed. 78 | 0.50–0.60 (6H, m), 0.89 (9H, t, J=7.7), 1.82–1.94 (4H, m), 2.60 (3H, d, J=5.2), 2.63–2.73 (4H, m), 2.82 (1H, dd, J=11.8, 4.4), 2.87 (1H, dd, J=11.8, 7.6), 2.99 (2H, t, J=5.2), 4.07 (2H, t, J=5.2), 4.85–4.92 (2H, m), 6.71 (1H, dd, J=8.5, 2.2), 6.78 (1H, d, J=2.2), 7.31 (1H, d, J=8.5), 7.48 (1H, d, J=8.2), 7.53 (1H, dd, J=8.2, 1.9), 7.67 (1H, br. s), 8.11 (1H, d, J=1.9) | |
| Example 20 | 1.80–1.94 (4H, m), 2.62 (3H, s), 2.63–2.73 (5H, m), 2.96–3.08 (3H, m), 4.10 (2H, t, J=5.5), 4.75 (1H, dd, J=9.1, 3.3), 4.95 (1H, br), 6.72 (1H, dd, J=8.5, 2.2), 6.80 (1H, d, J=2.2), 7.32 (1H, d, J=8.5), 7.48 (1H, d, J=8.2), 7.57 (1H, d, J=8.2), 7.71 (1H, br. s), 8.09 (1H, d, J=1.9) | 478 (MH+) |
| Intermed. 79 | 0.50–0.61 (6H, m), 0.88 (9H, t, J=7.7), 1.77–1.96 (4H, m), 2.52–2.63 (2H, m), 2.65–2.78 (3H, m), 2.76 (6H, s), 2.86 (1H, dd, J=11.8, 8.2), 3.01 (2H, t, J=5.2), 4.08 (2H, t, J=5.2), 4.79 (1H, dd, J=8.2, 3.9), 5.09 (2H, s), 6.80 (1H, dd, J=8.5, 2.2), 6.90 (1H, d, J=8.5), 6.94 (1H, d, J = 2.2), 7.04 (1H, dd, J=8.2, 1.9), 7.25 (1H, d, J=8.2), 7.34–7.46 (5H, m), 7.51 (1H, d, J=1.9) | |
| Example 21 | 1.77–1.96 (4H, m), 2.55–2.62 (2H, m), 2.67–2.74 (3H, m), 2.77 (6H, s), 2.96 (1H, dd, J=12.1, 3.6), 3.06 (2H, q, J=4.9), 4.09 (2H, t, J=4.9), 4.66 (1H, dd, J = 9.3, 3.6), 5.10 (2H, s), 6.81 (1H, dd, J=8.5, 2.2), 6.93 (1H, d, J=8.5), 6.95 (1H, d, J=2.2), 7.10 (1H, dd, J=8.2, 1.9), 7.26 (1H, d, J=8.2), 7.35–7.45 (5H, m), 7.51 (1H, d, J=1.9) | 580 (MH+) |
| Example 22 | (DMSO-d6): (HCl) 1.70–1.92 (4H, m), 2.52–2.59 (2H, m), 2.66– | 490 (MH+) |
| | 2.72 (2H, m), 2.67 (6H, s), 2.98–3.08 (1H, m), 3.14–3.22 (1H, m), 3.38–3.47 (2H, m), 4.26–4.35 (2H, m), 4.83–4.92 (1H, m), 6.09 (1H, d, J=3.3), 6.87 (1H, d, J=8.2), 6.89 (1H, dd, J=8.2, 2.2), 7.02 (1H, dd, J=8.2, 1.9), 7.17 (1H, d, J=2.2), 7.34 (1H, d, J=2.2), 7.37 (1H, d, J=8.5), 8.70 (1H, s), 8.89 (1H, br. s), 10.00 (1H, s) | |
| Example 25 | 1.78–1.96 (4H, m), 2.56–2.62 (2H, m), 2.67–2.77 (3H, m), 2.90 (3H, s), 2.99 (1H, dd, J=12.0, 3.6), 3.07 (2H, q, J=4.9), 4.09 (2H, t, J=4.9), 4.67 (1H, dd, J = 9.3, 3.6), 5.10 (2H, s), 6.82 (1H, dd, J=8.2, 2.2), 6.96 (1H, d, J=2.2), 6.98 (1H, d, J=8.5), 7.18 (1H, dd, J=8.5, 2.2), 7.26 (1H, d, J=8.5), 7.34–7.45 (5H, m), 7.53 (1H, d, J=2.2) | 551 (MH+) |
| Example 26 | (DMSO-d6): 1.73–1.89 (4H, m), 2.50–2.57 (2H, m), 2.63–2.70 (4H, m), 2.92 (3H, s), 2.90–2.96 (2H, m), 3.99–4.07 (2H, m), 4.50–4.58 (1H, m), 5.25 (1H, br. s), 6.82 (1H, dd, J=8.5, 2.2), 6.83 (1H, d, J=8.2), 7.01 (1H, dd, J=8.2, 2.1), 7.09 (1H, d, J=2.2), 7.19 (1H, d, J=1.9), 7.31 (1H, d, J=8.2) | 461 (MH+) |
| Example 27 | 1.86–1.94 (4H, m), 2.68–2.78 (3H, m), 2.78–2.84 (2H, m), 2.90 (3H, s), 2.99 (1H, dd, J=12.1, 3.6), 3.07 (2H, q, J=4.9), 4.12 (2H, t, J=4.9), 4.67 (1H, dd, J = 9.3, 3.8), 5, 10 (2H, s), 6.95 (1H, dd, J=8.8, 2.5), 6.98 (1H, d, J=8.8), 7.16–7.21 (1H, m), 7.26 (1H, m), 7.35–7.42 (5H, m), 7.44 (1H, d, J=8.8), 7.53 (1H, d, J=2.2) | 567 (MH+) |
| Example 28 | (DMSO-d6):(HCl) 1.78–1.90 (4H, m), 2.64–2.71 (2H, m), 2.74–2.80 (2H, m), 2.95 (3H, m), 3.02–3.12 (1H, m), 3.16–3.26 (1H, m), 3.39–3.47 (2H, m), 4.29–4.37 (2H, m), 4.82–4.92 (1H, m), 6.10 (1H, d, J=3.8), 6.91 (1H, d, J=8.2), 7.03 (1H, dd, J=8.8, 2.5) 7.07 (1H, dd, J=8.2, 1.9), 7.26 (1H, d, J=1.9), 7.52 (1H, d, J=2.5), 7.54 (1H, d, J=5.8), 8.79 (1H, s), 8, 84(1H, br. s) 8.95 (1H, br. s), 10.01 (1H, s) | 477 (MH+) |
| Intermed. 80 | 0.49–0.62 (6H, m), 0.89 (9H, t, J=7.8), 1.7–1.81 (4H, m), 1.82–1.92 (2H, m), 2.72–2.8 (5H, m) 2.76 (6H, s), 2.81–2.87 (1H, m) 2.99 (2H, br.t, J=5.2), 4.07 (2H, t, J=5.2), 4.79 (1H, dd, J = 8.2, 4.1), 5.09 (2H, s), 6.72 (1H, dd, J=8.5, 2.2) 6.78 (1H, d, J=2.2), 6.90 (1H, d, J=8.5), 7.04 (1H, dd, J=8.5, 2.2), 7.31 (1H, d, J=8.8), 7.36–7.42 (5H, m), 7.53 (1H, d, J=2.2), 7.66 (1H, br. s) | |
| Intermed. 81 | 1.71–1.81 (4H, m), 1.81–1.92 (2H, m), 2.7–2.82 (5H, m), 2.77 (6H, s), 2.97 (1H, dd, J=12.0, 3.8), 3.01–3.06 (2H, m), 4.09 (2H, br.t, J=5.2), 4.63–4.68 (1H, m), 5.11 (2H, s), 6.73 (1H, dd, J = 8.5, 2.2), 6.80 (1H, d, J=2.2), | |

TABLE 1-continued

| Compound No. | 1H-NMR (CDCl3): δ(ppm), J (Hz) | MS m/z |
|---|---|---|
| Example 29 | 6.93 (1H, d, J=8.8), 7.10 (1H, dd, J=8.5, 1.9), 7.32 (1H, d, J = 8.5), 7.36–7.42 (5H, m), 7.52 (1H, d, J=1.9), 7.64 (1H, br. s) (DMSO-d6): 1.60–1.72 (4H, m), 1.78–1.86 (2H, m), 2.63–2.70 (2H, m), 2.65 (6H, s), 2.71–2.79 (2H, m), 2.90 (2H, t, J=5.5), 3.97 (2H, t, J=5.5), 4.52 (1H, m), 5.23 (1H, br. s), 6.56 (1H, dd, J = 8.5, 2.2), 6.72 (1H, d, J=2.2), 6.78 (1H, d, J=8.0), 6.96 (1H, dd, J=8.5, 2.2), 7.21 (1H, d, J = 8.5), 7.28 (1H, d, J=1.9), 10.42 (1H, s) | 503 (MH+) |

TABLE 2

| Example | R1 | R2 | *1 | R6 | *2 | X | n | R7 | R8 |
|---|---|---|---|---|---|---|---|---|---|
| 30 | 4-OH | SO$_2$NHMe | RS, R, S | H | — | NH | 1 | H | H |
| 31 | 4-OH | SO$_2$NMe$_2$ | RS, R, S | H | — | NH | 1 | H | H |
| 32 | 4-CH | SO$_2$NMeCH$_2$Ph | RS, R, S | H | — | NH | 1 | H | H |
| 33 | 4-OH | NHSO$_2$CHMe$_2$ | RS, R, S | H | — | NH | 1 | H | H |
| 34 | 4-OH | NHSO$_2$NEt$_2$ | RS, R, S | H | — | NH | 1 | H | H |
| 35 | 4-OH | NHSO$_2$NMeCH$_2$Ph | RS, R, S | H | — | NH | 1 | H | H |
| 36 | 5-OH | NHSO$_2$Me | RS, R, S | H | — | NH | 1 | H | H |
| 37 | 4-CH | NO$_2$ | RS, R, S | H | — | NH | 1 | H | H |
| 38 | 4-OH | NH$_2$ | RS, R, S | H | — | NH | 1 | H | H |
| 39 | 4-CH | CH$_2$OH | RS, R, S | H | — | NH | 1 | H | H |
| 40 | 4-OH | NHCONH$_2$ | RS, R, S | H | — | NH | 1 | H | H |
| 41 | 4-OH | NHCHO | RS, R, S | H | — | NH | 1 | H | H |
| 42 | -CH$_2$CH | NHSO$_2$Me | RS, R, S | H | — | NH | 1 | H | H |
| 43 | 4-NH$_2$ | NHSO$_2$Me | RS, R, S | H | — | NH | 1 | H | H |
| 44 | 4-I | NHSO$_2$Me | RS, R ,S | H | — | NH | 1 | H | H |
| 45 | 4-F | NHSO$_2$NMe$_2$ | RS, R, S | H | — | NH | 1 | H | H |
| 46 | 4-Cl | NHSO$_2$NMe$_2$ | RS, R, S | H | — | NH | 1 | H | H |
| 47 | H | SO$_2$NHMe | RS, R, S | H | — | NH | 1 | H | H |
| 48 | H | NHSO$_2$NMe$_2$ | RS, R, S | H | — | NH | 1 | H | H |
| 49 | H | NHSO$_2$Me | RS, R, S | Me | R | NH | 1 | H | H |
| 50 | H | NHSO$_2$CH$_2$Ph | RS, R, S | H | — | NH | 1 | H | H |
| 51 | H | NHCHO | RS, R, S | H | — | NH | 1 | H | H |
| 52 | H | NHSO$_2$Me | RS, R, S | H | — | NH | 1 | H | NHAc |
| 53 | 4-OH | H | RS, R, S | H | — | NH | 1 | H | H |
| 54 | 2-OH | H | RS, R, S | H | — | NH | 1 | H | H |
| 55 | 2-F | H | RS, R, S | H | — | NH | 1 | H | H |
| 56 | H | H | RS, R, S | H | — | NH | 1 | H | H |
| 57 | H | H | RS, R, S | H | — | NH | 1 | NH$_2$ | H |
| 58 | 4-F | NHSO$_2$Me | RS, R, S | H | — | O | 1 | H | H |
| 59 | 4-Cl | NHSO$_2$Me | RS, R, S | H | — | O | 1 | H | H |
| 60 | H | NHSO$_2$Me | RS, R, S | H | — | O | 1 | H | H |
| 61 | 4-OH | NHSO$_2$NME$_2$ | RS, R, S | H | — | S | 1 | H | H |
| 62 | 4-F | NHSO$_2$Me | RS, R, S | H | — | S | 1 | H | H |
| 63 | 4-Cl | NHSO$_2$Me | RS, R, S | H | S | — | 1 | H | H |
| 64 | H | NHSO$_2$Me | RS, R, S | H | — | S | 1 | H | H |
| 65 | 4-OH | NHSO$_2$Me | RS, R, S | H | — | NH | 2 | H | H |
| 66 | 4-OH | SO$_2$NHMe | RS, R, S | H | — | NH | 2 | H | H |
| 67 | 4-Cl | SO$_2$NHMe | RS, R, S | H | — | NH | 2 | H | H |
| 68 | 4-Br | NHSO$_2$Me | RS, R, S | H | — | NH | 2 | H | H |
| 69 | H | NHSO$_2$Me | RS, R, S | H | — | NH | 2 | H | H |

In table 2, an expression of RS in *1 means racemic compound, and expression of [RS, R, S] means, racemic, R and S-compound, respectively, in a compound numerized in the examples.

TABLE 3

| Compound | *Intrinsic activity(%) | ED$_{50}$(nM) |
|---|---|---|
| isoproterenol | 100 | 140 |
| BRL37344 | 29 | 104 |
| CL316, 243 | 9 | 1700 |
| Example 2 | 63 | 0.26 |
| Example 5 | 101 | 570 |
| Example 6 | 84 | 0.021 |
| Example 9 | 47 | 29 |
| Example 14 | 62 | 25 |
| Example 15 | 72 | 40 |
| Example 17 | 78 | 92 |
| Example 22 | 84 | 27 |
| Example 26 | 111 | 31 |
| Example 28 | 96 | 0.11 |

In the table 3: *Relative activity for isoproterenol

In the table 3: * Relative activity for isoproterenol

TABLE 4

| Compound | *Intrinsic activity(%) | ED$_{50}$(nM) |
|---|---|---|
| isoproterenol | 100 | 92 |
| Example 2 | 127 | 2000 |
| Example 6 | 132 | 200 |

TABLE 4-continued

| Compound | *Intrinsic activity(%) | ED$_{50}$(nM) |
| --- | --- | --- |
| Example 26 | 118 | 39 |
| Example 28 | 140 | 400 |

In the table 4: *Relative activity for isoproterenol

In the table 4: * Relative activity for isoproterenol

What is claimed is:

1. A compound represented by the general formula (I) or a salt thereof:

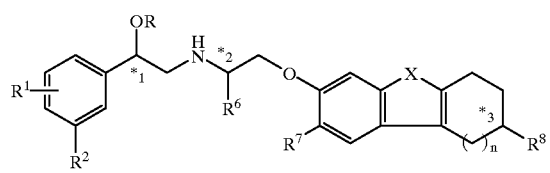

(I)

in which R represents hydrogen atom or methyl, R1 stands for hydrogen atom, halogen atom, hydroxy, benzyloxy, amino or hydroxymethyl, R2 stands for hydrogen atom, hydroxymethyl, NHR3, SO2NR4R4' or nitro, wherein R3 is hydrogen atom, methyl, SO2R5, formyl or CONHR6, with R5 being lower alkyl, benzyl or NR4R4 and R4 and R1' may be identical with or different from each for hydrogen atom, lower alkyl or benzyl, R6' represents hydrogen atom or lower alkyl, and R6 represents hydrogen atom or lower alkyl, n is 1 or 2, and X is secondary nitrogen atom, oxygen atom or sulfur atom and, in case that n is 1, either one of R7 and R8 is hydrogen atom and the other one is hydrogen atom, amino, acetylamino or hydroxy, or, in case that n is 2, R8 is hydrogen atom and R7 is hydrogen atom, amino, acetyl amino or hydroxy, and *1 indicates an asymmetric carbon atom and *2 and *3 indicate that the carbon atom is asymmetric provided that R6 and R8 are not hydrogen atom.

2. A compound represented by the general formula (I) or a salt thereof as claimed in claim 1:

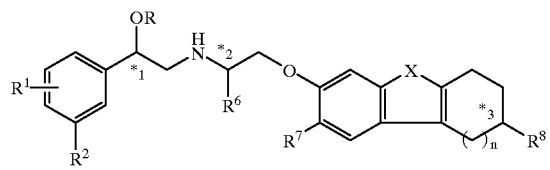

(I)

in which R represents hydrogen atom, R1 stands for hydrogen atom, halogen atom, hydroxy, benzyloxy, amino or hydroxymethyl, R2 stands for hydrogen atom, hydroxymethyl, NHR3, SO2NR4R4' or nitro, wherein R3 is hydrogen atom, methyl, SO2R5, formyl or CONHR6', with R5 being lower alkyl, benzyl or NR4R4' and R6' being hydrogen atom or lower alkyl and R4 and R4' may be identical with or different from each other and stand each for hydrogen atom, lower alkyl or benzyl, R6 represents hydrogen atom or lower alkyl, n is 1 or 2, X is secondary nitrogen atom, oxygen atom or sulfur atom and, in case that n is 1, either one of R7 and R8 is hydrogen atom and the other one is hydrogen atom, amino, acetylamino or hydroxy, or, in case that n is 2, R8 is hydrogen atom and R7 is hydrogen atom, amino, acetylamino or hydroxy, and *1 indicates an asymmetric carbon atom and *2 and *3 indicate that the carbon atom is asymmetric provided that R6 and R8 are not hydrogen atom.

3. A compound represented by the general formula (I) or a salt thereof as claimed in claim 2:

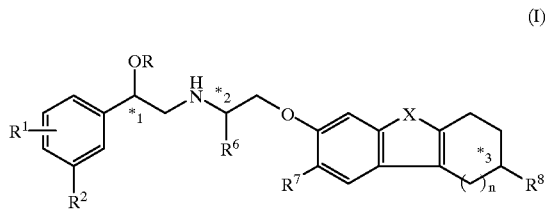

(I)

in which R represents hydrogen atom, R1 stands for hydrogen atom, fluorine atom, chlorine atom, hydroxy or benzyloxy, R2 stands for hydrogen atom, hydroxymethyl, NHR3, SO2NR4R4' or nitro, wherein R3 is hydrogen atom, methyl, SO2R5, formyl or CONHR6' and either one of R4 and R4' is hydrogen atom and the other one is hydrogen atom, lower alkyl or benzyl, with R5 being lower alkyl, benzyl or dimethylamino and R6' being hydrogen atom or lower alkyl, R6 represents hydrogen atom or lower alkyl, n is 1 or 2, X is secondary nitrogen atom, oxygen atom or sulfur atom and, in case that n is 1, either one of R7 and R8 is hydrogen atom and the other one is hydrogen atom, amino, acetylamino or hydroxy, or, in case that n is 2, R8 is hydrogen atom and R7 is hydrogen atom, amino, acetylamino or hydroxy, and *1 indicates an asymmetric carbon atom and *2 and *3 indicate that the carbon atom is asymmetric provided that R6 and R8 are not hydrogen atom.

4. A compound represented by the general formula (I) or a salt thereof as claimed in claim 2:

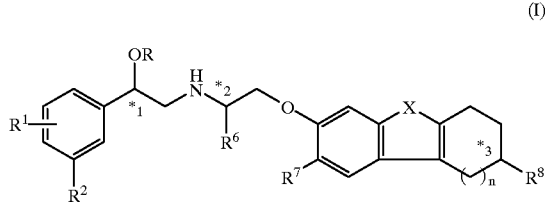

(I)

in which R represents hydrogen atom, R1 stands for hydrogen atom, halogen atom, hydroxy or benzyloxy, R2 stands for hydroxymethyl, NHR3, SO2NR4R4' or nitro, where in RS is hydrogen atom, methyl, SO2R5, formyl or CONHR6' and R4 and R4' may be identical with or different from each other and stand each for hydrogen atom, lower alkyl or benzyl, with R5 being lower alkyl, benzyl or NR4R4' and R6' being hydrogen atom or lower alkyl, R6 represents hydrogen atom or lower alkyl, n is 1 or 2, X is secondary nitrogen atom, oxygen atom, or sulfur atom and, in case that n is 1, either one of R7 and R8 is hydrogen atom and the other one is hydrogen atom, amino, acetylamino or hydroxy, or, in case that n is 2, R8 is hydrogen atom and R7 is hydrogen atom, amino, acetylamino or hydroxy, and *1 indicates an asymmetric carbon atom and *2 and *3 indicate that the carbon atom is asymmetric provided that R6 and R8 are not hydrogen atom.

5. A compound or a salt thereof as claimed in claim 2, wherein, in the general formula (I), both R and R1 represent hydrogen atom, R2 stands for hydroxymethyl, NHR3 or SO2NR4R4', wherein R3 is hydrogen atom, methyl, SO2R5, formyl or CONHR6' and R4 and R4' may be identical with or different from each other and stand each for hydrogen atom, lower alkyl or benzyl, with R5 being lower alkyl, benzyl or NR4R4'.

6. A compound or a salt thereof as claimed in claim 2, wherein, in the general formula (I), R denotes hydrogen atom, R1 stands for halogen atom or hydroxy, R2 stands for NHSO2R5 or SO2NR4R4', wherein R5 is lower alkyl, benzyl or NR4R4 and R4 and R4' may be identical with or different from each other and stand each for hydrogen atom, lower alkyl or benzyl.

7. A compound or a salt thereof as claimed in claim 2, wherein the compound is selected from the group consisting of (R)-N-[5-[2-[2-(5,6,7,8-tetrahydro-9H-carbazol-2-yloxy) ethylamino]-1-hydroxyethyl]-2-hydroxyphenyl] methanesulfonamide;

(S)-N-[5-[2-[2-(5,6,7,8-tetrahydro-9H-carbazol-2-yloxy) ethylamino]-1-hydroxyethyl]-2-hydroxyphenyl] methanesulfonamide;

N-[5-[2-[2-(5,6,7,8-tetrahydro-9H-carbazol-2-yloxy) ethylamino]-1-hydroxyethyl]-2-hydroxyphenyl] methanesulfonamide;

(R)-N-[3-[2-[2-(5,6,7,8-tetrahydro-9H-carbazol-2-yloxy) ethylamino]-1-hydroxyethyl]phenyl] methanesulfonamide;

(S)-N-[3-[2-[2-(5,6,7,8-tetrahydro-9H-carbazol-2-yloxy) ethylamino]-1-hydroxyethyl]phenyl] methanesulfonamide;

N-[3-[2-[2-(5,6,7,8-tetrahydro-9H-carbazol-2-yloxy) ethylamino]-1-hydroxyethyl]phenyl] methanesulfonamide;

N-methyl-3-[2-[2-(5,6,7,8-tetrahydro-9H-carbazol-2-yloxy) ethylamino]-1-hydroxyethyl]benzenesulfonamide;

N-methyl-[5-[2-[2-(5,6,7,8-tetrahydro-9H-carbazol-2-yloxy)ethylamino]-1-hydroxyethyl]-2-hydroxy] benzenesulfonamide;

(R)-N-methyl-[5-[2-[2-(5,6,7,8-tetrahydro-9H-carbazol-2-yloxy)ethylamino]-1-hydroxyethyl]-2-hydroxy] benzenesulfonamide;

N-methyl-[5-[2-[2-(5,6,7,8-tetrahydro-9H-carbazol-2-yloxy)ethylamino]-1-hydroxyethyl]-2-chloro] benzenesulfonamide;

(R)-N-methyl-[5-[2-[2-(5,6,7,8-tetrahydro-9H-carbazol-2-yloxy)ethylamino]-1-hydroxyethyl]-2-chloro 3 benzenesulfonamide;

(R)-N-[5-[2-[2-(6,7,8,9-tetrahydrodibenzofuran-3-yloxy) ethylamino]-1-hydroxyethyl]-2-hydroxyphenyl] methanesulfonamide;

(S)-N-[5-[2-[2-(6,7,8,9-tetrahydrodibenzofuran-3-yloxy) ethylamino]-1-hydroxyethyl]-2-hydroxyphenyl] methanesulfonamide;

N-[5-[2-[2-(6,7,8,9-tetrahydrodibenzofuran-3-yloxy) ethylamino]-1-hydroxyethyl]-2-hydroxyphenyl] methanesulfonamide;

N-[5-[2-[2-(5,6,7,8-tetrahydro-9H-carbazol-2-yloxy) ethylamino]-1-hydroxyethyl]-2-(benzyloxy)phenyl] methanesulfonamide;

N-[5-[2-[2-(5,6,7,8-tetrahydro-9H-carbazol-2-yloxy) ethylamino]-1-hydroxyethyl]-2-chlorophenyl] methanesulfonamide;

N-[5-[2-[2-(5,6,7,8-tetrahydro-9H-carbazol-2-yloxy) ethylamino]-1-hydroxyethyl]-2-chlorophenyl] methanesulfonamide;

N-[3-[2-[2-(6,7,8,9-tetrahydrodibenzofuran-3-yloxy) ethylamino]-1-hydroxyethyl]phenyl] methanesulfonamide;

N-[5-[2-[2-(5,6,7,8-tetrahydro-9H-carbazol-2-yloxy) ethylamino]-1-hydroxyethyl]-2-hydroxyphenyl] formamide;

N-[3-[2-[2-(5,6,7,8-tetrahydro-9H-carbazol-2-yloxy) ethylamino]-1-hydroxyethyl]phenyl]formamide;

N-[3-[2-[[1-(5,6,7,8-tetrahydro-9H-carbazol-2-yloxy) propan-2R-yl]amino]-1-hydroxyethyl]phenyl] methanesulfonamide;

2-[N-[2-(5,6,7,8-tetrahydro-9H-carbazol-2-yloxy)ethyl] amino]-1-(4-hydroxy-3-nitrophenyl)ethanol;

2-[N-[2-(5,6,7,8-tetrahydro-9H-carbazol-2-yloxy)ethyl] amino]-1-(3-amino-4-hydroxyphenyl)ethanol;

N-[5-[2-[2-(5,6,7,8-tetrahydro-9H-carbazol-2-yloxy)ethyl ylamino]-1-hydroxyethyl]-2-hydroxyphenyl]urea;

N'-[5-[2-[2-(5,6,7,8-tetrahydro-9H-carbazol-2-yloxy) ethylamino]-2-(benzyloxy)phenyl]-N,N-dimethylsulfamide;

N'-[5-[2-[2-(5,6,7,8-tetrahydro-9H-carbazol-2-yloxy) ethylamino]-1-hydroxyethyl]-2-hydroxyphenyl]-N,N-dimethylsulfamide;

2-[N-[2-(5,6,7,8-tetrahydro-9H-carbazol-2-yloxy)ethyl] amino]-1-[3-(methylamino)-4-(benzyloxy)phenyl] ethanol;

2-[N-[2-(5,6,7,8-tetrahydro-9H-carbazol-2-yloxy)ethyl] amino]-1-[3-(methylamino)-4-(hdroxyphenyl]ethanol;

N-[5-[2-[2-(5,6,7,8-tetrahydro-9H-carbazol-2-yloxy) ethylamino]-1-hdroxyethyl]-2-hydroxyphenyl]-2-propanesulfonamide;

2-[N-[2-(5,6,7,8-tetrahydro-9H-carbazol-2-yloxy)ethyl] amino]-1-(3-nitrophenyl)ethanol;

N'-[3-[2-[2-(5,6,7,8-tetrahydro-9H-carbazol-2-yloxy) ethylamino]-1-hydroxyethyl]phenyl]-N,N-dimethylsulfamide;

2-[N-[2-(5,6,7,8-tetrahydro-9H-carbazol-2-yloxy)ethyl] amino]-1-(3-aminophenyl)ethanol;

2-[N-[2-(5,6,7,8-tetrahydro-9H-carbazol-2-yloxy)ethyl] amino]-1-[3-(hydroxymethyl)-4-hydroxyphenyl]ethanol;

N-[5-[2-[2-(5,6,7,8-tetrahydro-9H-carbazol-2-yloxy) ethylamino]-1-[3-hydroxyphenyl]methanesulfonamide;

N-[3-[2-[2-(5,6,7,8-tetrahydro-9H-carbazol-2-yloxy) ethylamino]-1-hydroxyethyl]-2-hydroxyphenyl] methanesulfonamide;

N-[3-[2-[2-(5,6,7,8-tetrahydro-9H-carbazol-2-yloxy) ethylamino]-1-hydroxyethyl]-4-hydroxyphenyl] methanesulfonamide;

(R)-N'-[5-[2-[2-(5,6,7,8-tetrahydro-9H-carbazol-2-yloxy) ethylamino]-1-hydroxyethyl]-2-hydroxyphenyl]-N,N-dimethylsulfamide;

(S)-N'-[5-[2-[2-(5,6,7,8-tetrahydro-9H-carbazol-2-yloxy) ethylamino]-1-hydroxyethyl]-2-hydroxyphenyl]-N,N-dimethylsulfamide;

N-[3-[2-[2-(6-acetylamino-5,6,7,8-tetrahydro-9H-carbazol-2-yloxy ethylamino]-1-hydroxyethyl]phenyl] methanesulfonamide;

(R)-N-[5-[2-[2-(5,6,7,8-tetrahydro-9H-carbazol-2-yloxy) ethylamino -1-hydroxyethyl]-2-fluorophenyl] methanesulfonamide;

(S)-N-[5-[2-[2-(5,6,7,8-tetrahydro-9H-carbazol-2-yloxy) ethylamino -1-hydroxyethyl]-2-fluorophenyl] methanesulfonamide;

(R)-N-[5-[2-[2-(5,6,7,8-tetrahydro-9H-carbazol-2-yloxy) ethylamino -1-hydroxyethyl]-2-chlorophenyl] methanesulfonamide;

(S)-N-[5-[2-[2-(5,6,7,8-tetrahydro-9H-carbazol-2-yloxy) ethylamino -1-hydroxyethyl]-2-chlorophenyl] methanesulfonamide;

N,N-dimethyl-[5-[2-[2-(5,6,7,8-tetrahydro-9H-carbazol-2-yloxy)ethylamino]-1-hydroxyethyl]-2-hydroxy] benzensulfonamide;

N-[5-[2-[2-(5,6,7,8-tetrahydro-9H-carbazol-2-yloxy) ethylamino]-1-hydroxyethyl]-2-iodephenyl] methanesulfonamide;

N'-[5-[2-[2-(5,6,7,8-tetrahydro-9H-carbazol-2-yloxy)ethylamino]-1-hydroxyethyl]-2-fluorophenyl]-N,N-dimethylsulfamide;

N'-[5-[2-[2-(5,6,7,8-tetrahydro-9H-carbazol-2-yloxy)ethylamino]-1-hydroxyethyl]-2-chlorophenyl]-N,N-dimethylsulfamide;

(R)-N-methyl-[5-[2-[2-(5,6,7,8-tetrahydro-9H-carbazol-2-yloxy)ethylamino]-1-hydroxyethyl]-2-hydroxy]benzensulfonamide;

(R)-N-[5-[2-[2-(5,6,7,8-tetrahydro-9H-carbazol-2-yloxy)ethylamino -1-hydroxyethyl]-2-hydroxymethyl]phenyl]methanesulfonamide;

(R)-N-[3-[2-[2-(6,7,8,9-tetrahydrodibenzofuran-3-yloxy)ethylamino -1-hydroxyethyl]-1-hydroxymethyl]phenyl]methanesulfonamide;

N'-[5-[2-[2-(6,7,8,9-tetrahydrodibenzofuran-3-yloxy)ethylamino]-1-hydroxyethyl]-2-hydroxyphenyl]-N,N-dimethylsulfamide;

(R)-N'-[5-[2-[2-(6,7,8,9-tetrahydrodibenzofuran-3-yloxy)ethylamino]-1-hydroxyethyl]-2-hydroxyphenyl]-N,N-dimethylsulfamide;

(S)-N'-[5-[2-[2-(6,7,8,9-tetrahydrodibenzofuran-3-yloxy)ethylamino]-1-hydroxyethyl]-2-hydroxyphenyl]-N,N-dimethylsulfamide;

N-[5-[2-[2-(6,7,8,9-tetrahydrodibenzofuran-3-yloxy)ethylamino]-1-hydroxyethyl]-2-fluorophenyl]methanesulfonamide;

N-[5-[2-[2-(6,7,8,9-tetrahydrodibenzofuran-3-yloxy)ethylamino]-1-hydroxyethyl]-2-chlorophenyl]methanesulfonamide;

N-[5-[2-[2-(6,7,8,9-tetrahydrodibenzothiophen-3-yloxy)ethylamino -1-hydroxyethyl]-2-hydroxyphenyl]methanesulfonamide;

N'-[5-[2-[2-(6,7,8,9-tetrahydrodibenzothiophen-3-yloxy)ethylamino]-1-hydroxyethyl]-2-hydroxyphenyl]-N,N-dimethylsulfamide;

N-[3-[2-[2-(6,7,8,9-tetrahydrodibenzothiophen-3-yloxy)ethylamino -1-hydroxyethyl]phenyl]methanesulfonamide;

(R)-N-[5-[2-[2-(6,7,8,9-tetrahydrodibenzothiophen-3-yloxy)ethylamino]-1-hydroxyethyl]-2-hydroxyphenyl]methanesulfonamide;

N-[5-[2-[2-(6,7,8,9-tetrahydrodibenzothiophen-3-yloxy)ethylamino]-1-hydroxyethyl]-2-fluorophenyl]methanesulfonamide;

N-[5-[2-[2-(6,7,8,9-tetrahydrodibenzothiophen-3-yloxy)ethylamino]-1-hydroxyethyl]-2-chlorophenyl]methanesulfonamide;

N'-[5-[2-[2-(5,6,7,8-tetrahydro-9H-carbazol-2-yloxy)ethylamino]-1-hydroxyethyl]-2-aminophenyl]-N-benzyl-N-methylsulfamide;

N-[5-[2-[2-(5,6,7,8-tetrahydro-9H-carbazol-2-yloxy)ethylamino]-1-hydroxyethyl]-2-aminophenyl]methanesulfonamide;

N-[5-[2-[2-(5,6,7,8-tetrahydro-9H-carbazol-2-yloxy)ethylamino]-1-hydroxyethyl]-2-(hydroxymethyl)phenyl]methanesulfonamide;

N-[5-[2-[2-(5,6,7,8-tetrahydro-9H-carbazol-2-yloxy)ethylamino]-1-hydroxyethyl]-2-bromophenyl]methanesulfonamide;

(R)-N-[5-[2-[2-(5,6,7,8-tetrahydro-9H-carbazol-2-yloxy)ethylamino]-1-hydroxyethyl]-2-bromophenyl]methanesulfonamide;

N'-[5-[2-[2-(5,6,7,8-tetrahydro-9H-carbazol-2-yloxy)ethylamino -1-hydroxyethyl]-2-hydroxyphenyl]-N-benzyl-methylsulfamide;

N'-[5-[2-[2-(5,6,7,8-tetrahydro-9H-carbazol-2-yloxy)ethylamino -1-hydroxyethyl]-2-hydroxyphenyl]-N,N-diethylsulfamide;

(R)-N-[5-[2-[2-(5,6,7,8,9,10-hexahydro-cyclohepta[b]indole-2-yloxy)ethylamino]-1-hydroxyethyl]-2-hydroxyphenyl]methanesulfonamide;

(S)-N-[5-[2-[2-(5,6,7,8,9,10-hexahydro-cyclohepta[b]indole-2-yloxy)ethylamino]-1-hydroxyethyl]-2-hydroxyphenyl]methanesulfonamide;

N-[5-[2-[2-(5,6,7,8,9,10-hexahydro-cyclohepta[b]indole-2-yloxy)ethylamino]-1-hydroxyethyl]-2-hydroxyphenyl]methanesulfonamide;

(R)-N-[3-[2-[2-(5,6,7,8,9,10-hexahydro-cyclohepta[b]indole -2-yloxy)ethylamino]-1-hydroxyethyl]phenyl]methanesulfonamide;

N-[3-[2-[2-(5,6,7,8,9,10-hexahydro-cyclohepta[b]indole-2-yloxy)ethylamino]-1-hydroxyethyl]phenyl]methanesulfonamide;

(R)-N-methyl-[5-[2-[2-(5,6,7,8,9,10-hexahydro-cyclohepta[b]indole-2-yloxy)ethylamino]-1-hydroxyethyl]-2-hydroxy]-benzenesulfonamide;

(R)-N-methyl-[5-[2-[2-(5,6,7,8,9,10-hexahydro-cyclohepta[b]indole-2-yloxy)ethylamino]-1-hydroxyethyl]-2-chloro]benzenesulfonamide;

N'-[5-[2-[2-(5,6,7,8,9,10-hexahydro-cyclohepta[b]indole-2-yloxy)ethylamino]-1-hydroxyethyl]-2-hydroxyphenyl]-N,N-diethylsulfamide;

(R)-N'-[5-[2-[2-(5,6,7,8,9,10-hexahydro-cyclohepta[b]indole-2-yloxy)ethylamino]-1-hydroxyethyl]-2-hydroxyphenyl]-N,N-diethylsulfamide;

(R)-N-[5-[2-[2-(5,6,7,8,9,10-hexahydro-cyclohepta[b]indole-2-yloxy)ethylamino]-1-hydroxyethyl]-2-bromophenyl]methanesulfonamide;

(R)-N-[5-[2-[2-(5,6,7,8,9,10-hexahydro-cyclohepta[b]indole-2-yloxy)ethylamino]-1-hydroxyethyl]-2-chlorophenyl]methanesulfonamide;

(R)-N-[5-[2-[2-(5,6,7,8,9,10-hexahydro-cyclohepta[b]indole-2-yloxy)ethylamino]-1-hydroxyethyl]-2-fluorophenyl]methanesulfonamide.

8. A compound represented by the general formula (I) and a salt thereof as claimed in claim 2,

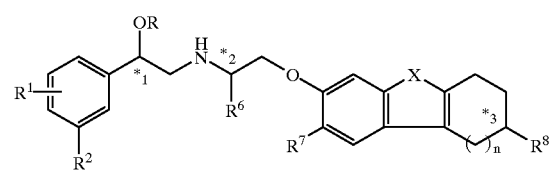

wherein R represents hydrogen atom, R1 stands for hydrogen atom, halogen atom or hydroxy, R2 stands for hydrogen atom, R6 represents hydrogen atom or lower alkyl, n is 1 or 2, X is secondary nitrogen atom, oxygen atom or sulfur atom, in case that n is 1, either one of R7 and R8 is hydrogen atom and the other one is hydrogen atom, amino, acetylamino or hydroxy, or, in case that n is 2, R8 is hydrogen atom and R7 is hydrogen atom, amino, acetylamino or hydroxy, and *1 indicates an asymmetric carbon atom and *2 and *3 indicate that the carbon atom is asymmetric provided that R6 and R8 are not hydrogen atom.

9. A compound or a salt thereof as claimed in claim 8, wherein the compound is selected from the group consisting of 2-[N-[2-(5,6,7,8-tetrahydro-9H-carbazol-2-yloxy)ethyl]amino]-1(4-hydroxyphenyl)ethanol, 2-[N-[2-(5,6,7,8-tetrahydro-9H-carbazol-2-yloxy)ethyl]amino]-1(2-fluorophenyl)ethanol, 2-[N-[2-(5,6,7,8-tetrahydro-9H-carbazol-2-yloxy)ethyl]amino]-1(2-hydroxyphenyl)ethanol, (R,R)-2-[N-[1-(5,6,7,8-tetrahydro-9H-carbazol-2-yloxy) propan -2-yl]amino]-1-phenylethanol,
2-[N-[2-(5,6,7,8-tetrahydro-9H-carbazol-2-yloxy)ethyl] amino]-1-phenylethanol,
(R)-2-[N-[2-(5,6,7,8-tetrahydro-9H-carbazol-2-yloxy)ethyl] amino]-1-phenylethanol,
(S)-[2-[N-2-(5,6,7,8-tetrahydro-9H-carbazol-2-yloxy)ethyl] amino]-1-phenylethanol,
2-[N-[2-(3-acetylamino-5,6,7,8-tetrahydro-9H-carbazol-2-yloxy)ethyl]amino]-1-phenylethanol,
2-[N-[2-(3-amino-5,6,7,8-tetrahydro-9H-carbazol-2-yloxy) ethyl]amino]-1-phenylethanol,
2-[N-[1-(5,6,7,8-tetrahydro-9H-carbazol-2-yloxy)propan-2-yl]amino]-1-phenylethanol and
2-[N-[2-(6,7,8,9-tetrahydrobenzofuran-3-yloxy)ethyl] amino]-1-phenylethanol.

10. A compound represented by the general formula (I) or a salt thereof as claimed in claim 1,

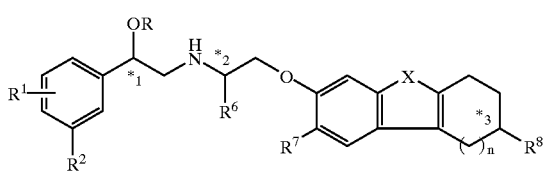

(I)

wherein R represents methyl, R1 stands for hydrogen atom, halogen atom, hydroxy, amino or hydroxymethyl, R2 stands for NHR2 or SO2NR4R4',R3 represents SO2R5, with R5 being lower alkyl, benzyl or NR4R4' and R4 and R4 may be identical with or different from each other and stand each for hydrogen atom, lower alkyl or benzyl, R6 represents hydrogen atom or lower alkyl, n is 1 or 2, X is secondary nitrogen atom, oxygen atom or sulfur atom and, in case that n is 1, either one of R7 and R8 is hydrogen atom and the other one is hydrogen atom, amino, acetylamino or hydroxy, or, in case that n is 2, R8 is hydrogen atom and R7 is hydrogen atom, amino, acethylamino or hydroxy, and *1 indicates an asymmetric carbon atom and *2 and *3 indicate that the carbon atom is asymmetric provided that R6 and R8 are not hydrogen atom.

11. A compound or a salt thereof as claimed in claim 10, wherein the compound is selected from the group consisting of
N-[5-[2-[2-(5,6,7,8-tetrahydro-9H-carbazol-2-yloxy) ethylamino]-1-methoxyethyl]-2-hydroxyphenyl] methanesulfonamide;
N-[5-[2-[2-(6,7,8,9-tetrahydrodibenzothiophen-3-yloxy) ethylamino]-1-methoxyethyl]-2-hydroxyphenyl] methanesulfonamide;
N-[5-[2-[2-(5,6,7,8-tetrahydro-9H-carbazol-2-yloxy) ethylamino]-1-methoxyethyl]-2-aminophenyl] methanesulfonamide.

12. A medicament containing, as an active ingredient, a compound or a salt thereof as claimed in claim 1.

13. A medicament as claimed in claim 12, wherein it is a drug composition containing, as an active ingredient a compound or a salt thereof as claimed in claim 1 and a carrier medicamentally acceptable for the effective component.

14. A medicament as claimed in claim 12, which is a drug to be served for therapeutic treatment or preventive treatment of either one of diabetes, obesity and hyperlipemia.

15. A method for producing a compound represented by the general formula (I)

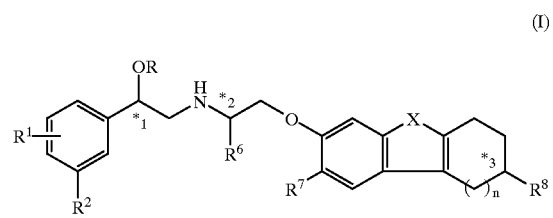

(I)

in which R represents hydrogen atom, R1 stands for hydrogen atom, halogen atom, hydroxy, benzyoxy, amino or hydroxymethyl, R2 stands for hydrogen atom, hydroxymethyl, NHR3, SO2NR4R4' or nitro, wherein R3 is hydrogen atom, methyl, SO2R5, formyl or CONHR6', n is 1 or 2, with R5 being lower alkyl, benzyl or NR4R4' and R4 and R4' may be identical with or different from each other and stand each for hydrogen atom, lower alkyl or benzyl, and R6' being hydrogen atom or lower alkyl, R6 represents hydrogen atom or lower alkyl, X is secondary nitrogen atom or sulfur and, in case that n is 1, either one of R7 and R8 is hydrogen atom and the other one is hydrogen atom, amino, acetylamino or hydroxy, or, in case that n is 2, R8 is hydrogen atom, and R7 is hydrogen atom, amino, acetylamino or hydroxy, and *1 indicates an asymmetric carbon atom and *2 and *3 indicate that the carbon is asymmetric provided that R6 and R8 are not hydrogen, characterized in that a compound represented by the general formula (II)

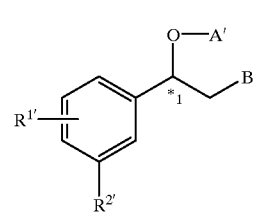

(II)

[in which R1' represents hydrogen atom, halogen atom, a protected hydroxyl group protected by a protecting group A, a protected amino group protected by acetyl group or a protected hydroxymethyl group protected by acetyl group, R2' stands for hydrogen atom, for a protected hydroxymethyl group in which the hydroxyl group is protected by a protecting group A'" for NHR3', for SO2NR4R4 or for nitro, wherein R3' represents a protecting group for the amino group, methyl, SO2R5, formyl or CONHR6 , with R5 being lower alkyl, benzyl or NR4R4' and R6' being hydrogen atom or lower alkyl, R4 and R4' may be identical with or different from each other and stand each for hydrogen atom, lower alkyl or benzyl, R6 denotes hydrogen atom or lower alkyl, A' represents a protecting group for the hydroxy group, B is bromine atom or iodine atomand *1 indicates an asymmetric carbon atom]is reacted with a compound represented by the general formula (III)

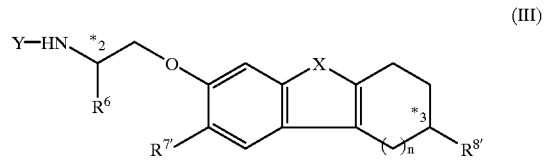

(III)

[in which Y represents hydrogen atom, R6 is hydrogen atom or lower alkyl, n is 1 or 2, X is secondary nitrogen atom, oxygen atom or sulfur atom and, in case that n is 1, either one of R7' and R8' is hydrogen atom, acetylamino or a protected hydroxyl group protected by a protecting group A" or, in case n is 2, R8' is hydrogen atom and R7' is hydrogen atom, cetylamino or a protected hydroxyl group protected by a proptecting group A", and *2 and *3 indicate that the carbon atom is asymmetric provided that R6 and R8' are not hydrogen atom], whereupon the protecting groups A, A', A" and A'" as well as the protecting group for the amino group in R3' and the protecting acetyl group in R1' are eliminated for protection with the proviso that the protecting group A is not eliminated if A is benzyl and R1 is benzyloxy.

16. A compound represented by the general formula (III)

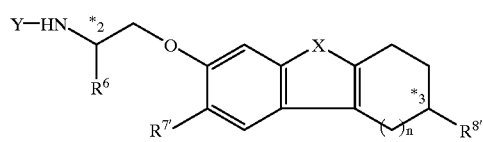

(III)

in which Y is hydrogen atom or protective group for amine, R6 is hydrogen atom or lower alkyl, n is 1 or 2, X is secondary nitrogen, oxygen or sulfur, when n is 1, either one of R7' or R8' is hydrogen atom and the other is hydrogen atom, acetylamino or hydroxy protected by protective group A", when n is 2, R8' is hydrogen atom and R7' is hydrogen atom, acetylamino or hydroxy protected by protective group A", and *2 and *3 indicate an asymmetric carbon atom when R6 and R8' are not hydrogen atom.

17. A compound represented by the general formula (IV)

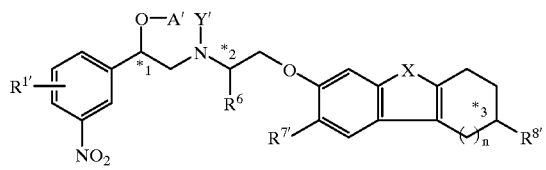

(IV)

in which R1' represents hydrogen atom, halogen atom, a protected hydroxy group protected by a protecting group A, a protected amino group protected by acetyl group or a protected hydroxymethyl group in which the hydroxy group is protected by acetyl group, R6 stans for hydrogen atom or lower alkyl, Y' is hydrogen atom or a protecting group for the amine, n is 1 or 2, X is secondary nitrogen atom, oxygen atom or sulfur atom and, in case that n is 1, either one of R7' and R8' is hydrogen atom and the other one is acetylamino or a protected hydroxy group protected by a protecting group A", or, in case that n is 2, R8' is hydrogen atom and R7' is hydrogen atom, acetylamino or a protected hydroxyl group protected by a protecting group A", A' represents a protecting group for the hydroxy group, *1 indicates an asymmetric carbon atom and *2 and *3 indicate that the carbon atom is asymmetric provided that R6 and R8' are not hydrogen atom.

* * * * *